(12) United States Patent
Louwrier

(10) Patent No.: US 11,919,947 B2
(45) Date of Patent: *Mar. 5, 2024

(54) ANTIBODY BINDING ACTIVE α-SYNUCLEIN

(71) Applicant: Stressmarq Biosciences Inc., Victoria (CA)

(72) Inventor: Ariel Louwrier, Victoria (CA)

(73) Assignee: STRESSMARQ BIOSCIENCES INC., Victoria (CA)

(*) Notice: Subject to any disclaimer, the term of this patent is extended or adjusted under 35 U.S.C. 154(b) by 301 days.

This patent is subject to a terminal disclaimer.

(21) Appl. No.: 17/381,661

(22) Filed: Jul. 21, 2021

(65) Prior Publication Data

US 2021/0355202 A1 Nov. 18, 2021

Related U.S. Application Data

(63) Continuation of application No. 16/635,943, filed as application No. PCT/CA2018/050952 on Aug. 2, 2018, now Pat. No. 11,098,108.

(Continued)

(51) Int. Cl.
*C07K 16/18* (2006.01)
*A61P 25/28* (2006.01)
(Continued)

(52) U.S. Cl.
CPC .............. *C07K 16/18* (2013.01); *A61P 25/28* (2018.01); *G01N 33/6896* (2013.01);
(Continued)

(58) Field of Classification Search
None
See application file for complete search history.

(56) References Cited

U.S. PATENT DOCUMENTS 8,809,506 B2  8/2014  Lannfelt et al.
8,940,276 B2  1/2015  Weihofen et al.
(Continued)

FOREIGN PATENT DOCUMENTS

CA   3000560            4/2017
WO   WO-2008068048 A2 * 6/2008 ............. A61P 31/10
(Continued)

OTHER PUBLICATIONS

Kussie et al., A single engineered amino acid substitution changes antibody fine specificity.J Immunol. Jan. 1, 1994;152(1):146-52. (Year: 1994).*

(Continued)

*Primary Examiner* — Aurora M Fontainhas
(74) *Attorney, Agent, or Firm* — Procopio, Cory, Hargreaves & Savitch LLP

(57) ABSTRACT

A monoclonal antibody that binds α-synuclein, and that binds tau fibrils, and methods of using the monoclonal antibody, are provided. The monoclonal antibody may be hybridoma clone 2F11. Also provided is a composition comprising the monoclonal antibody 2F11 and a pharmaceutically acceptable carrier, adjuvant, vehicle or excipient. A method of reducing active α-synuclein in a subject in need thereof is also disclosed. The method involves administering an amount of the composition comprising 2F11 to the subject. The monoclonal antibody 2F11 may also be used to determine the α-synuclein, or tau fibril, level in a biological sample.

19 Claims, 21 Drawing Sheets

Specification includes a Sequence Listing.

Related U.S. Application Data

(60) Provisional application No. 62/540,435, filed on Aug. 2, 2017.

(51) Int. Cl.
*G01N 33/68* (2006.01)
*A61K 39/00* (2006.01)

(52) U.S. Cl.
CPC .... *A61K 2039/505* (2013.01); *C07K 2317/31* (2013.01); *C07K 2317/565* (2013.01); *G01N 2800/7047* (2013.01)

(56) References Cited

U.S. PATENT DOCUMENTS

| | | | |
|---|---|---|---|
| 9,084,832 | B2 | 7/2015 | Nordstrom et al. |
| 11,098,108 | B2 | 8/2021 | Louwrier |
| 2004/0143093 | A1 | 7/2004 | Zahn et al. |
| 2017/0355756 | A1* | 12/2017 | Julien ............... A61P 25/00 |
| 2018/0002433 | A1 | 1/2018 | Zhang et al. |

FOREIGN PATENT DOCUMENTS

| | | |
|---|---|---|
| WO | 2009133521 A2 | 11/2009 |
| WO | 2012075037 A1 | 6/2012 |
| WO | 2012177972 A1 | 12/2012 |
| WO | 2012177997 A1 | 12/2012 |
| WO | 2015131256 | 9/2015 |
| WO | 2015131257 | 9/2015 |
| WO | 2015131258 | 9/2015 |

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; https://doi.org/10.1073/pnas.1613231114 (Year: 2017).*

Alderson et al. "Disorder in the court" Nature 530, 38-39 (2016).

Altschul et al. "Basic Local Alignment Search Tool" J. Mol. Biol. 215:403-410 (1990).

Altschul et al. "Gapped BLAST and PSI-BLAST: a new generation of protein database search programs" Nuc. Acids Res. 25:3389-3402 (1997).

Ardah et al., "Ginsenoside rb1 inhibits fibrillation and toxicity of alpha-synuclein and disaggregates preformed fibrils," Neurobiol Dis .; 74: 89-101. doi:10.1016/j.nbd.2014.11.007 (2015).

Ariesandi et al. "Temperature-Dependent Structural Changes of Parkinson's Alpha-Synuclein Reveal the Role of Pre-Existing Oligomers in Alpha-Synuclein Fibrillization" PLoS One, 8(1); e53487 (2013).

Badiola et al., "Tau Enhances a-Synuclein Aggregation and Toxicity in Cellular Models of Synucleinopathy," PLoS One, e26609, Issue 10 (2011).

Bae et al. "Antibody-Aided Clearance of Extracellular α-Synuclein Prevents Cell-to-Cell Aggregate Transmission" Journal of Neuroscience, 32(39):13454-13469 (2012).

Bartels et al. "α-Synuclein Occurs Physiologically as a Helically Folded Tetramer That Resists Aggregation" Nature, 477, 107-110 (2011).

Bédard et al. "Besides Fibrillization: Putative Role of the Peptide Fragment 71-82 on the Structural and Assembly Behavior of the α-Synuclein" Biochemistry, 53, 6463-6472 (2014).

Bengoa-Vergniory et al. "Alpha-synuclein oligomers: a new hope" Acta Neuropathol. vol. 134, No. 6, pp. 819-838 (2017).

Benussi et al. "Interaction between tau and alpha-synuclein proteins is impaired in the presence of P301L tau mutation" Exp. Cell Res. 308:78-84 (2005).

Berge et al. "Review Article: Pharmaceutical Salts" J. Pharm Sci. 66:1-19 (1977).

Bien-Ly et al. "Transferrin receptor (TfR) trafficking determines brain uptake of TfR antibody affinity variants" J. Exp. Med. 211:233-244 (2014).

Bohm et al. "Quantitative Analysis of Protein Far UV Circular Dichroism Spectra by Neural Networks" Protein Eng. 5, 191-195 (1992).

Borghi et al. "Full length alpha-synuclein is present in cerebrospinal fluid from Parkinson's disease and normal subjects" Neurosci Lett; 287:65-7 (2000).

Cappai et al. "Dopamine promotes α-synuclein aggregation into SDS-resistant soluble oligomers via a distinct folding pathway" FASEB J. 2005, 19, 1377-1379 (2005).

Comellas et al. "Structural intermediates during a-synuclein fibrillogenesis on phospholipid vesicles" J. Am. Chem. Soc. 134, 5090-5099 (2012).

Congdon et al. "Tau-targeting therapies for Alzheimer disease" Nat. Rev. Neurol., published on-line Jun. 12, 2018, Nature.com/nrneurol (2018).

Cremades et al. "Direct Observation of the Interconversion of Normal and Toxic Forms of α-Synuclein" Cell, 149, 1048-105 (2012).

Desplats et al. "Inclusion formation and neuronal cell death through neuron-to-neuron transmission of synuclein" PNAS, 106, 13010-13015 (2009).

Deyev et al. "Multivalency: the hallmark of antibodies used for optimization of tumor targeting by design" BioEssays, 30:904-918 (2008).

El-Agnaf et al. "Detection of oligomeric forms of alpha-synuclein protein in human plasma as a potential biomarker for Parkinson's disease" FASEB J, 20:419-25 (2006).

Giasson et al. "A panel of Epitope-specific antibodies detects protein domains distributed throughout human α-synuclein in Lewy bodies in Parkinson's disease" J. Neurosci. Res. 59, 528-533 (2000).

Giasson et al. "A Hydrophobic Stretch of 12 Amino Acid Residues in the Middle of α-Synuclein is Essential for Filament Assembly" J. Biol. Chem. 276, 2380-2386 (2001).

Guo et al., "Distinct a-Synuclein Strains Differentially Promote Tau Inclusions in Neurons," Cell 154, pp. 103-117 (2013).

Hamilton, "Lewy Bodies in Alzheimer's Disease: A Neuropathological Review of 145 Cases Using a-Synuclein Immunohistochemistry," Brain Pathology 10: 378-384(2000).

Hansen et al. "α-Synuclein propagates from mouse brain to grafted dopaminergic neurons and seeds aggregation in cultured human cells" J. Clin. Invest., 121, 715-725 (2011).

Henikoff and Henikoff "Amino acid substitution matrices from protein blocks" Proc. Natl. Acad. Sci. USA 89:10915-10919 (1992).

Horvath et al. "Modulation of α-synuclein fibrillization by ring-fused 2-pyridones: Templation and inhibition involve oligomers with different structures" Archives of Biochemistry and Biophysics, vol. 532, Issue 2, pp. 84-90 (2013).

Jo et al. "α-Synuclein Membrane Interactions and Lipid Specificity" J. Biol. Chem. 275, 34328-34334 (2000).

Jones et al. "Replacing the complementarity-determining regions in a human antibody with those from a mouse" Nature, 321:522-525 (1986).

Kasuga et al. "Differential levels of α-synuclein, β-amyloid42 and tau in CSF between patients with dementia with Lewy bodies and Alzheimer's disease" J Neurol Neurosurg Psychiatry, 81:608-10 (2010).

Kayed et al. "Fibril specific, conformation dependent antibodies recognize a generic epitope common to amyloid fibrils and fibrillar oligomers that is absent in prefibrillar oligomers" Molecular Neurodegeneration, 2:18, 11 pages (2007).

Kim et al., "The Inhibitory Effect of Pyrroloquinoline Quinone on the Amyloid Formation and Cytotoxicity of Truncated Alpha-Synuclein," Molecular Neurodegeneration, 5:20 (2010).

Kim et al. "Exposure to bacterial endotoxin generates a distinct strain of α-synuclein fibril" Nature: Scientific Reports, 6: 30891, 12 pages (2016).

(56) References Cited

OTHER PUBLICATIONS

Kostka et al. "Single Particle Characterization of Iron-induced Pore-forming α-Synuclein Oligomers" J. Biol. Chem., 283, 10992-11003 (2008).
Kovacs "Invited review: Neuropathology of tauopathies: principles and practice" Neuropathology Applied Neurobiology, 41, 3-23 (2015).
Lashuel et al. "α-Synuclein, Especially the Parkinson's Disease-associated Mutants, Forms Pore-like Annular and Tubular Protofibrils" J. Mol. Biol. 322, 1089-1102 (2002).
Lee et al. "Membrane-bound α-Synuclein Has a High Aggregation Propensity and the Ability to Seed the Aggregation of the Cytosolic Form" J. Biol. Chem. 277, 671-678 (2002).
Lee et al. "Enzyme-linked immunosorbent assays for alpha-synuclein with species and multimeric state specificities" Journal of Neuroscience Methods 199; 249- 257 (2011).
Li et al. "Characterization of Two VQIXXK Motifs for Tau Fibrillization in Vitro" Biochemistry 45(51):15692-15701 (2006).
Li et al. "Interactions Between α-Synuclein and Tau Protein: Implications to Neurodegenerative Disorders" J. Mol. Neurosci., 60:298-304 (2016).
Li et al., "Aggregation Promoting C-terminal Truncation of a-Synuclein is a Normal Cellular Process and is Enhanced by the Familial Parkinson's Disease-Linked Mutations," PNAS, vol. 102, No. 6 pp. 2162-2167 (2005).
Lindstrom et al. "Immunotherapy targeting a-synuclein protofibrils reduced pathology in (Thy-1)-h[A30P] a-synuclein mice" Neurobiol. Dis. 69, pp. 134-143 (2014).
Lorenzen et al. "The Role of Stable α-Synuclein Oligomers in the Molecular Events Underlying Amyloid Formation" J. Am. Chem. Soc., 136, 3859-3868 (2014).
Luk et al. "Exogenous α-synuclein fibrils seed the formation of Lewy body-like intracellular inclusions in cultured cells," PNAS, 106(47), 20051-20056 (2009).
Majbour et al., "Oligomeric and Phosphorylated Alpha-Synuclein as Potential CSF Biomarkers for Parkinson's Disease," Molecular Neurodegeneration, 11:7 DOI 10.1186/s13024-016-0072-9 (2016).
Masliah et al. "Effects of α-Synuclein Immunization in a Mouse Model of Parkinson's Disease" Neuron, 46:857-868 (2005).
Masliah et al. "Passive immunization reduces behavioral and neuropathological deficits in an alpha synuclein transgenic model of Lewy body disease" PLoS One 6:e19338, 17 pages (2011).
Morrison et al. "Genetically Engineered Antibody Molecules" Adv. Immunol., 44:65-92 (1989).
Morrison et al. "Chimeric human antibody molecules: Mouse antigen-binding domains with human constant region domains" Proc. Natl. Acad. Sci. USA, 81:6851-6855 (1984).
Moussaud et al., "Alpha-Synuclein and Tau: Teammates in Neurodegeneration?," Molecular Neurodegeneration, 9:43 http://www.molecularneurodegeneration.com/content/9/1/43 (2014).
Murray et al. "Role of α-synuclein carboxy-terminus on fibril formation in vitro" Biochemistry, 42, 8530- 8540 (2003).
Needleman and Wunsch "Description of the method used in PCOMPARE and SCANISM" J. Mol. Biol. 48:443 (1970).
Padlan "A Possible Procedure for Reducing the Immunogenicity of Antibody Variable Domains While Preserving Their Ligand-Binding Properties" Molec. Immun. 28:489-498 (1991).
Padlan "Review: Anatomy of the Antibody Molecule" Molec. Immun. 31(3):169-217 (1994).
Pearson and Lipman "Improved tools for biological sequence comparison" Proc. Natl. Acad. Sci. USA 85:2444-2448 (1988).
Perrin et al. "Exposure to long chain polyunsaturated fatty acids triggers rapid multimerization of synucleins" J. Biol. Chem. 276, 41958-41962 (2001).
Presta "Antibody engineering" Curr. Op. Struct. Biol. 2:593-596 (1992).

Reardon "Alzheimer's drug sneaks through blood-brain barrier" Nature, https://www.nature.com/news/alzheimer-s-drug-sneaks-through-blood-brain-barrier-1.16291, 4 pages (2014).
Riechmann et al. "Reshaping human antibodies for therapy" Nature 332:323-327 (1988).
Roberts and Brown "Seeking a Mechanism for the Toxicity of Oligomeric α-Synuclein" Biomolecules 5:282-305 (2015).
Schmid et al., "Alpha-synuclein Post-translational Modifications as Potential Biomarkers for Parkinson Disease and Other Synucleinopathies," Molecular & Cellular Proteomics 12.12, The American Society for Biochemistry and Molecular Biology, Inc., pp. 3543-3558 (2013).
Shvadchak et al. "Fibril breaking accelerates α-synuclein fibrillization" J. Phys. Chem. B., 119, 1912- 1918 (2015).
Smith and Waterman "Comparison of Biosequences" Adv. Appl. Math. 2:482-489 (1981).
Theillet et al. "Structural disorder of monomeric α-synuclein persists in mammalian cells" Nature 530, 45-50 (2016).
Verhoeyen et al. "Reshaping Human Antibodies: Grafting an Antilysozyme Activity" Science 239:1534-1536 (1988).
Volpicelli-Daley et al. "Addition of exogenous α-Synuclein Preformed fibrils to Primary Neuronal Cultures to seed recruitment of endogenous α-Synuclein to Lewy body and Lewy Neurite-like aggregates" Nature Protocols, 9(9), 2135-2146 (2014).
Wang et al. "A soluble α-synuclein construct forms a dynamic tetramer" Proc. Natl. Acad. Sci. USA, 108:17797-17802 (2011).
Williams et al., "Differential Cross-Seeding Properties of Tau and a-Synuclein in Mouse Models of Tauopathy and Synucleinopathy," Brain Communications, doi:10.1093/braincomms/fcaa090 (2020).
Yan et al. "The interaction of α-synuclein and Tau: A molecular conspiracy in neurodegeneration?" Seminars in Cell Devel. Biol., 99, pp. 55-64, available at URL: doi.org/10.1016/j.semcdb.2018.05.005 (2018).
Zhang et al. "In vitro study of α-synuclein protofibrils by cryo-EM suggests a Cu2+ -dependent aggregation pathway" Biophys. J., 104, 2706-2713 (2013).
Zuchero et al. "Discovery of Novel Blood-Brain Barrier Targets to Enhance Brain Uptake of Therapeutic Antibodies" Neuron 89:70-82 (2016).
Vaikath et al., "Generation and characterization of novel conformation-specific monoclonal antibodies for [alpha]-synuclein patho", Neurobiology of Disease, vol. 79 , pp. 81-99.
El-Agnaf et al., "Differential effects of immunotherapy with antibodies targeting [alpha]-synuclein oligomers and fibrils in a transgenic model of synucleinopathy", Neurobiology of Disease, Elsevier, Amsterdam, Nl, vol. 104, pp. 85-96, XP085051562, ISSN: 0969-9961, DOI: 10.1016/J.NBD.2017.05.002 (2017).
Fagerqvist et al., "Monoclonal antibodies selective for [alpha]-synuclein oligomers/protofibrils recognize brain pathology in Lewy body disorders and [alpha]-synuclein transgenic mice with the disease-causing A3OP mutation", Journal of Neurochemistry, vol. 126, No. 1, pp. 131-144, XP055399050, GB ISSN: 0022-3042, DOI: 10.1111/jnc.12175 (2013).
Covell et al., "Novel conformation-selective alphasynuclein antibodies raised against different in vitro fibril forms show distinct patterns of Lewy pathology in Parkinson's disease", Neuropathology and Applied Neurobiology., vol. 43, No. 7, pp. 604-620, XP055545043, GB ISSN: 0305-1846, DOI: 10.1111/nan.12402 (2017).
Vaikath et al., "Antibodies against alpha-synuclein: tools and therapies", Journal of Neurochemistry, vol. 150, No. 5, pp. 612-625, XP055643972, GB ISSN: 0022-3042, DOI: 10.1111/jnc.14713 (2019).
International Search Report and Written Opinion dated Oct. 25, 2018 in Application No. PCT/CA2018/050952.
European Search Report dated Mar. 16, 2021 in European Patent Application No. 18840781.
Corrected Notice of Allowability for U.S. Appl. No. 16/635,943, dated Jun. 28, 2021, 8 pgs.

* cited by examiner

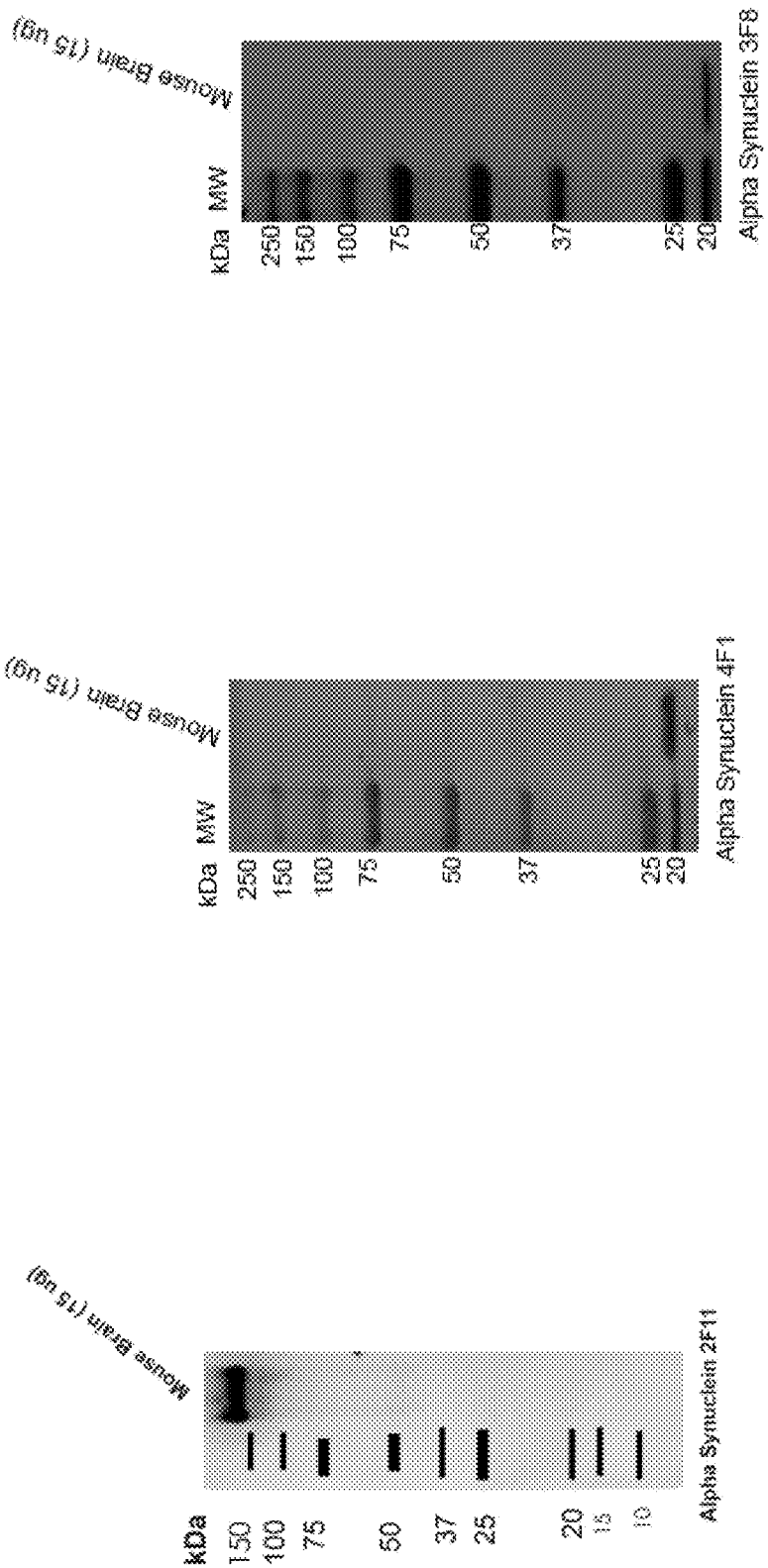

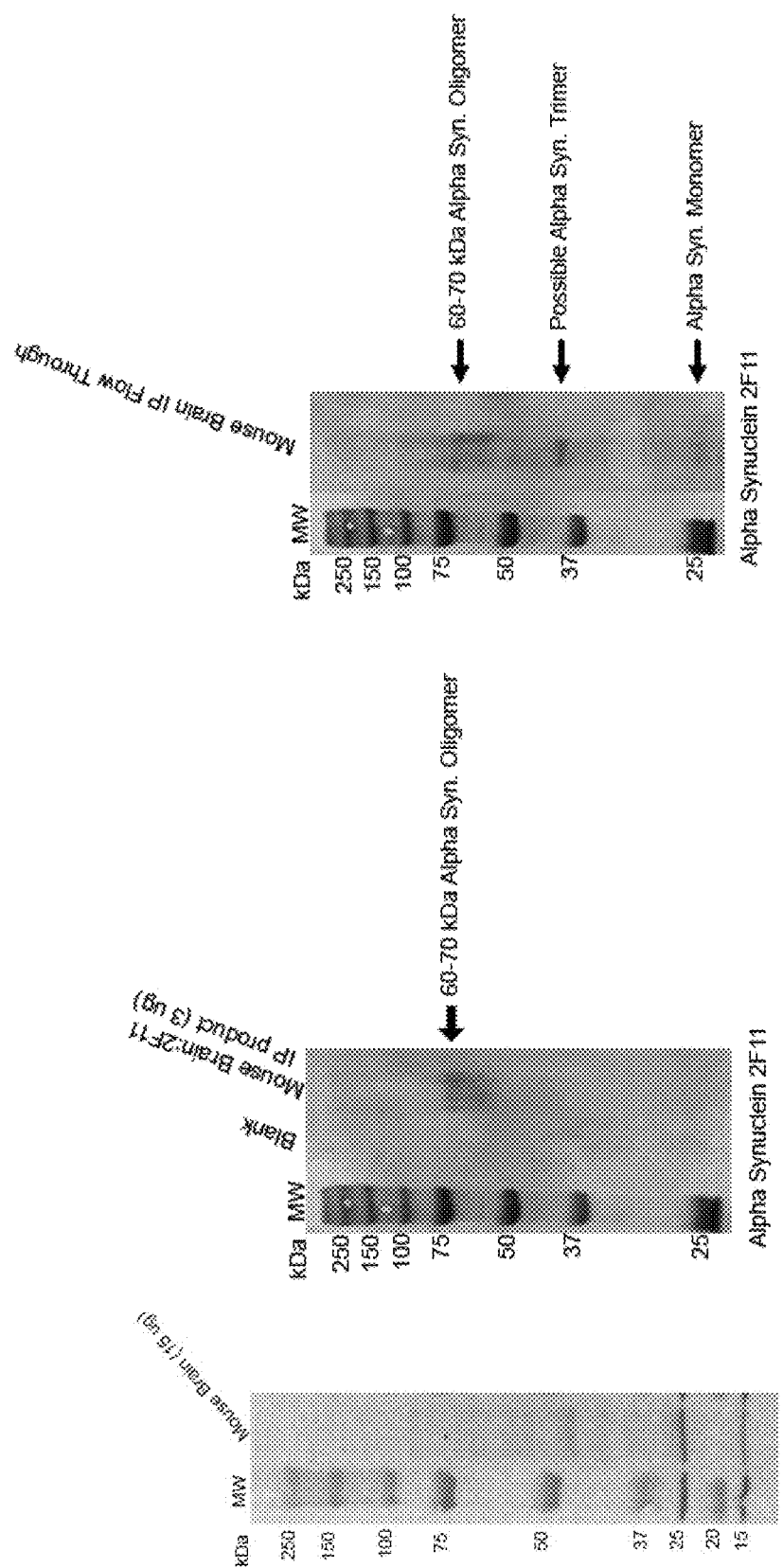

Selected Annotation from match P37840

Alignment

P37840

Ident.: 95.0%
Positives : 97.1%
Query Length: 140
Match Length: 140

```
O55042 SYUA_MOUSE    1   MDVFMKGLSKAKEGVVAAAEKTKQGVAEAAGKTKEGVLYVGSKTKEGVVHGVTTVAEKTK   60
                         MDVFMKGLSKAKEGVVAAAEKTKQGVAEAAGKTKEGVLYVGSK KEGVVHGV TVAEKTK
P37840 SYUA_HUMAN    1   MDVFMKGLSKAKEGVVAAAEKTKQGVAEAAGKTKEGVLYVGSKTKEGVVHGVATVAEKTK   60

O55042 SYUA_MOUSE   61   EQVTNVGGAVVTGVTAVAQKTVEGAGNIAAATGFVKKDQMGKGEEGYPQEGILEDMPVDP  120
                         EQVTNVGGAVVTGVTAVAQKTVEGAG+IAAATGFVKKDQ+G  EEG PQEGILEDMPVDP
P37840 SYUA_HUMAN   61   EQVTNVGGAVVTGVTAVAQKTVEGAGSIAAATGFVKKDQLGKNEEGAPQEGILEDMPVDP  120

O55042 SYUA_MOUSE  121   GSEAYEMPSEEGYQDYEPEA                                          140
                         +EAYEMPSEEGYQDYEPEA
P37840 SYUA_HUMAN  121   DNEAYEMPSEEGYQDYEPEA                                          140
```

FIG. 6

| Clone | 1-30 aa | 21-50 aa | 41-70 aa | 61-90 aa | 81-110 aa | 101-130 aa | 121-140 aa |
|---|---|---|---|---|---|---|---|
| 3D10 | | | ✓(DB-strong), ✓(ELISA-weak) | | | | ✓(WB-strong), ✓(DB-strong), ✓(ELISA-strong) |
| 3F8 | | | | ✓(ELISA-weak) | | ✓(WB-strong), ✓(DB-strong), ✓(ELISA-strong) | ✓(WB-strong), ✓(ELISA-strong) |
| 2F11 | | | | ✓(ELISA-weak) | | ✓(DB-weak), ✓(ELISA-strong) | |
| 1E9 | | | ✓(DB-weak), ✓(ELISA-weak) | ✓(ELISA-weak) | | ✓(ELISA-weak) | ✓(WB-strong), ✓(ELISA-strong) |
| 8C10 | | | | | | | ✓(ELISA-weak) |
| 4F1 | | ✓(DB)-weak | | ✓(DB-weak), ✓(ELISA-weak) | | ✓(DB-weak) | ✓(WB-weak), ✓(DB-weak) |
| 10H7 | | ✓(DB-weak) | | ✓(DB-weak) | | ✓(DB-strong), ✓(ELISA-strong) | |
| 7G2 | | ✓(DB-weak) | | | | ✓(DB-strong), ✓(ELISA-weak) | |
| 2G4 | ✓(ELISA-weak) | ✓(DB-weak) | | ✓(DB-strong) | | ✓(DB-strong) | |
| 10D6 (IgM) | | | | | | | |
| 5H7 (IgM) | | | | | | | |
| 8C2 (IgM) | ✓(ELISA-weak) | ✓(ELISA-weak) | ✓(ELISA-weak) | ✓(ELISA-strong) | ✓(ELISA-weak) | ✓(ELISA-strong) | ✓(ELISA-strong) |
| 3C11 (IgG-) | ✓(ELISA-strong) | | ✓(WB-weak), ✓(ELISA-strong) | | ✓(ELISA-strong) | ✓(ELISA-strong) | |
| 11F12 (IgG) | ✓(ELISA-strong), ✓(WB-weak), ✓(DB-weak) | ✓(ELISA-weak), ✓(WB-weak) | | | ✓(WB-strong), ✓(DB-strong), ✓(ELISA-strong) | ✓(WB-strong), ✓(DB-strong), ✓(ELISA-strong) | |
| 12G8 (IgG) | | | ✓(ELISA-weak), ✓(DB-weak) | | | ✓(ELISA-weak) | ✓(WB-strong), ✓(DB-strong), ✓(ELISA-strong) |

FIG. 10

2F11, heavy chain: nucleotide sequence (SEQ ID NO:10)

*ATGAAATGCAGCTGGGTCATCTTCTTCTTCCTGATGGCAGTGGTTATAGGAATCAATTCA*GAGGTTCAGCTGCAGCAGTCTGGGGCAGAGCTTGTGAGGTCAGGGGCCTC
AGTCAAGTTGTCCTGCACAGCTTCTGGCTTCAACATTAAAGACTACTATATGTTTGGGTGAAGCAGAGGCCTGAACAGGGCCTGGAGTGGATTGGATGGAATGATC
CTGAGAATGGTGATACTGAATATGCCCCGGAAGTTCCAGGGCAAGGCCACTATGACTGCAGATCCTCCAACAGACACATCCTCCAACACAGCCTACATCCAGCTCGACATCT
GAGGACACTGCCGTCTATTACTGTAATGCATGGGATGGTAACTATGTTATGGACTACTGGGGTCAAGGAACCTCAGTCACCGTCTCCTCA amino acid sequence (SEQ ID NO:11):

*MKCSWVIFFLMAVVIGINS*EVQLQQSGAELVRSGASVKLSCTASGFNIKDYYMFWVKQRPEQGLEWIGWNDPENGDTEYAPKFQGKATMTADTSSNTAYIQLSSLTS
EDTAVYYCNAWDGNYVMDYWGQGTSVTVSS

FIG. 11A

2F11, light chain: nucleotide sequence (SEQ ID NO:12)

*ATGGATTTTCAGGTGCAGATTTTCAGCTTCCTGCTAATCAGTGCCTCAGTCATAATGTCCAGAGGA*CAAATTGTTCTCACCCAGTCTCCAGCAATCATGTCTGCATC
TCTAGGGGAACGGGTCACCATGACCTGCACTGCCAGCTCAAGTGTAAGTTCCAGTTACTTGCACTGGTACCAGCAGAAGCCAGGATCCTCCCCCAAACTCTGGATTT
ATAGCACATCCAACCTGGCTTCTGGAGTCCCTGCTCGCTTCAGTGGCAGTGGGTCTGGGACCTCTTACTCTCTCACAATCAGCAGCATGGAGGCTGAAGATGCTGCC
ACTTATTACTGCCACCAGTATCATCGTTCCCCACCCATGTACACGTTCGGAGGGGGGACCAAGCTGGAAATAAAA amino acid sequence (SEQ ID NO:13)

*MDFQVQIFSFLLISASVIMSRG*QIVLTQSPAIMSASLGERVTMTCTASSSVSSYLHWYQQKPGSSPKLWIYSTSNLASGVPPRFSGSGSGTSY
SLTISSMEAEDAATYYCHQYHRSPPMYTFGGGTKLE

FIG. 11B

ANTIBODY BINDING ACTIVE α-SYNUCLEIN

CROSS-REFERENCE TO RELATED APPLICATIONS

This application continuation of U.S. patent application Ser. No. 16/635,943 filed on Jan. 31, 2020 entitled "ANTIBODY BINDING ACTIVE ALPHA-SYNUCLEIN," which claims priority to International Application No. PCT/CA2018/050952 filed on Aug. 2, 2018 entitled "ANTIBODY BINDING ACTIVE ALPHA-SYNUCLEIN," which claims priority to U.S. Provisional Patent Application No. 62/540,435 filed on Aug. 2, 2017, the disclosures of which are incorporated herein by reference.

FIELD OF INVENTION

The present invention relates to antibodies that bind α-synuclein. Also described are methods for using the antibodies.

BACKGROUND OF THE INVENTION

Parkinson's disease (PD) is neurodegenerative disorder that affects approximately 10 million people worldwide, with about 15% of them suffering from dementia with Lewy Bodies (DLB). These represent the core pathologies involving α-synuclein, a protein involved in the diseases although to date its main functions in the body remain largely unknown. The diseases themselves are characterized by a wide range of symptoms including the primary motor symptoms: resting tremors, bradykinesia, rigidity, postural instability, as well as non-motor symptoms including loss of sense of smell, constipation, REM behavior disorder, mood disorders and forgetfulness. Recently the aggregation of α-synuclein has also been shown to be involved in Multiple System Atrophy (MSA). In addition to Lewy bodies, the accumulation of the protein can result in Lewy neurites where axons and dendrites become elongated and dystrophic. The accumulation and eventual deposition of α-synuclein as aggregates that form Lewy bodies can be visualized as 10-20 μm inclusion bodies in neuronal tissue. In DLB these formations are widespread, leading to the symptoms associated with the disease.

Tau is a microtubule-associated protein that is involved in maintaining axonal transport and neuronal integrity and has a physiological role in dendrites. Tau is also expressed at low levels in glial cells. In the adult human brain, six isoforms of tau are expressed by alternative splicing from the MAPT gene. Mutations in the MAPT gene lead to hereditary diseases associated with the accumulation of pathological tau protein. Tauopathies are neurodegenerative diseases characterized by the deposition of abnormal tau protein in the brain. Neuropathological phenotypes comprise Alzheimer's disease, Pick's disease, progressive supranuclear palsy, corticobasal degeneration, frontotemporal dementia, argyrophilic grain disease, primary age-related tauopathy, formerly known as neurofibrillary tangle-only dementia, globular glial tauopathy (Kovacs, G. G, 2015, Neuropathol. App. Neurobiol., 41, 3-23). Alzheimer's disease is characterized by amyloid plaques and neurofibrillary tangles in the brain, with tau protein being the primary component of the tangles (Congdon, E. E., and Sigurdsson, E. M., Nat. Rev. Neurol., published on-line Jun. 12, 2018, Nature.com/nrneurol).

Traditionally, α-synuclein-containing Lewy bodies have been associated with Parkinson's disease and Tau-containing neurofibrillary tangles with Alzheimer's disease and various frontotemporal dementia syndromes. However, there is significant overlap and co-occurrence of α-synuclein and Tau pathologies in a spectrum of neurodegenerative diseases. For example, α-Synuclein aggregates (Lewy bodies) were found in a high percentage (60%) of familial and sporadic forms of Alzheimer's disease, while tau aggregates (Neurofibrillary tangles, NFTs) were observed in Parkinson's disease. Additionally, Lewy bodies and Neurofibrillary tangles were observed co-localize, since the proteins were found in each other's aggregation product in vivo (Li, X., et. al., 2016, J. Mol. Neurosci. 60:298-304).

Alpha-synuclein is known to directly bind tau and to induce fibrilization of tau (Benussi, L. et. el. 2005, Exp. Cell Res. 308:78-84; Li, X., et. al., 2016, J. Mol. Neurosci. 60:298-304). As a result, α-synuclein and Tau are proteins that are prone to pathological misfolding and aggregation. Misfolding initiates a homo-oligomerization and aggregation cascade culminating in cerebral accumulation of aggregated α-synuclein and Tau in insoluble protein inclusions in multiple neurodegenerative diseases. (Yan, X et. al., 2018 Seminars Cell Devel. Biol. available at URL: doi.org/10.1016/j.semcdb.2018.05.005).

Alpha-synuclein protein exists as three main isoforms, with the longest being 140 amino acids in length. It is a cytosolic protein, although small amounts are contained within vesicles, and can undergo exocytosis. This protein has been detected in blood and cerebrospinal fluid (Borghi et al., 2000; El-Agnaf et al., 2006; Kasuga et al., 2010). The extracellular α-synuclein may be involved in spreading the disease throughout the brain as well as cause neuronal death and inflammation (Desplats et al., 2009).

The process by which the α-synuclein becomes a disease-forming entity with prion-like properties is not well understood. Alpha-synuclein can take a complex path via an unknown number of intermediates and/or populations of intermediates from a monomeric, soluble protein with no prion-like activity to an insoluble aggregate with prion-like activity (see for example FIG. 1: Prior Art; Roberts H. L., Brown D. R., 2015, Biomolecules 5:282-305). The insoluble aggregate with prion-like activity is able to recruit soluble α-synuclein and change it into the aggregate by a process that includes a structural change from a helical conformation found on membranes and the cytosol (Bartels et al, 2011; Wang et al, 2011) to a β-sheet structure. However, the process of generating α-synuclein aggregates that are capable of recruiting monomers of the same protein and promoting their fibrillization starts with an unknown set of oligomer populations being formed.

A 12 amino acid peptide sequence in human alpha synuclein (residues 71 to 82; which are absent in β-synuclein) appear necessary and sufficient for fibrillization of the protein. This peptide is resistant to proteolysis, and it may become the core of α-synuclein filaments. Synthetic peptides that correspond to the 71-82 amino acid sequence are able to both self-polymerize into filaments and to co-assemble and promote assembly of full-length α-synuclein in vitro (Giasson et al., 2001). This peptide reversibly forms intermolecular β-sheets and demonstrates an equilibrium between the monomeric and oligomeric forms (Bédard et al., 2014). When in contact with anionic vesicles the peptide undergoes a conformational change that involves irreversible self-aggregation, mostly characterized by β-sheet formation. This mirrors structural and general properties of the native α-synuclein protein.

Membrane anionic vesicles show rapid formation of aggregates with the α-synuclein 71 to 82 peptide alone.

Furthermore, native α-synuclein can undergo misfolding or conformational change leading to oligomerization when interacting with membranes (Jo et al, 2000, Lee et al., 2002) and polyunsaturated fatty acids (Perrin et al., 2001). Helical α-synuclein can be converted directly into β-sheet containing fibrils on anionic phospholipid membranes (Comellas et al., 2012). A protocol to generate α-synuclein aggregates that are capable of recruiting monomers of the same protein (Volpicelli-Daley et al., 2014) has a disadvantage that small variations in rotor speeds, vial size and shape (containing the α-synuclein) can affect the size of bubbles formed within the vials, and therefore, the surface area available for the fibrillization process, interferes directly in the interfacial activation step. US 2004/0143093 teaches the use of specialized equipment and concentration-dependent hydrophobic interfaces to address issues associate with interfacial activation. Additionally, carboxy-terminal mutants of α-synuclein exhibit fibrillization under conditions where the native wild-type α-synuclein does not (Murray et al., 2003).

The extent to which α-synuclein fibrils are inherently toxic is not clear. Mature α-synuclein fibrils exist in a form of dynamic equilibrium with a population of oligomers generated by fibril assembly and disassembly. A heterogeneous mixture of oligomers (large and small) can form under near-physiological conditions (Cremades et al., 2012). When the fibrils disassemble, the products are able to seed growth of new fibrils in the presence of monomers. Fibril disassembly may occur in vivo during transmission of α-synuclein aggregates in cell culture (Desplats et al., 2009), and in synucleinopathy models (Hansen et al, 2011).

Prion-like activity may be caused by an oligomer population directly, or from an oligomer population created by fibril disassembly, for example, fibril breakage accelerates a-synuclein fibrillization (Shvadchak et al., 2015), and oligomer populations with different structures were either inhibitory towards a fibril formation or activating towards fibril formation (Horvath et al., 2013). These results suggest that oligomer populations may be "on the pathway" or "off the pathway", towards fibril assembly. Both on-pathway oligomer oligomers (Lashuel et al., (2002), Kostka et al., (2008), Zhang et al. (2013)), and off-pathway oligomers (Lorenzen et al., (2014), Cherny et al. (2005)) have been identified.

The process for making α-synuclein aggregates (also referred to as pre-formed fibrils or PPFs) for Lewy-body-based research (using the methods of Volpicelli-Daley et al., 2014), may reduce pre-existing oligomers of α-synuclein (Ariesandi et al., 2013) and results in uncertainty as to the level of toxic oligomer populations or aggregates in an α-synuclein aggregate preparation (versus other populations of oligomers or aggregates that are not toxic).

Polyclonal and monoclonal antibodies have been made against recombinant α-synuclein and partial peptides thereof, (Giasson, B. I. et al, 2000; Luk et al., 2009). Masliah et al., 2005, 2011 teach that active and passive immunization against α-synuclein with anti-α-synuclein antibodies reduced the deposition of α-synuclein and synaptic loss in a transgenic model of synucleinopathy. Bae et al (2012) showed that transmission of extracellular α-synuclein was reduced or stopped by immunizing with antibodies, and that this reduced transmission was predominantly carried out by microglia cells, providing a mechanism for clearance of the protein. In these studies, the antibodies (raised to recombinant monomeric human α-synuclein) were specific for linear sequences and identified denatured monomers. The antibodies were not binding structural, 3-dimension conformations of α-synuclein oligomers. For example, monoclonal antibody 274 (Bae et al, 2012) or 9E4 (and other monoclonal antibodies; Masliah et al. 2011), were observed to identify the linear sequence of α-synuclein in the aggregated form, as well as in monomers thereby not differentiating between the aggregate or monomeric forms of α-synuclein.

Lee et al. (2011) identified two monoclonal antibody clones 169 and 171 that had reduced affinity for denatured α-synuclein (in western blotting) and identified full length denatured recombinant α-synuclein.

U.S. Pat. No. 8,809,506 produced monoclonal antibodies against a mixture of chemically altered α-synuclein protofibrils and oligomers (chemically modified with 4-oxo-2-nonenal and 4-hydroxy-2-nonenal). The monoclonal antibodies were not tested to determine if they bound subpopulations of α-synuclein that were toxic, or if they bound linear or 3 dimensional epitopes generated by the multimer α-synuclein population that is toxic.

U.S. Pat. No. 8,940,276 teaches raising antibodies against α-synuclein. The antibodies were not able to differentiate between the toxic and non-toxic α-synuclein populations. Alpha-synuclein was identified as a monomer in a western blot, suggesting that the antibodies do not bind a 3-dimension epitope generated by toxic oligomers (which would be absent in SDS, reduced, boiled samples used in Western blot).

U.S. Pat. No. 9,084,832 characterizes antibodies to α-synuclein using ELISA techniques, which appear to have a higher affinity for a population of pre-fibrillar populations, but there is no indication if the α-synuclein populations are prion-like or toxic. Additionally, the antibody binds to specific short linear epitopes, rather than a 3-dimensional conformation specific to a (toxic) oligomer.

Ariesandi et al. (2013) teach that the heat-treatment inclusive process for making PPFs reduces pre-existing oligomer concentrations. This result further raises doubt as to whether the antibodies described in the above prior art target toxic populations of α-synuclein oligomers that are "on the pathway", or non-toxic oligomers that are "off the pathway".

The physiological function of the α-synuclein protein is not known. The toxicity of the protein is thought to be related to a sub-population of α-synuclein oligomers (rather than fibrils) that are not well defined in the literature. These sub-population types and concentrations are dynamic and thought to assemble and disassemble in vivo. There is a need to create an antibody that is able to bind the virulent, prion-like (toxic) form α-synuclein.

SUMMARY OF THE INVENTION

The present invention relates to antibodies that bind α-synuclein. Also described are methods for using the antibodies.

According to the present invention there is provided a monoclonal antibody, or an isolated monoclonal antibody, 2F11 that binds active α-synuclein, the monoclonal antibody produced by the hybridoma having accession number ATCC #PTA-124174 (received by the ATCC May 11, 2017). Also described herein is an isolated polynucleotide encoding the variable light chain, variable heavy chain, or both the variable light chain and the variable heavy chain of the monoclonal antibody produced by the hybridoma having accession number ATCC #PTA-124174, received May 11, 2017. Also provided is a composition or a vaccine comprising the monoclonal antibody 2F11 in a pharmaceutically acceptable carrier, adjuvant, vehicle or excipient is also described herein.

Also provided is method of reducing active α-synuclein, or tau fibrils, in a subject in need thereof comprising, administering an amount of the composition, or vaccine as described above to the subject. The composition or the vaccine may be administered to the subject orally, intranasally, intramuscularly, intraperitoneally, intravenously, or subcutaneously. If desired, prior to the step of administering, a level of active α-synuclein, or tau fibrils, in the subject may be determined, and after a period of time following the step of administering, one or more than one second level of active α-synuclein, or tau fibrils, may be determined.

Also described herein is a monoclonal antibody 2F11 that binds α-synuclein, tau fibrils, or a combination thereof, and comprises the following amino acid sequences that define the complementarity determining regions (CDRs):

```
Heavy chain:
                                    (SEQ ID NO: 14)
DYYMF;

(SEQ ID NO: 15)
WNDPENGDTEYAPKFQG;

(SEQ ID NO: 16)
NAWDGNYV;

Light chain:
                                    (SEQ ID NO: 17)
TASSSVSSSYLH (SEQ ID NO: 18)
STSNLAS (SEQ ID NO: 19)
HQYHRSPPMYT.
```

Also provided is a nucleic acid sequence that encodes the CDRs of monoclonal antibody 2F11 as defined by SEQ ID NO:14-19. For example, the nucleic acid sequence that encodes the CDRs of monoclonal antibody 2F11 may comprise the following nucleotide sequences:

```
Heavy chain:
                                    (SEQ ID NO: 20)
GACTACTATATGTTT (SEQ ID NO: 21)
TGGAATGATCCTGAGAATGGTGATACTGAATATGCCCCGAAGTTCCAGGGC (SEQ ID NO: 22)
AATGCATGGGATGGTAACTATGTT Light chain
                                    (SEQ ID NO: 23)
ACTGCCAGCTCAAGTGTAAGTTCCAGTTACTTGCAC (SEQ ID NO: 24)
AGCACATCCAACCTGGCTTCT (SEQ ID NO: 25)
CACCAGTATCATCGTTCCCCACCCATGTACACG
```

Also described herein is a monoclonal antibody, or an isolated monoclonal antibody, that binds to human α-synuclein, or tau fibrils, and comprises, a heavy chain variable region (VH) comprising three VH complementarily determining regions (CDRs) comprising the amino acid sequences set forth in SEQ ID NO's:14-16, and a light chain variable region (VL) comprising three VL CDRs comprising the amino acid sequences set forth in SEQ ID NO's:17-19, respectively. The amino acid sequences of the monoclonal antibody may be encoded by a nucleic acid sequence comprising one or more nucleotide sequences defined by SEQ ID NO'S:20-25. Furthermore, the monoclonal antibody is characterized as binding an α-synuclein active aggregate, or a tau aggregate, or a combination thereof. A composition or a vaccine comprising the monoclonal antibody as just described, in a pharmaceutically acceptable carrier, adjuvant, vehicle or excipient is also described herein.

Also described herein is an isolated polynucleotide sequence encoding CDRs of a monoclonal antibody a heavy chain variable region (VH) comprising three VH complementarily determining regions (CDRs) and comprising the amino acid sequences defined in SEQ ID NO's:14-16. An expression vector comprising the polynucleotide sequence is also described.

A multispecific antibody for transmigrating the blood brain barrier is also described herein. The multispecific antibody comprises one or more than one carrier molecule attached to the monoclonal antibody 2F11 produced by the hybridoma having accession number ATCC #PTA-124174 (received by the ATCC May 11, 2017). The multispecific antibody may be a trispecific or bispecific antibody for example a monovalent-bispecific antibody or a bivalent-bispecific antibody. Furthermore, the one or more than one carrier molecule of the multispecific or bispecific antibody may be derived from a transferin receptor (TfR)-binding antibody, or from an insulin-like growth factor 1 receptor (IGF1R)-binding antibody. A composition or a vaccine comprising the multispecific, trispecific or bispecific antibody as just described, in a pharmaceutically acceptable carrier, adjuvant, vehicle or excipient is also described herein.

Also provided is method of reducing active α-synuclein, or tau fibrils, in a subject in need thereof comprising, administering an amount of the composition, or vaccine as described above to the subject. The composition or the vaccine may be administered to the subject orally, intranasally, intramuscularly, intraperitoneally, intravenously, or subcutaneously. If desired, prior to the step of administering, a level of active α-synuclein, or tau fibrils, in the subject may be determined, and after a period of time following the step of administering, one or more than one second level of active α-synuclein, or tau fibrils, may be determined.

A method of determining the presence of active oligomeric α-synuclein in a sample is also described herein. The method comprises,
 i) pre-mixing a portion of the sample with a control antibody that does not bind active α-synuclein monomer followed by adding recombinant active α-synuclein monomer to produce a control treatment,
 ii) pre-mixing a second portion of the sample with the monoclonal antibody 2F11 (ATCC #PTA-124174, received May 11, 2017), followed by adding the recombinant active α-synuclein monomer to produce an active treatment,
 iii) determining the amount of β-sheet structure formation in both the control treatment and the active treatment using a Thioflavin assay, wherein a decrease in Thioflavin fluorescence in the active treatment, when compared with the control treatment, is indicative of the presence of the active oligomeric α-synuclein in the sample.

A method for determining the presence of tau aggregation in a sample is provided. The method comprising:
 i) pre-mixing a portion of the sample with a control antibody followed by adding tau monomer to produce a control treatment, ii) pre-mixing a second portion of the sample with the monoclonal antibody 2F11 (ATCC #PTA-124174), followed by adding the tau monomer to produce an active treatment, and iii) determining the amount of β-sheet structure formation in both the control treatment and the active treatment. Wherein a decrease in the amount of β-sheet structure formation in the active treatment, when compared with the control treatment, is indicative of the presence of the tau aggregation in the sample.

An alternate method of determining the presence of active oligomeric α-synuclein in a sample is also described. The method comprising, exposing the sample to the monoclonal antibody 2F11 (ATCC #PTA-124174, received May 11, 2017), and determining if the monoclonal antibody 2F11 binds to protein in the sample, wherein binding is indicative of the presence of the active oligomeric α-synuclein. The sample may be separated using non-denaturing electrophoresis prior to the step of exposing, and the separated protein is probed using the monoclonal antibody 2F11 via western analysis, wherein binding of one or more high molecular weight protein is indicative of the presence of the active oligomeric α-synuclein in the sample. Alternatively, a dot blot of the non-denatured sample may be probed using the monoclonal antibody 2F11, and binding of the monoclonal antibody 2F11 to the sample is indicative of the presence of the active oligomeric α-synuclein.

A method of determining the presence of tau aggregation in a sample is also described. The method comprising, exposing the sample to the monoclonal antibody 2F11 (ATCC #PTA-124174, received May 11, 2017), and determining if the monoclonal antibody 2F11 binds to protein in the sample, wherein binding is indicative of the presence of the tau aggregation. The sample may be separated using non-denaturing electrophoresis prior to the step of exposing, and the separated protein is probed using the monoclonal antibody 2F11 via western analysis, wherein binding of one or more high molecular weight protein is indicative of the presence of the active oligomeric α-synuclein in the sample. Alternatively, a dot blot of the non-denatured sample may be probed using the monoclonal antibody 2F11, and binding of the monoclonal antibody 2F11 to the sample is indicative of the presence of the tau aggregation.

An additional method for determining the presence, concentration, or both the presence and concentration, of an active oligomeric α-synuclein in a sample is provided. The method comprises applying a sample to a surface that has been prepared using the monoclonal antibody 2F11 (ATCC #PTA-124174) and determining an occurrence, an amount, or an occurrence and an amount, of the active α-synuclein aggregate that is bound to the monoclonal antibody, thereby determining the presence, concentration, or both the presence and concentration, of the active α-synuclein aggregate in the sample.

A method for determining the presence, concentration, or both the presence and concentration, of a tau aggregation in a sample is also provided. The method comprises applying a sample to a surface that has been prepared using the monoclonal antibody 2F11 (ATCC #PTA-124174) and determining an occurrence, an amount, or an occurrence and an amount, of the tau aggregation that is bound to the monoclonal antibody, thereby determining the presence, concentration, or both the presence and concentration, of the tau aggregation in the sample.

A method of inducing an immune response in a subject that has been diagnosed with a synucleinopathy, a pathological condition characterized by Lewy bodies, Parkinson's disease, dementia with Lewy bodies, multiple system atrophy, sporadic Alzheimer's disease, or familial Alzheimer's disease, a taupathy, a pathological condition characterized by Neurofibrillary tangles, Alzheimer's disease, Pick's disease, progressive supranuclear palsy, corticobasal degeneration, frontotemporal dementia, argyrophilic grain disease, primary age-related tauopathy, neurofibrillary tangle-only dementia, globular glial tauopathy, is also described. The method comprises administering the monoclonal antibody 2F11 as defined above, the pharmaceutical composition comprising the monoclonal 2F11, or the multispecific, trispecific, or bispecific antibody comprising 2F11, to the subject.

Also disclosed herein is a method of treating a synucleinopathy, a pathological condition characterized by Lewy bodies, Parkinson's disease, dementia with Lewy bodies, multiple system atrophy, sporadic Alzheimer's disease, or familial Alzheimer's disease, a taupathy, a pathological condition characterized by Neurofibrillary tangles, Alzheimer's disease, Pick's disease, progressive supranuclear palsy, corticobasal degeneration, frontotemporal dementia, argyrophilic grain disease, primary age-related tauopathy, neurofibrillary tangle-only dementia, globular glial tauopathy, comprising administering the monoclonal antibody 2F11 as defined above, the pharmaceutical composition comprising the monoclonal antibody 2F11, or the multispecific, trispecific, or bispecific antibody comprising 2F11, to the subject.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 3A shows a Western blot analysis of mouse brain lysate probed with clone 2F11. Left lane: marker (kDa); right lane clone 2F11. A high molecular weight band in the mouse brain lysate was identified using clone 2F11. FIG. 3B shows a Western blot analysis of mouse brain lysate probed with clone 4F1. Left lane: marker (kD); right lane clone 4F1. A low molecular weight band in the mouse brain lysate was identified using clone 4F1. FIG. 3C shows a Western blot of mouse brain lysate probed with clone 3F8. Left lane: marker (kDa); right lane clone 3F8. A low molecular weight band in the mouse brain lysate was identified using clone 3F8.

FIG. 4 shows a protein stain of the mouse brain lysate used in FIG. 3A-3C. Left lane: marker (kDa), right lane Ponceau staining of the mouse brain lysate.

FIG. 5A shows a Western blot analysis of immune precipitated mouse brain lysate probed using clone 2F11. An oligomeric band of α-synuclein of approx. 60-70 kDa is indicated. Left lane: marker (kDa); middle lane: blank; right lane: mouse brain lysate. FIG. 5B shows a Western blot analysis of the flow through from immune precipitated mouse brain lysate probed using clone 2F11. An oligomeric band of α-synuclein of approx. 60-70 kDa, a trimeric band of α-synuclein and a monomeric band of α-synuclein are indicated. Left lane: marker (kDa); right lane: mouse brain lysate.

FIG. 6 shows a nucleic acid sequence alignment of mouse α-synuclein (top sequence; 055043; SEQ ID NO:1) and human α-synuclein (bottom sequence; P37840; SEQ ID NO:2).

FIG. 10 shows binding of various antibodies with overlapping peptides of α-synuclein. Peptides: 1-30aa (SEQ ID NO:3); 21-50aa (SEQ ID NO:4); 41-70aa (SEQ ID NO:5); 61-90 aa (SEQ ID NO:6); 81-100 aa (SEQ ID NO:7); 101-130 aa (SEQ ID NO:8); 121-140 (SEQ ID NO:9). Binding determined using ELISA, dot blot (DB), and/or Western blot (WB) analysis.

FIG. 11A shows the consensus nucleic acid sequence (SEQ ID NO:10) and the amino acid sequence (SEQ ID NO:11) of the variable region (heavy chain—IgG1 isotype) of for 2F11. FIG. 11B shows the consensus nucleic acid sequence (SEQ ID NO:12) and the amino acid sequence (SEQ ID NO:13) of the light chain variable region (Kappa) of for 2F11. Complementarity determining regions (CDRs) are underlined; leader sequence is identified in italics.

DETAILED DESCRIPTION

The following description is of a preferred embodiment.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

As used herein, a "protein level" or "level of active protein" refers to an amount, or a relative amount, of the protein in a sample, a sample obtained from a subject, or a in a subject. The protein level may be compared to a reference or control protein level to determine a status of the sample. A subject's protein level can be either in absolute amount for example, nanogram/ml or microgram/ml, or it may be expressed as a relative amount for example, a relative intensity of a signal when compared to a control level; a percent or "fold" or "fold-change" increase when compared to a control protein level.

In a similar manner, an "expression level" of a transcript in a subject refers to an amount of transcript in a subject's undiagnosed biological sample. The expression level may be compared to a reference expression level to determine a status of the sample. A subject's expression level can be either in absolute amount (e.g., nanogram/ml or microgram/ml) or a relative amount (e.g., relative intensity of signals; a percent or "fold" or "fold-change" increase).

Figure 1:
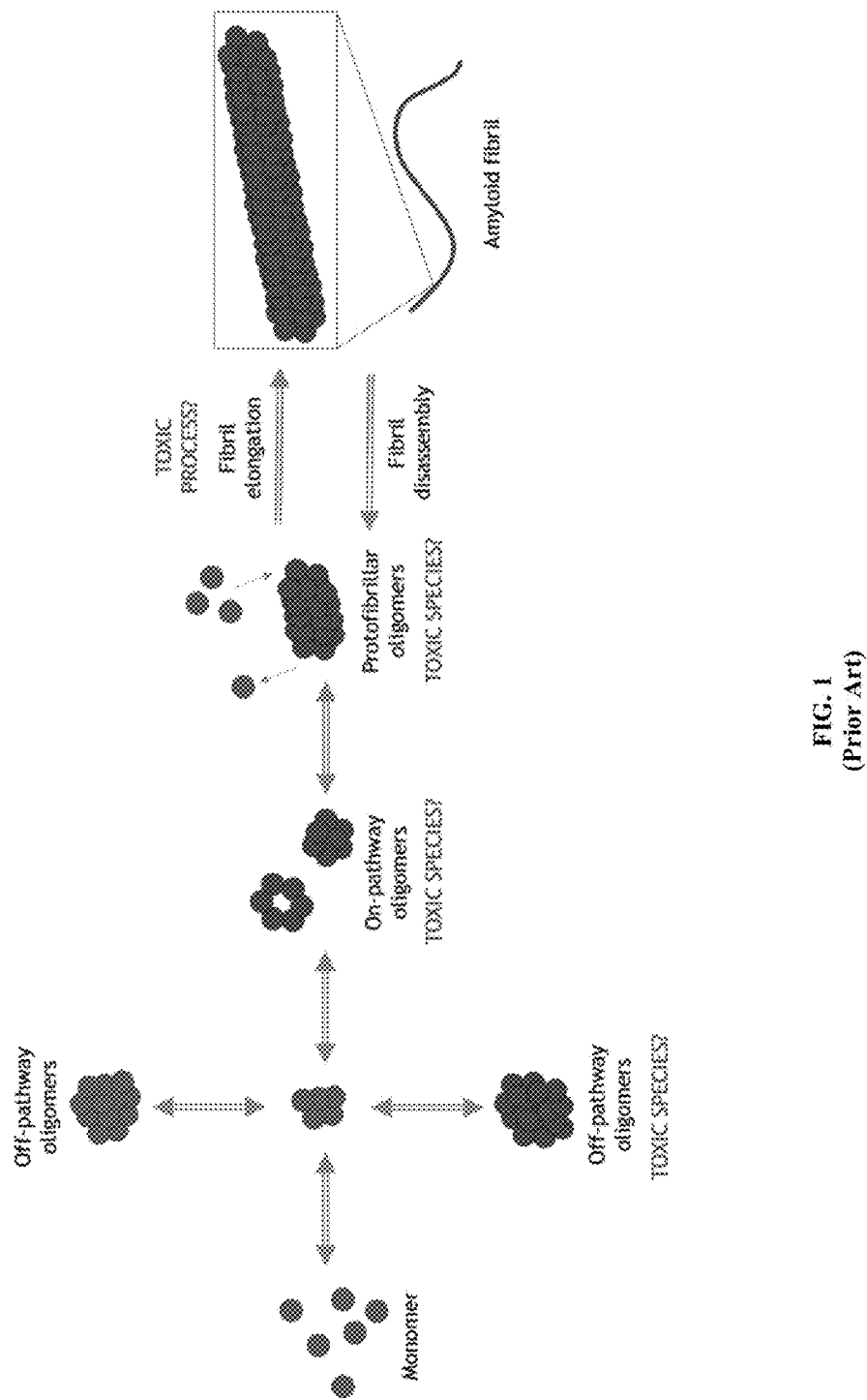
FIG. 1 shows a pathway leading to amyloid fibril formation from "on the pathway" toxic α-synuclein monomers. Prior Art (Roberts H. L., Brown D. R., 2015, Biomolecules 5:282-305; also available at URL: mdpi.com/2218-273X/5/2/282).

As shown in FIG. 1, α-synuclein can take a complex path via an unknown number of intermediates and/or populations of intermediates from a monomeric, soluble protein with no prion-like activity to an insoluble aggregate with prion-like activity (see for example FIG. 1: Prior Art; Roberts H. L., Brown D. R., 2015, Biomolecules 5:282-305, which is incorporated herein by reference). The insoluble aggregate with prion-like activity is able to recruit soluble α-synuclein and seed the α-synuclein aggregation process.

Examples of a disease or pathological condition associated with α-synuclein fibril formation, or synucleinopathies, include but are not limited to, a pathological condition characterized by Lewy bodies, such as Parkinson's disease, dementia with Lewy bodies, multiple system atrophy, sporadic Alzheimer's disease, and familial cases with Alzheimer's disease. Examples of a disease or pathological condition associated with tau fibril formation, or tauopathies, include but are not limited to, a pathological condition characterized by Neurofibrillary tangles, Alzheimer's disease, frontotemporal dementia, progressive supranuclear palsy, corticobasal degeneration, Parkinson's disease, Pick's disease, argyrophilic grain disease, primary age-related tauopathy, neurofibrillary tangle-only dementia, and globular glial tauopathy.

A "species of α-synuclein monomer", or an "α-synuclein monomer species" includes the group of an α-synuclein monomer (which may also be termed a non-active or inactive α-synuclein monomer), and an active α-synuclein monomer (may also be termed a toxic α-synuclein monomer).

A "species of α-synuclein oligomer" or an "α-synuclein oligomer species" includes a non-active α-synuclein oligomer (also termed "off-pathway" oligomer), an active α-synuclein oligomer, or toxic α-synuclein oligomer (also termed "on-pathway" α-synuclein oligomer).

A "non-active α-synuclein monomer", or "an inactive α-synuclein monomer" refers to non-toxic monomer of α-synuclein. A mixture of α-synuclein monomers do not combine to form active an α-synuclein oligomer. However, a mixture of α-synuclein monomer (inactive) and active α-synuclein monomer may combine to form an active α-synuclein oligomer.

An "active α-synuclein species" refers to one or more than one of an active α-synuclein monomer, a toxic α-synuclein monomer, an active α-synuclein aggregate, a toxic α-synuclein aggregate, an active α-synuclein oligomer, a toxic α-synuclein oligomer, an on-pathway oligomer, a β-sheet structure comprising α-synuclein, an α-synuclein fibril.

As used herein, an "active α-synuclein monomer", or a "toxic α-synuclein monomer" refers to a species of an α-synuclein monomer that when combined with other active α-synuclein monomers, or active α-synuclein aggregates, results in the formation of an active or toxic α-synuclein oligomer, the formation of a β-sheet structure comprising α-synuclein, an active or toxic α-synuclein aggregate, or an α-synuclein fibril. An active α-synuclein monomer is capable of combining with other active α-synuclein oligomers, active α-synuclein aggregates, or a combination thereof, and proceed along the pathway of amyloid fibril formation.

As used herein an "active oligomeric α-synuclein", a "toxic α-synuclein oligomer", or an "on-pathway α-synuclein oligomer" refers to population of α-synuclein monomers that have the ability of recruiting an active α-synuclein monomer or an active aggregate to produce protofibrillar oligomers, which can elongate and produce α-synuclein fibrils (amyloid fibrils; see FIG. 1).

An "active aggregate" or an "active α-synuclein aggregate" may be used interchangeably with "pre-formed fibrils" (PFFs). PFFs or active aggregates refer to a collection of active α-synuclein oligomers, pre-fibrils comprising two or more active α-synuclein oligomers, fibrils comprising two or more active α-synuclein oligomers, or a combination thereof. PFFs, or active aggregates, may be used to seed a reaction (see for example FIGS. 2B, 9B-9D). Active α-synuclein aggregates have more β-sheet content and less α-helix than "inactive aggregates" (see Table 1; Example 2).

An "inactive aggregate" is used to refer to a collection of inactive α-synuclein oligomers, pre-fibrils comprising inactive α-synuclein oligomers, fibrils comprising inactive α-synuclein oligomers, or a combination thereof. Inactive aggregates do not form β-sheets (see FIG. 2), and they do not seed a reaction (see for example FIG. 2B, 9B-9D).

The percent identify (or percent similarity) between the amino acid mouse and human α-synuclein is 95% (see FIG. 6).

The terms "percent similarity", "sequence similarity", "percent identity", or "sequence identity", when referring to a particular sequence, are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Natl. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and proteins of the invention. For example, the BLASTN program (for nucleotide sequences) may use as defaults a wordlength (W) of 11, an expectation (E) of 10, M=5, N=−4 and a comparison of both strands. For amino acid sequences, the BLASTP program may use as defaults a word length of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands. Software for performing BLAST analyses is publicly available through the National Center for Biotechnology Information (see URL: ncbi.nlm.nih.gov/).

A "reference level", a "reference protein level", or a "control protein level", as used herein refers to an amount of α-synuclein or a range of amounts of α-synuclein protein measured in a normal individual or in a population of individuals without any indication of having a disease state or pathological condition associated with α-synuclein fibril formation in a subject, for example a pathological condition characterized by Lewy bodies, for example but not limited to, Parkinson's disease. For example, a reference level of one or more than one active species of α-synuclein, for example, an active α-synuclein monomer, or an active oligomeric α-synuclein, may be determined based on the level or amount of α-synuclein (an active α-synuclein monomer or an active oligomeric α-synuclein) identified in samples obtained from one or more than one normal individual. A reference level can be either in absolute amount (e.g., nanogram/ml or microgram/ml) or a relative amount (e.g., relative intensity of signals; a percent or "fold" or "fold-change" increase when compared to a control level or amount).

As used herein, a "threshold level", "threshold amount", or "threshold expression level" refers to an amount or a level of α-synuclein in a biological sample that is between about a 1.5 fold-change and about a 20 fold-change, or any amount therebetween, over a reference amount or level of one or more than one active α-synuclein species, an active α-synuclein monomer or an active oligomeric α-synuclein, for example, when compared to the level or amount of α-synuclein identified in a control sample or a control subject. A threshold level of α-synuclein may be indicative of a disease state that associated with α-synuclein fibril formation, a pathological condition characterized by Lewy bodies, for example but not limited to, Parkinson's disease.

As used herein, a "baseline level" refers to an amount or a level of α-synuclein in a first biological sample obtained from a subject that is determined prior to any treatment or during any treatment and is used as comparison to a second expression level of α-synuclein that is assessed from a second biological sample that is obtained from the subject at a time after the first biological sample is obtained. This baseline level may be used, for example, in monitoring the progression of a disease state or pathological condition associated with α-synuclein fibril formation in a subject, for example a pathological condition characterized by Lewy bodies, for example but not limited to, Parkinson's disease, monitoring a treatment regimen or treatment modality in a subject having a disease state or pathological condition associated with α-synuclein fibril formation, determining whether a treatment regimen or treatment modality should be considered in a subject, determining whether a treatment regimen or treatment modality should be discontinued in a subject, or determining whether a treatment regimen or treatment modality should be modified in a subject.

As used herein, "normal individual" refers to an individual that has been tested for α-synuclein fibril formation using a combination of one or more diagnostic methods as described herein (including Thioflavin assay, Western analysis, ELISA, or dot blot analysis), and determined to not have any active α-synuclein monomers or active oligomeric α-synuclein.

The terms "therapy," and "treatment," as used interchangeably herein, refer to an intervention performed with the intention of improving a recipient's status. The improvement can be subjective or objective and is related to the amelioration of the symptoms associated with, preventing the development of, or altering the pathology of a disease, disorder or pathological condition being treated. Thus, the terms therapy and treatment are used in the broadest sense, and include the prevention (prophylaxis), moderation, reduction, and curing of a disease, disorder or pathological condition at various stages. Prevention of deterioration of a recipient's status is also encompassed by the term. Those in need of therapy/treatment include those already having the disease, disorder or condition as well as those prone to, or at risk of developing, the disease, disorder or condition and those in whom the disease, disorder or pathological condition is to be prevented. In the context of the present invention, the disease, disorder or pathological condition is associated with:

α-synuclein fibril formation, or synucleinopathies, including but not limited to, a pathological condition characterized by Lewy bodies, such as Parkinson's disease, dementia with Lewy bodies, multiple system atrophy, sporadic Alzheimer's disease, and familial cases with Alzheimer's disease, tau fibril formation (aggregation), or taupathies, including but not limited to a pathological condition characterized by Neurofibrillary tangles, Alzheimer's disease, Pick's disease, progressive supranuclear palsy, corticobasal degeneration, frontotemporal dementia, argyrophilic grain disease, primary age-related tauopathy, neurofibrillary tangle-only dementia, and globular glial tauopathy, or a combination thereof.

The term "subject" or "patient," as used herein, refers to a mammal, for example, the subject may be a human. Alternatively, the subject may be a non-human primate, a domestic animal or an agricultural animal.

The term "effective amount" as used herein refers to an amount of a compound that produces a desired effect. For example, a population of cells, or a cell extract, may be contacted with an effective amount of a compound to study its effect in vitro or to produce a desired therapeutic effect ex vivo or in vitro. An effective amount of a compound may be used to produce a therapeutic effect in a subject, such as preventing or treating a target condition, alleviating symptoms associated with the condition, or producing a desired physiological effect. In such a case, the effective amount of a compound is a "therapeutically effective amount," "therapeutically effective concentration" or "therapeutically effective dose." The effective amount or therapeutically effective amount is an amount of the composition that will yield the most effective results in terms of efficacy of treatment in a given subject. This amount will vary depending upon a variety of factors, including but not limited to the characteristics of the compound (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Non-limiting examples of suitable carriers include a buffer, a stabilizing agent, a salt, an antioxidant, a complexing agent, a cryoprotectant, a lyoprotectant, a suspending agent, an emulsifying agent, an antimicrobial agent, a preservative, a chelating agent, a binding agent, a surfactant, a wetting agent, a non-aqueous vehicle such as an oil, or a polymer for sustained or controlled release. See, for example, Berge et al. 1977 (J. Pharm Sci. 66:1-19). Further an effective or therapeutically effective amount may vary depending on whether the compound is administered alone or in combination with another compound, drug, therapy or other therapeutic method or modality. One skilled in the clinical and pharmacological arts will be able to determine an effective amount or therapeutically effective amount through routine experimentation, namely by monitoring a cell's or subject's response to administration of a compound and adjusting the dosage accordingly. For additional guidance, see for example Remington: The Science and Practice of Pharmacy, 21st Edition, Univ. of Sciences in Philadelphia (USIP), Lippincott Williams & Wilkins, Philadelphia, Pa., 2005, which is hereby incorporated by reference as if fully set forth herein.

A "biological sample" or "sample" refers to any material, biological fluid, tissue, or cell obtained or otherwise derived from a subject including, but not limited to, blood (including whole blood, leukocytes, peripheral blood mononuclear cells, plasma, and serum), cerebral spinal fluid, a tissue extract, and a cellular extract. This also includes experimentally separated fractions of all of the preceding. For example, a blood sample can be fractionated into serum or into fractions containing particular types of blood cells, such as red blood cells or white blood cells (leukocytes). If desired, a sample may be a combination of samples from an individual, such as a combination of a tissue and fluid sample. A biological sample may also include materials containing homogenized solid material, such as from a tissue sample, or a tissue biopsy; or materials derived from a tissue culture or a cell culture. Tissue may be normal tissue or diseased tissue.

Inactive and active α-synuclein monomers and aggregates were evaluated to determine if the soluble monomers and insoluble aggregates were active (prion-like) and able to seed, or be seeded by, the α-synuclein aggregation process (as determined by β-sheet structure formation). As shown in FIG. 2 (Example 2):

a. inactive α-synuclein monomers, inactive aggregates, or inactive α-synuclein monomers combined with active α-synuclein aggregates were not able to seed the aggregation process and no β-sheet structure formation was observed;

b. active monomers, or active monomers combined with inactive aggregates were able to self-seed, and active monomers and active aggregates (or pre-formed fibrils; PFFs), were able to seed the prion-like aggregation reaction and an increase in β-sheet structure formation was observed.

Mouse monoclonal antibodies were prepared against the active α-synuclein aggregates and active α-synuclein monomers. Hybridomas secreting antibodies to the active form of the α-synuclein monomer, but not the inactive version, were selected. Using Western blot analysis, one antibody, 2F11 (ATCC #PTA-124174, received May 11, 2017) was observed to identify a high molecular weight α-synuclein aggregate in mouse brain lysate and HeLa lysate (>150 kDa; see FIGS. 3A and 3D), while other α-synuclein monoclonal antibodies (also selected by binding the active form of α-synuclein monomer), only identified a 15 kDa band (4F1, FIG. 3B; 3F8, FIG. 3C).

The nucleic acid and amino acid sequences of the heavy (SEQ ID NO's: 10 and 11) and light (SEQ ID NO's: 12 and 13) chains of 2F11 are provided in FIGS. 11A and 11B. The monoclonal antibody 2F11 comprises the following amino acid sequences that define the complementarity determining regions (CDRs):

```
Heavy chain:
                                      (SEQ ID NO: 14)
DYYMF;

(SEQ ID NO: 15)
WNDPENGDTEYAPKFQG;

(SEQ ID NO: 16)
NAWDGNYV;

Light chain:
                                      (SEQ ID NO: 17)
TASSSVSSSYLH (SEQ ID NO: 18)
STSNLAS (SEQ ID NO: 19)
HQYHRSPPMYT.
```

The nucleic acid sequence that encodes the CDRs of monoclonal antibody 2F11 comprise the following nucleotide sequences:

```
Heavy chain:
                                      (SEQ ID NO: 20)
GACTACTATATGTTT (SEQ ID NO: 21)
TGGAATGATCCTGAGAATGGTGATACTGAATATGCCCCGAAGTTCCAGGGC
```

-continued

AATGCATGGGATGGTAACTATGTT (SEQ ID NO: 22)

Light chain
ACTGCCAGCTCAAGTGTAAGTTCCAGTTACTTGCAC (SEQ ID NO: 23)

AGCACATCCAACCTGGCTTCT (SEQ ID NO: 24)

CACCAGTATCATCGTTCCCCACCCATGTACACG. (SEQ ID NO: 25)

The monoclonal antibody 2F11 binds α-synuclein oligomers but not α-synuclein monomers (active) under native gel electrophoresis conditions from native samples. Brain lysate (obtained from mouse) was immunoprecipitated under native conditions using 2F11, and the precipitate and the flow through fractions were analyzed using denaturing Western blot. The 2F11 antibody bound α-synuclein oligomers (running at 60-70 kDa once denatured) in the immunoprecipitated native brain lysate, but did not bind α-synuclein monomer (active), demonstrating that no monomeric band was immunoprecipitated by 2F11 from the native sample (FIG. 5A). However, three fractions of the flow through fraction were observed to bind 2F11 when this fraction was separated under denaturing conditions: α-synuclein monomer (active) of approx. 15 kDa; a putative α-synuclein trimer of approx. 40 kDa; and α-synuclein oligomer 60-70 kDa (FIG. 5B), demonstrating that under denaturing conditions (as used during Western blot analysis) 2F11 is able to bind both stabilized oligomers and monomeric α-synuclein. Since 2F11 selectively binds tau aggregates (see FIG. 13), this approach may also be used to determine the presence of tau aggregates.

Figure 7:
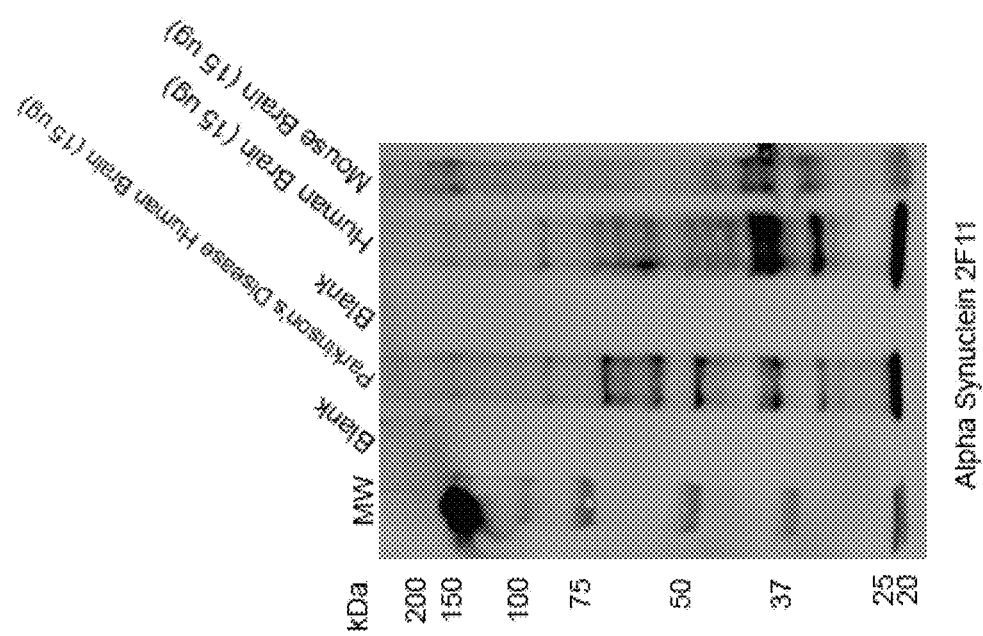
FIG. 7 shows a Western blot analysis of denatured samples obtained from Parkinson's disease human brain, human brain and mouse brain, probed using clone 2F11. From left to right: marker kDa; human brain with Parkinson disease; human control; mouse brain. Multiple bands over a range of molecular weights, including high molecular weights, are present in human brain with and without Parkinson's disease and mouse samples.
Figure 8B:
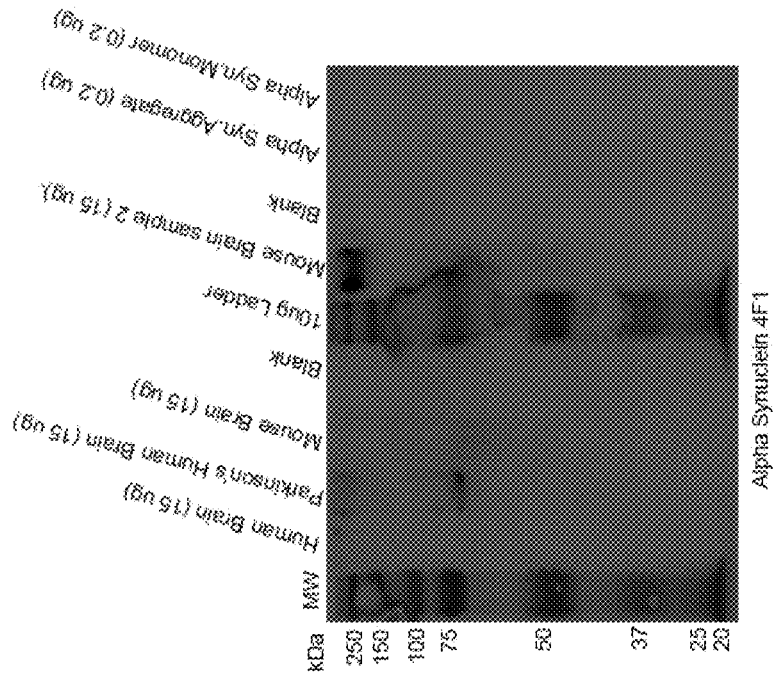
FIG. 8B shows a native Western analysis of samples obtained from Parkinson's disease human brain, human brain and mouse brain, probed using clone 4F1. From left to right: marker kDa; human brain (control); human brain with Parkinson's disease; mouse brain; blank; marker kDa; mouse brain (sample 2); blank; α-synuclein aggregate (active); α-synuclein monomer (active). Lysate of mouse brain and mouse brain 2 were from different source and prepared using the same method.
Figure 8A:
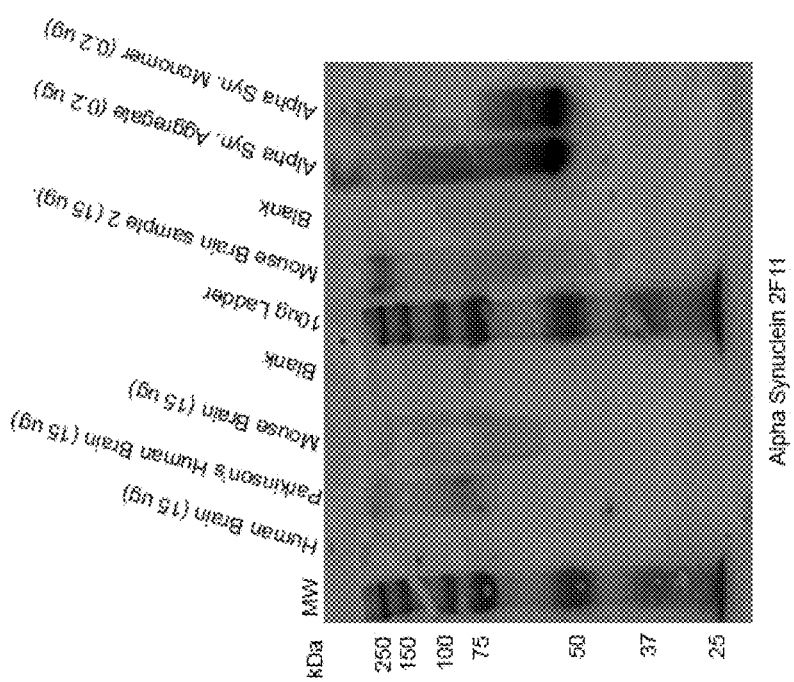
FIG. 8A shows a native Western analysis of samples obtained from Parkinson's disease human brain, human brain and mouse brain, probed using clone 2F11. From left to right: marker: kDa; Human brain (control); human brain with Parkinson's disease; mouse brain; blank; marker kDa; mouse brain (sample 2); blank; α-synuclein aggregate (active); α-synuclein monomer (active).

The mouse monoclonal antibody 2F11 was observed to bind human α-synuclein in lysates from human brain, lysates from human brain from a Parkinson's patient, and lysate from a mouse brain, using Western blot analysis under denaturing (FIG. 7), or native conditions (FIGS. 8A and 8B). For example, 2F11 bound high and mid molecular weight human and mouse α-synuclein oligomers under denaturing conditions (FIG. 7). Under native, non-reducing, conditions (FIG. 8A), 2F11 bound high molecular weight α-synuclein oligomers from human brain lysates, Parkinsons brain lysate, and mouse brain lysate, of approx. 60 kDa to about 250 kDa. Therefore, 2F11 identifies α-synuclein oligomers or aggregates under native conditions.

The 4F1 antibody was also observed to bind higher molecular weight oligomers under native conditions (FIG. 8B). However, 4F1 did not recognize purified pathogenic (active) α-synuclein monomers or aggregates.

Therefore, in a native system 2F11 identifies both human and mouse α-synuclein, but the 2F11 antibody does not bind α-synuclein monomer (active). Without wishing to be bound by theory, these results indicate that 2F11 binds α-synuclein aggregates allowing it to bind pathogenic species of α-synuclein oligomers, or an oligomer directly involved in the pathway to creating Lewy Body pathology.

Since 2F11 was able to bind both human and mouse α-synuclein, and since the percent identify (or percent similarity) of the amino acid between mouse and human α-synuclein is 95% (FIG. 6), 2F11 is able to identify α-synuclein having from about 95 to about 100%, or any amount therebetween, sequence similarity with the amino acid sequence of SEQ ID NO:1 or SEQ ID NO:2. For example, 2F11 may identify α-synuclein having from 90, 91, 92, 93, 94, 95, 96, 97, 98, 99, 100%, or any amount there between, sequence similarity with the amino acid sequence of SEQ ID NO:1 or SEQ ID NO:2, as determined under native or denatured conditions as described herein.

Figure 9A:
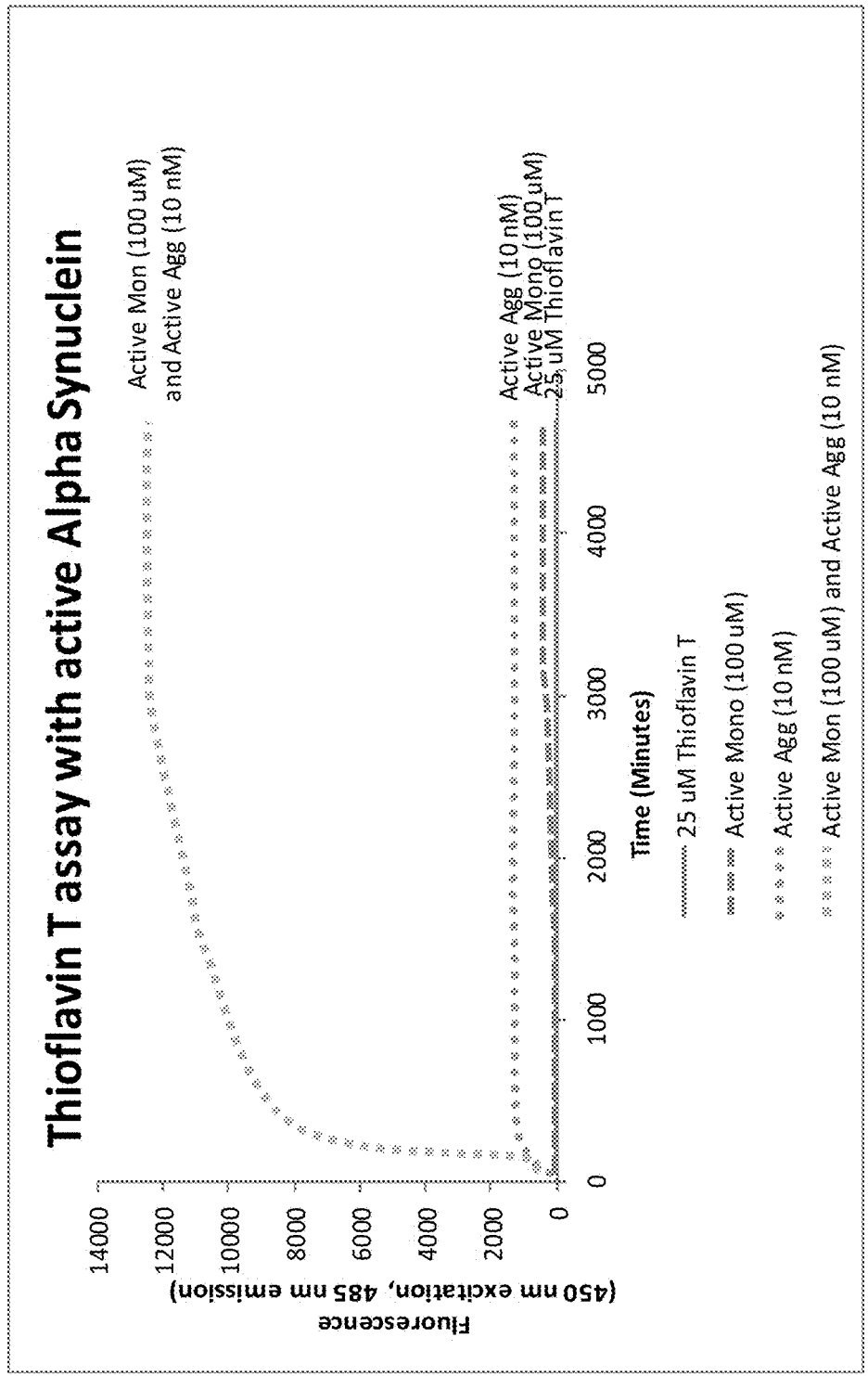
FIG. 9A shows a time course of the Thioflavin activity assay. Samples (from top to bottom): α-synuclein active monomer (100 µM)+active aggregate (10 nM); α-synuclein active aggregate (10 nM); α-synuclein active monomer (100 µM); Thioflavin control (25 µM).

The monoclonal antibody 2F11 was also observed to block β-sheet structure formation in vitro. Progression of the α-synuclein reaction may be determined as shown in FIG. 9A. In this assay, in the presence of an active α-synuclein aggregate an active α-synuclein monomer is "seeded", and changes from an alpha helical structure to beta sheet over time (i.e. an increase in Thioflavin fluorescence is observed; (top line). Active α-synuclein aggregates resulted in a slight increase in β-sheet structure formation (second from top line) but this increase is less than that of the mixture of an active α-synuclein aggregate combined with an active α-synuclein monomer (top line). Active α-synuclein monomers can slowly self-seed over time (third line from top).

Figure 9B:
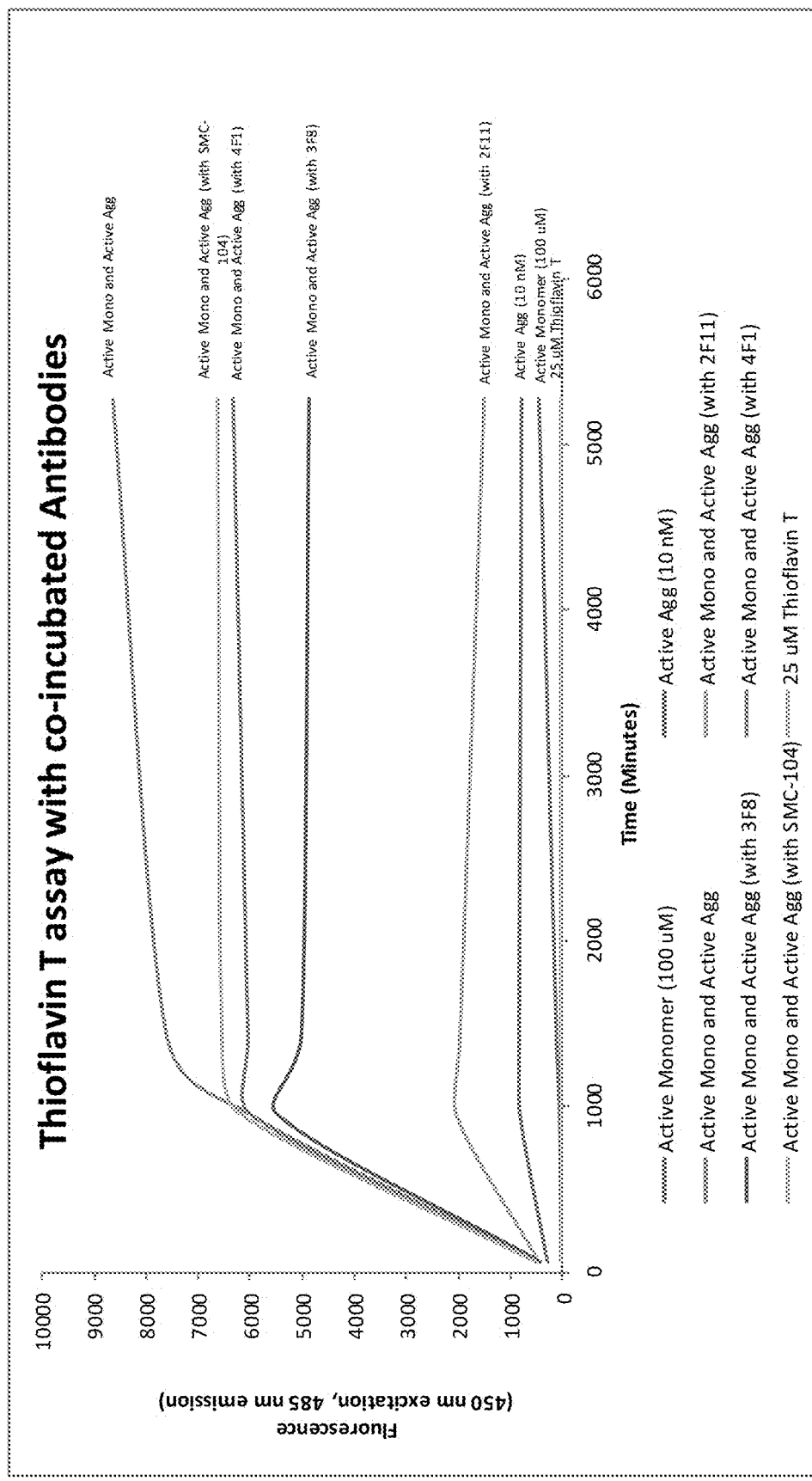
FIG. 9B shows time course Thioflavin activity assay in the presence of antibodies (2F11; 3F8; 4F1; SMC-104). Antibodies were added to the reaction when the reaction was initiated (time zero). Samples (from top to bottom): α-synuclein active monomer (100 µM)+active aggregate (10 nM); α-synuclein active monomer (10004)+active aggregate (10 nM)+SMC-104; α-synuclein active monomer (100 µM)+active aggregate (10 nM)+4F1; α-synuclein active monomer (100 µM)+active aggregate (10 nM)+3F8; α-synuclein active monomer (100 µM)+active aggregate (10 nM)+2F11; active aggregate 10 nM; active monomer (100 µM); Thioflavin control (25 µM).
Figure 9C:
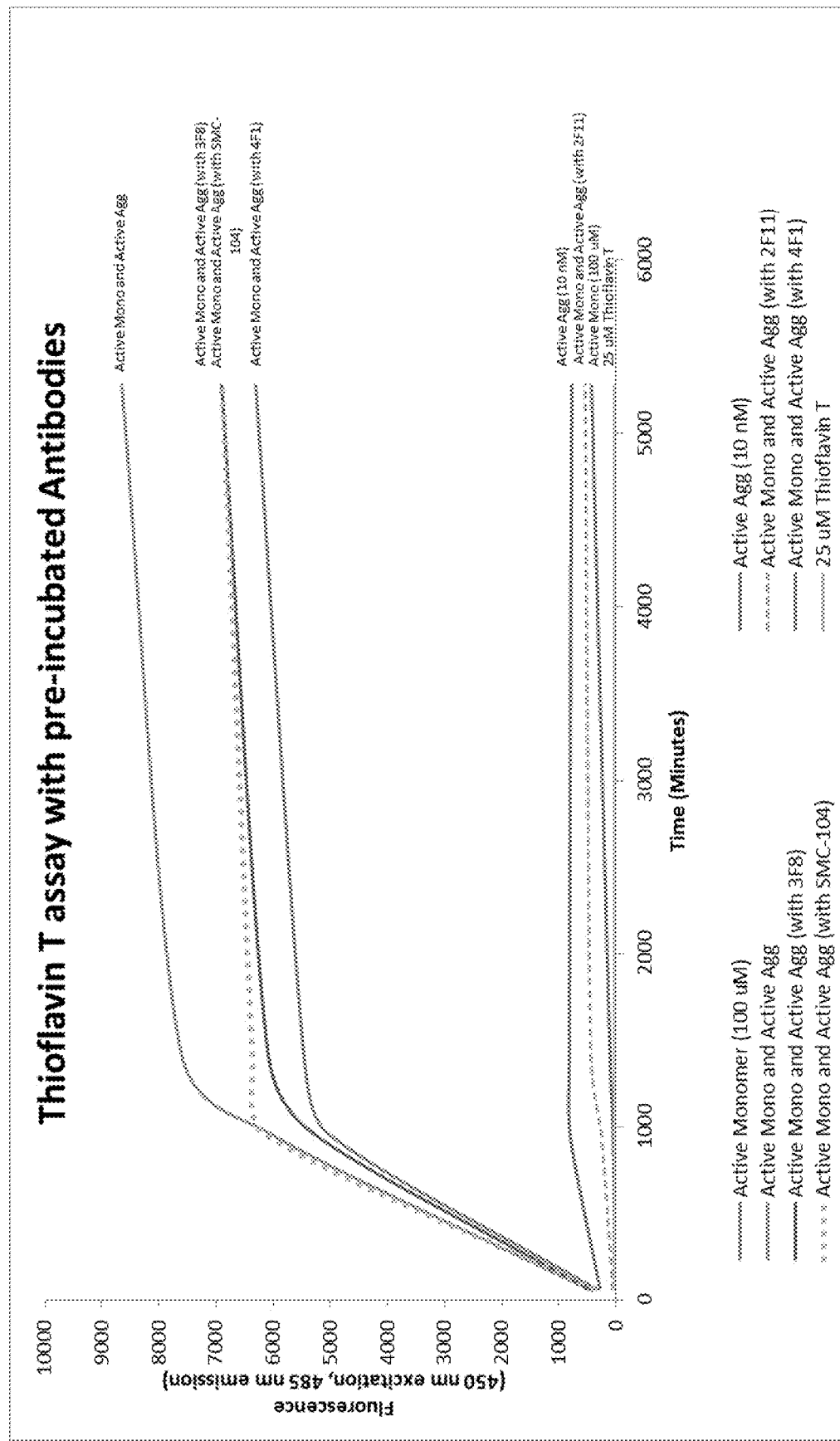
FIG. 9C shows time course Thioflavin activity assay in the presence of antibodies (2F11; 3F8; 4F1; SMC-104). Antibodies were pre-incubated with the sample prior to initiation of the reaction. Samples (from top to bottom): α-synuclein active monomer (100 µM)+active aggregate (10 nM); α-synuclein active monomer (100 µM)+active aggregate (10 nM)+3F8; α-synuclein active monomer (100 µM)+active aggregate (10 nM)+SMC-104; α-synuclein active monomer (100 µM)+active aggregate (10 nM)+4F1; active aggregate (10 nM); α-synuclein active monomer (100 µM)+active aggregate (10 nM)+2F11; active monomer (100 µM); Thioflavin control (25 µM).

The progression of the α-synuclein reaction was observed to be interrupted in the presence of monoclonal antibody 2F11, both when 2F11 was added at start of reaction (FIG. 9B), or when 2F11 was pre-incubated with the various α-synuclein species prior to start of reaction (FIG. 9C). Monoclonal antibodies 4F1 or 3F8 did not inhibit the progression of the α-synuclein reaction to the same extent when compared to the effect of 2F11. Furthermore, a control antibody SMC-104 (mouse monoclonal to hsp70) had little to no effect on the α-synuclein reaction.

These results clearly show that the 2F11 antibody binds a component or structure that is required for the α-synuclein aggregation and fibrillation reaction to proceed to form the β-sheet structure. The 2F11 antibody therefore shows a neutralization effect on this reaction.

These results suggest that binding of 2F11 to the virulent form of oligomeric α-synuclein from natural samples can be used to determine the amount of virulent α-synuclein oligomer in human brain lysate originating from a Parkinson's disease brain versus anon-Parkinson's disease brain, and to identify if higher amounts of virulent α-synuclein oligomer in human brain lysate originates from a Parkinson's disease brain.

Therefore, a method is provided for determining the presence of active oligomeric α-synuclein in a sample. The method comprising:
  i) pre-mixing a portion of the sample with a control antibody followed by adding the recombinant active α-synuclein monomer to produce a control treatment,
  ii) pre-mixing a second portion of the sample with the monoclonal antibody 2F11, followed by adding the recombinant active α-synuclein monomer to produce an active treatment, and
  iii) determining the amount of β-sheet structure formation in both the control treatment and the active treatment. Wherein a decrease in the amount of β-sheet structure formation in the active treatment, when compared with the control treatment, is indicative of the presence of the active oligomeric α-synuclein in the sample.

Furthermore, the α-synuclein oligomers isolated from natural human samples that can transmit the Lewy Body (DLB) disease may be used to seed active α-synuclein monomers and the time course kinetics of β-sheet structure formation monitored using the Thioflavin assay (using the method described in Example 5). This assay may be used to determine the amount of virulent α-synuclein oligomer in a sample, for example, cerebral spinal fluid (CSF), blood, human brain lysate, or other sample that may contain α-synuclein oligomer. This assay maybe used with samples obtained from a suspected Parkinson's disease brain (test sample) and the results compared with results obtained from a sample obtained from a non-Parkinson's disease brain (control sample), where an increase in the amount of virulent α-synuclein oligomer in the human brain lysate sample, when compared to the control sample, is indicative of Parkinson's disease in the test sample.

Figure 13:
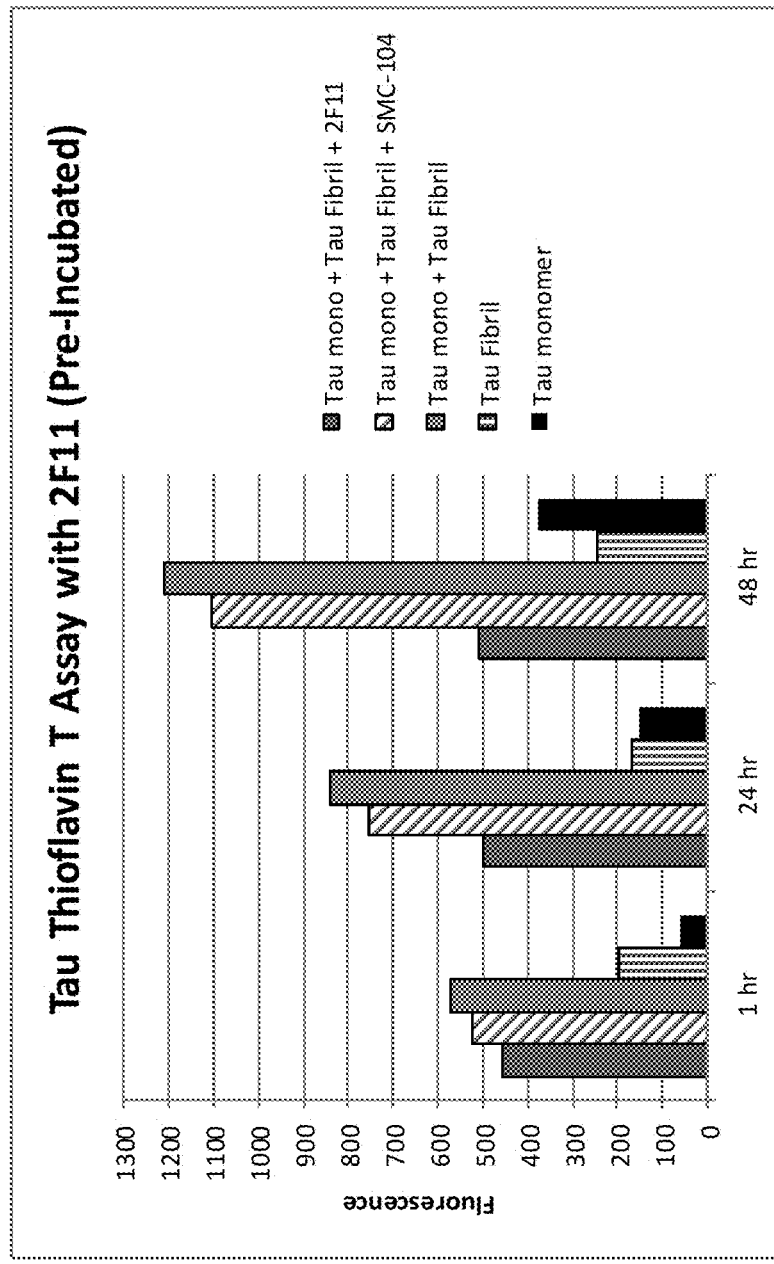
FIG. 13 shows a time course of the Thioflavin activity assay with tau. Antibodies were pre-incubated with tau fibril, and tau monomer was added to start the initiated. Florescence was determined after 1, 24, or 48 hours of incubation. Samples (left to right): tau monomer+tau fibril+2F11; tau monomer+tau fibril+SMC-104; tau monomer+tau fibril; tau monomer; and tau fibril

Due to the known interaction between tau and α-synuclein (Li, X., et. al., 2016, J. Mol. Neurosci. 60:298-304), the effect of the monoclonal antibody 2F11 on tau induced β-sheet structure formation was also examined using the Thioflavin assay. As shown in FIG. 13, 2F11 was observed to block Tau fibril, β-sheet structure formation in vitro. A background florescence signal was observed when Tau fibril alone, or Tau monomer alone were assayed. However, a mixture of Tau monomer and Tau fibrils results in production of a strong fluorescence signal indicating β-sheet structure formation over time. The progression of the tau reaction was observed to be interrupted in the presence of monoclonal antibody 2F11 when 2F11 was pre-incubated with the tau fibril prior to start of reaction. Monoclonal antibody SMC-104 (mouse monoclonal to hsp70) had little to no effect on the tau reaction. Higher amounts of the 2F11 antibody were required to block Tau fibril, β-sheet structure formation in vitro when compared to the amount added to block α-synuclein β-sheet structure formation in vitro Therefore, a method is provided for determining the presence of tau aggregation in a sample. The method comprising:
  i) pre-mixing a portion of the sample with a control antibody followed by adding tau monomer to produce a control treatment,
  ii) pre-mixing a second portion of the sample with the monoclonal antibody 2F11, followed by adding the tau monomer to produce an active treatment, and
  iii) determining the amount of β-sheet structure formation in both the control treatment and the active treatment. Wherein a decrease in the amount of β-sheet structure formation in the active treatment, when compared with the control treatment, is indicative of the presence of the tau aggregation in the sample.

These results clearly show that the 2F11 antibody binds a component or structure that is required for the α-synuclein aggregation and fibrillation reaction, and the tau reaction, to proceed to form the β-sheet structure. The 2F11 antibody therefore shows a neutralization effect on this reaction.

These results suggest that binding of 2F11 to the virulent form of oligomeric α-synuclein from natural samples can be used to determine the amount of virulent α-synuclein oligomer in human brain lysate originating from a Parkinson's disease brain versus anon-Parkinson's disease brain, and to identify if higher amounts of virulent α-synuclein oligomer in human brain lysate originates from a Parkinson's disease brain.

These results also suggest that binding of 2F11 to the fibrillar form of tau from samples may be used to determine the presence or absence, or the amount, of tau aggregate in human brain lysate originating from a diseased brain, for example Alzheimer's disease, versus a non diseased brain, and to identify if higher amounts of tau aggregate in human brain lysate are present in the diseased brain tissue.

Epitope binding of the 2F11 was characterized to a series of overlapping α-synuclein peptides each of approx. 30 amino acids in length. 2F11 clone exhibited a unique pattern of epitope binding (FIG. 10), when compared to other monoclonal antibodies that were also identified as binding the active form of α-synuclein (e.g. 4F1, 3F8). In this analysis, 2F11 was observed to bind two C-terminal fragments of α-synuclein, at positions 61-90 and 101-130. Without wishing to be bound by theory, the epitope binding properties of 2F11 allow it to bind and neutralize a core component of the alpha synuclein aggregation and fibrillization reaction.

Intrastriatal injection of 2F11 antibody was also observed to reduce the generation of Lewy-Body pathology in rat cortical cells. Administration of α-synuclein fibrils into cortical tissue seeded the α-synuclein reaction as determined using α-synuclein-specific antibody pSer129. The number of localized α-synuclein aggregate sites, and the size of the aggregates was reduced by pre-incubating the α-synuclein fibrils with the mono clonal antibody 2F11. Sections of cortical tissue obtained from rats treated with α-synuclein fibrils in PBS revealed localized fluorescence indicating binding of the α-synuclein antibody (pSer129) to α-synuclein fibrils and α-synuclein aggregate formation (perinuclear aggregations or inclusions). No fluorescence was observed in control (PBS) treated rats (indicating no α-synuclein aggregate formation). Localized fluorescence was also observed in rat cortical cells that were treated with α-synuclein fibrils and the antibody 3D10, indicating binding of the antibody (pSer129) to α-synuclein fibrils and α-synuclein aggregate formation. The amount of localized binding in cortical cells receiving α-synuclein fibrils and the antibody 3D10, was similar to that observed in slices of cortical tissue obtained from rats administered α-synuclein fibril alone. While localized fluorescence was observed in cortical cells obtained from rat brain treated with α-synuclein fibrils and the antibody 2F11, both the number of localized binding sites (perinuclear aggregations), and the size of the localized binding sites, were reduced when compared to either the number and size of binding sites observed in cortical cells when treated with α-synuclein fibril alone, or α-synuclein fibrils and the antibody 3D10, demonstrating that treatment of brain tissue with the 2F11 antibody reduces the generation of Lewy-Body pathology in rat cortical cells, in vivo. The treatment using 2F11 may therefore obstruct or delay the formation of Lewy body-like inclusions. Without wishing to be bound by theory, increasing the amount of 2F11 that is administered to the cortical cells may also further obstruct, reduce and/or delay the generation of Lewy-Body pathology in rat cortical cells, in vivo.

The monoclonal antibody may be used to immunize a subject and reduce or inhibit the α-synuclein oligomerization reaction in vivo. For example, α-syn transgenic (tg) mice (PD model; Masliah et al., 2011) and non-tg mice may be immunized using 2F11, and the behavioral response (memory recovery) of both the α-syn transgenic (tg) mice and non-tg mice is evaluated over time. Tg mice immunized with 2F11 may have better memory recovery and may be able to complete their tasks in similar fashion to non tg mice thereby demonstrating that 2F11 antibody treatment reverses learning deficits.

As a result, the present invention contemplates a composition, or a vaccine, comprising the monoclonal antibody 2F11, or a multispecific. trispecific, or bispecific antibody comprising 2F11 (see below), in a pharmaceutically acceptable carrier, adjuvant, vehicle or excipient. Furthermore, a method of reducing active α-synuclein, or tau aggregation, in a subject in need thereof is also provided. The method comprising administering an amount of the composition, or the vaccine, to the subject. The composition, or the vaccine, may be administered to the subject orally, intranasally, intramuscularly, intraperitoneally, intravenously, or subcutaneously.

There is also disclosed a pharmaceutical composition comprising the antibody described herein, for example 2F11, or a multispecific, trispecific, or bispecific antibody comprising 2F11, and a pharmaceutically acceptable carrier (described below), adjuvant, or excipient. Administration of the therapeutic agent, for example 2F11, or the multispecific, trispecific, or bispecific antibody comprising 2F11, can be carried out using the various mechanisms known in the art, including naked administration, or it may be administered by intravenous, intraperitoneal, subcutaneous or oral routes, or direct injection. The therapeutic agent may also be administered as part of a pharmaceutical composition or preparation containing suitable pharmaceutically acceptable carriers comprising excipients and auxiliaries which facilitate processing of the therapeutic agents into preparations which can be used pharmaceutically.

Also provided herein is a method of inducing an immune response in a subject, that has been diagnosed with a synucleinopathy, a pathological condition characterized by Lewy bodies, Parkinson's disease, dementia with Lewy bodies, multiple system atrophy, Alzheimer's disease, sporadic Alzheimer's disease, or familial Alzheimer's disease, a taupathy, a pathological condition characterized by Neurofibrillary tangles, Alzheimer's disease, Pick's disease, progressive supranuclear palsy, corticobasal degeneration, frontotemporal dementia, argyrophilic grain disease, primary age-related tauopathy, neurofibrillary tangle-only dementia, and globular glial tauopathy, comprising administering the monoclonal antibody 2F11, a multispecific, trispecific, or bispecific antibody comprising 2F11, pharmaceutical composition comprising the monoclonal 2F11, a pharmaceutical composition comprising the multispecific, trispecific, or bispecific antibody comprising 2F11, a vaccine comprising the monoclonal 2F11, or a vaccine comprising the multispecific, trispecific, or bispecific antibody comprising 2F11, to a subject.

Also disclosed is use of the monoclonal antibody 2F11, a multispecific, trispecific, or bispecific antibody comprising 2F11, a pharmaceutical composition comprising 2F11, or pharmaceutical composition comprising a multispecific, trispecific, or bispecific antibody comprising 2F11, for inducing an immune response in a subject diagnosed with a synucleinopathy, a pathological condition characterized by Lewy bodies, Parkinson's disease, dementia with Lewy bodies, multiple system atrophy, sporadic Alzheimer's disease, familial Alzheimer's disease, a taupathy, a pathological condition characterized by Neurofibrillary tangles, Alzheimer's disease, Pick's disease, progressive supranuclear palsy, corticobasal degeneration, frontotemporal dementia, argyrophilic grain disease, primary age-related tauopathy, neurofibrillary tangle-only dementia, and globular glial tauopathy.

Also disclosed is a method of treating a synucleinopathy, a pathological condition characterized by Lewy bodies, Parkinson's disease, dementia with Lewy bodies, multiple system atrophy, sporadic Alzheimer's disease, or familial Alzheimer's disease, or a taupathy, a pathological condition characterized by Neurofibrillary tangles, Alzheimer's disease, Pick's disease, progressive supranuclear palsy, corticobasal degeneration, frontotemporal dementia, argyrophilic grain disease, primary age-related tauopathy, neurofibrillary tangle-only dementia, and globular glial tauopathy. The method comprising administering the monoclonal antibody 2F11, a multispecific, trispecific, or bispecific antibody comprising 2F11, a pharmaceutical composition comprising the monoclonal antibody 2F11, or a pharmaceutical composition comprising the multispecific, trispecific, or bispecific antibody comprising 2F11, to a subject. Also disclosed is use of the monoclonal antibody 2F11, a multispecific, trispecific, or bispecific antibody comprising 2F11, a pharmaceutical composition comprising the monoclonal antibody 2F11, or a pharmaceutical composition comprising the multispecific, trispecific, or bispecific antibody comprising 2F11, for treating a synucleinopathy, a pathological condition characterized by Lewy bodies, Parkinson's disease, dementia with Lewy bodies, multiple system atrophy, sporadic Alzheimer's disease, or familial Alzheimer's disease, in a subject.

Also disclosed is use of the monoclonal antibody 2F11, or a multispecific, trispecific, or bispecific antibody comprising 2F11 in manufacture of a medicament for treating a synucleinopathy, a pathological condition characterized by Lewy bodies, Parkinson's disease, dementia with Lewy bodies, multiple system atrophy, sporadic Alzheimer's disease, or familial Alzheimer's disease, or for treating a taupathy, a pathological condition characterized by Neurofibrillary tangles, Alzheimer's disease, Pick's disease, progressive supranuclear palsy, corticobasal degeneration, frontotemporal dementia, argyrophilic grain disease, primary age-related tauopathy, neurofibrillary tangle-only dementia, and globular glial tauopathy. Also disclosed is the monoclonal antibody 2F11, or the multispecific, trispecific, or bispecific antibody comprising 2F11, for use in manufacture of a medicament for treating a synucleinopathy, a pathological condition characterized by Lewy bodies, Parkinson's disease, dementia with Lewy bodies, multiple system atrophy, sporadic Alzheimer's disease, or familial Alzheimer's disease, or for use in manufacture of a medicament for treating a taupathy, a pathological condition characterized by Neurofibrillary tangles, Alzheimer's disease, Pick's disease, progressive supranuclear palsy, corticobasal degeneration, frontotemporal dementia, argyrophilic grain disease, primary age-related tauopathy, neurofibrillary tangle-only dementia, and globular glial tauopathy.

The antibody may be a monoclonal antibody. The antibody may be non-human, primatized, humanized or fully human. Methods for humanizing or primatizing non-human antibodies are well known in the art, e.g. by substituting rodent complementarity determining regions (CDRs) or other amino acids or sequences for those of a human antibody (for example see, Jones et al., Nature 321:522-525 (1986); Riechmann et al., Nature 332:323-327 (1988); Verhoeyen et al., Science 239:1534-1536 (1988) and Presta, Curr. Op. Struct. Biol. 2:593-596 (1992), Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994); each of which is herein incorporated by reference in its entirety). As used herein, the term "antigen binding domain" means any antibody derivative or fragment which possesses antigen binding activity. In some examples the antigen binding domain comprises antibody light chain and heavy chain variable domains (i.e. VL and VH domains). Non-limiting examples of antibody fragments and derivatives are Fab, Fab', F(ab')2, scFv (i.e. single chain Fv), scFv-Fc, minibodies, nanobodies, diabodies, tri(a)bodies, multispecific antibodies, trispecific antibodies, bispecific antibodies, and the like. Many other antibody fragments and derivatives are known, a number of non-limiting examples of which are disclosed in Deyev and Lebedenko (2008, BioEssays 30:904-918, incorporated by reference in its entirety). In some embodiments of the methods or uses, the antigen binding domain is a Fab, a Fab', a F(ab')2, a scFv, a scFv-Fc, a minibody, a nanobody, a diabody or a tri(a)body.

Figure 12:
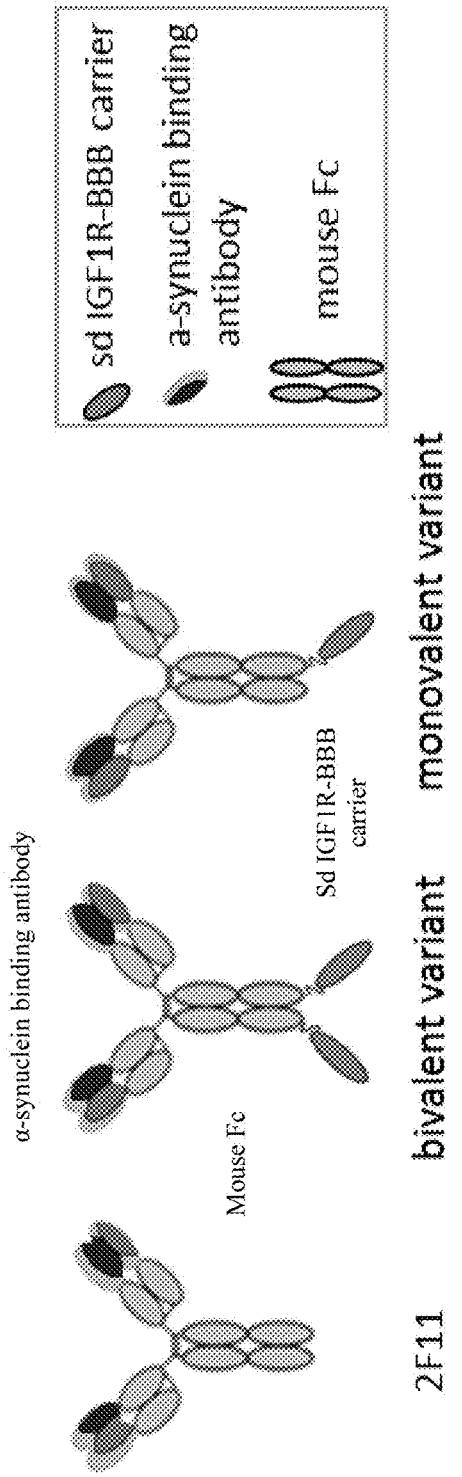
FIG. 12 shows a schematic representation of examples of multispecific antibodies. In this non-limiting example, bispecific antibodies, comprising various carrier molecules are shown along with a schematic of 2F11 (left hand panel). The bispecific antibody comprises a single domain of insulin growth factor 1 receptor (sd-IFG1R-BB; lower portion of molecule) as a bivalent (middle panel) or monovalent right hand panel) variant, covalently attached to a cargo molecule comprising a mouse Fc (mid-portion of molecule) and an α-synuclein antibody (upper portion of molecule).

Methods to transport therapeutic antibodies across the blood brain barrier, using multispecific antibodies, for example, bispecific or trispecific antibodies, comprising one or more than one carrier molecule, and one or more than one cargo molecule, via a receptor-mediate transcytosis pathway are known. For example, a transferin receptor (TfR)-binding antibody (and variants thereof) may be used as the carrier, and when fused to a cargo molecule, for example 2F11, produces a bispecific antibody that is able to cross the blood brain barrier (see for example Zuchero, Y. J, Y., et. Al., 2016, Neuron 89:70-82; Bien. Ly, N. et. al. 2014 J. Exp. Med. 211:233-244; US 2018/8002433; CA 3,000,560; which are incorporated herein by reference). Alternatively, an insulin-like growth factor 1 receptor (IGF1R)-binding antibody may be used as a carrier, and fused to the cargo molecule 2F11, to produce a bispecific antibody that crosses the blood brain barrier (see for example WO2015/131256; WO2015/131257; WO2015/131258; which are incorporated herein by reference). An example of a monovalent or bivalent IGF1R bispecific antibody comprising 2F11, capable of transmigrating the blood brain barrier is shown in FIG. 12. Absolute antibody (see URL: absoluteantibody.com/custom-services/antibody-engineering/) describe preparing multispecific antibodies.

Therefore, the present disclosure also provides a multispecific antibody, for example a trispecific or bispecific antibody, for transmigrating the blood brain barrier, the bispecific antibody comprising a carrier molecule attached to the monoclonal antibody 2F11. The carrier molecule of, for example, the bispecific antibody may be either a monovalent-bispecific antibody or a bivalent-bispecific antibody. The bispecific antibody may be either a transferin receptor (TfR)-binding antibody, or an insulin-like growth factor 1 receptor (IGF1R)-binding antibody.

The present invention will be further illustrated in the following examples.

Example 1: Materials and Methods

α-Synuclein Immunogen Generation:

Inactive human α-synuclein monomers and aggregates were made according to Volpicelli-Daley et al., 2014 (which is incorporated herein by reference), with the minor amendments. Fractions containing the monomeric form of α-synuclein were pooled and subjected to endotoxin removal procedure using Pierce High Capacity Endotoxin Removal Spin Column (Thermo Scientific, #88276) according to the manual provided by the supplier. Endotoxin level was measured using ToxinSensor Chromogenic LAL Endotoxin Assay Kit (GenScript, #L00350). Endotoxin level was below 1 EU per µg of protein as determined by the LAL assay. Inactive monomers were used to make the inactive aggregates.

Active mouse seed α-synuclein aggregates (pre-formed fibrils—PFFs) and active α-synuclein monomers were obtained from the Lee laboratory (Center for Neurodegenerative Disease Research, 3rd Floor, Maloney Building, 3600 Spruce Street, Philadelphia, PA. 19104-4283, USA). Mouse brain lysate was donated by the University of Victoria (3800 Finnerty Rd, Victoria, BC V8P 5C2, Canada). Human brain whole tissue lysate (5 mg/mL) was obtained from Novus Biologicals, #NB820-59177. Human brain Parkinson's disease whole tissue lysate (5 mg/mL) was obtained from Novus Biologicals, #NB820-59407. HeLa lysate was obtained from Rockland Immunochemicals Inc., #W09-000-364.

Thioflavin Assay:

The Thioflavin assay was based on Murray et al., 2003 (which is incorporated herein by reference). This assay measures the β-sheet content over time. An increase in fluorescence is indicative of an increase in β-sheet structure due to an increase in aggregated fibrils during a seeded reaction.

Thioflavin T stock (1 mM) was diluted in PBS to 25 µM final concentration (1:40 dilution). 95 µL of the diluted Thioflavin T was added to each well of a 384 well, a sample (2.5 µL) was added to each well, and the solution mixed. For controls, 2.5 µL PBS alone was added to the diluted Thioflavin T, and 2.5 µL monomeric α-synuclein was added to the diluted Thioflavin T. The mixtures were incubated at room temperature from 2 minutes to 1 hour, and the Thioflavin T florescence determined in each well (excitation 450 nm, emission 500 nm). Changes to the Thioflavin T assay described above were as follows: The Thioflavin T florescence was determined in each well (excitation 450 nm, emission 485 nm) after incubation at 37° C. from 1 hour up to 88 hours.

For pre-incubation studies, 30 ug of antibody was incubated with 10 nM α-synuclein aggregate for 1 hour at 4° C. with shaking. The mixture was centrifuged at 10000 rpm for 5 minutes and rinsed with 1 mL PBS. This step was repeated 4 additional times. The supernatant was removed and the α-synuclein aggregate (with bound antibody) was resuspended in 10 µL PBS.

For co-incubation studies, 30 ug of antibody was added to the monomeric α-synuclein and α-synuclein aggregates just prior to the addition of the Thioflavin T.

Mouse Monoclonal Antibody Generation:

Mouse monoclonal antibodies were made at ImmunoPrecise Antibodies Ltd (IPA) located at 4464 Markham Street #3204, Victoria, BC V8Z 7X8, Canada using their proprietary RapidPrime technology. The RapidPrime included the immunization of 5 female BALB/c mice.

Hybridoma Screening on α-Synuclein Fibrils Antigen by Indirect ELISA:

ELISA Conditions: Corning Costar ELISA plates were coated with active α-synuclein aggregates or active α-synuclein monomers at 0.1µg/well in 100 µl/well CCB (pH 9.6) overnight at 4° C., blocked with 3% skim milk powder in PBS for 1 hour at room temperature.

Primary Antibody: Hybridoma TC sup neat (generated at IPA) at 100 uL/well incubated for 1 hour at 37° C. with shaking; Secondary Antibody 1:10,000 Goat anti-mouse IgG/IgM (H+L)-HRP (Jackson ImmunoResearch, #115-035-068) at 100 uL/well in PBS-Tween for 1 hour at 37° C. with shaking. All washing steps were performed for 30 mins with PBS-Tween. TMB Substrate (BioFxt #TMBW-1000-01) added at 50 µL/well and the reaction stopped with equal volume 1M HCl. Development time: 8.5 minutes. Plate was read at 450 nm.

Isotyping Antibody Trapping ELISA Conditions:

ELISA plate coated with 1:10,000 Goat anti-Mouse IgG/IgM (H&L; Jackson ImmunoResearch, #115-035-068) in carbonate coating buffer (pH9.6) overnight at 4° C., no blocking.

Primary antibody: Hybridoma tissue culture supernatant (neat; same antibody described for indirect ELSIA outlined above) on plates at 100 uL/well for 1 hour at room temp with shaking. Secondary Antibody 1:5000 Goat anti-mouse IgGγ-HRP (an equal parts mixture of 5 subisotype specific antibodies, Jackson ImmunoResearch, #115-035-205, 115-035-206, 115-035-207, 115-035-208, 115-035-209) or 1:10,000 Goat anti-mouse IgMµ-HRP (Thermo Scientific, #31440) at 100 uL/well in PBS-Tween for 1 hour at room temp with shaking. All washing steps performed for 30 mins with PBS-Tween. TMB Substrate was added at 50 µL/well and reaction stopped with equal volume 1M HCl. Development time: 5.5 minutes. Plate was read at 450 nm.

Testing Mouse Anti-α Synuclein Hybridomas on α-Synuclein Active Monomer, α-Synuclein Active Aggregates (or Pre Formed Fibrils; PFFs), α-Synuclein Inactive Monomer, and α-Synuclein Inactive Aggregate Antigens by Indirect ELISA ELISA Conditions: Corning Costar ELISA plates coated with:
 a. α-synuclein Active Monomer at 0.1 µg/well in 100 µl/well CCB (Carbonate Coating Buffer) pH 9.6 overnight at 4° C.;
 b. α-synuclein active aggregate (PFFs) at 0.1 µg/well in 100 µl/well CCB (pH 9.6) overnight at 4° C.;
 c. α-synuclein inactive monomer at 0.1 µg/well in 100 µl/well CCB (pH 9.6) overnight at 4° C.; or
 d. α-synuclein inactive aggregate at 0.1 µg/well in 100 µl/well CCB (pH 9.6) overnight at 4° C., and blocked with 3% skim milk powder in PBS for 1 hour at room temperature.

Primary Antibody: Hybridoma tissue culture supernatant (neat) were grown in DMEM Complete media plus 5% low-IgG FBS to extinction (>90% cell dead). Cultures were harvested and spun down at 400×g and supernatant transferred to new sterile tubes. Tissue culture supernatants were added (100 µL/well) and incubated for 1 hour at 37° C. with shaking. Secondary Antibody 1:10,000 Goat anti-mouse IgG/IgM (H+L)-HRP at 100 uL/well in PBS-Tween for 1 hour at 37° C. with shaking. All washing steps performed for 30 mins with PBS-Tween. TMB Substrate was added at 504/well and the reaction was stopped with equal volume 1M HCl. Development time: 1 minute. Plates were read at 450 nm.

Western Blotting:

Gels were run under denaturing (SDS) and non-denaturing (native) conditions as noted in the examples below, prior to blotting and probing with various antibodies.

For FIGS. 3A-3D, primary antibody (anti-α-synuclein supernatants as defined in the previous section) was used at a dilution of 1:2 in tris-borate saline (TBS); incubation temperature: 4° C., incubation time: 18 hours. Secondary antibody was goat-anti-mouse:HRP Conjugate, dilution: 1:2000. Blocking buffer (5% Skim milk TBST), incubation temperature: room temperature; Incubation Time: 1 hr. Development solution: Amersham ECL substrate (GE, #RPN2232), development time: 6 minutes. Lysates: 20 µg mouse brain lysate, or HeLa lysate, per lane. 5X Laemmli Sample Buffer was added to the sample and was incubated for 10 minutes at 90° C. prior to being loaded onto the gel Visualized on Licor C-Digit, or GE ImageQuant LAS 500.

For FIG. 7 (and peptide Westerns), primary antibodies were anti-α-synuclein Protein G purified supernatants (GE, #29-0485-81); diluted 1:1000 in TBS; incubation temperature: room temperature; Incubation Time: 1 hr. Secondary antibody was goat-anti-mouse:HRP Conjugate, dilution: 1:2000. Blocking buffer (5% Skim milk TBST), incubation temperature: room temperature; Incubation Time: 1 hr. Development solution: SuperSignal™ West Pico Chemiluminescent Substrate (ThermoFisher Scientific, #34080), development time: 6 minutes. 5X Laemmli Sample Buffer was added to the samples and incubated for 10 minutes at 90° C. prior to being loaded onto the gel. For native samples, 5% glycerol was added prior to being loaded onto the gel instead of 5X Laemmli Sample Buffer. Visualized on GE ImageQuant LAS 500.

For dot blot analysis, 5 µl (0.1 mg/mL) of each peptide was added to nitrocellulose (ABM, #B500) and allowed to dry at room temperature for 15 minutes. The dot blots were then handled as a standard Western blot (outlined above with reference to FIG. 7).

Figure 2A:
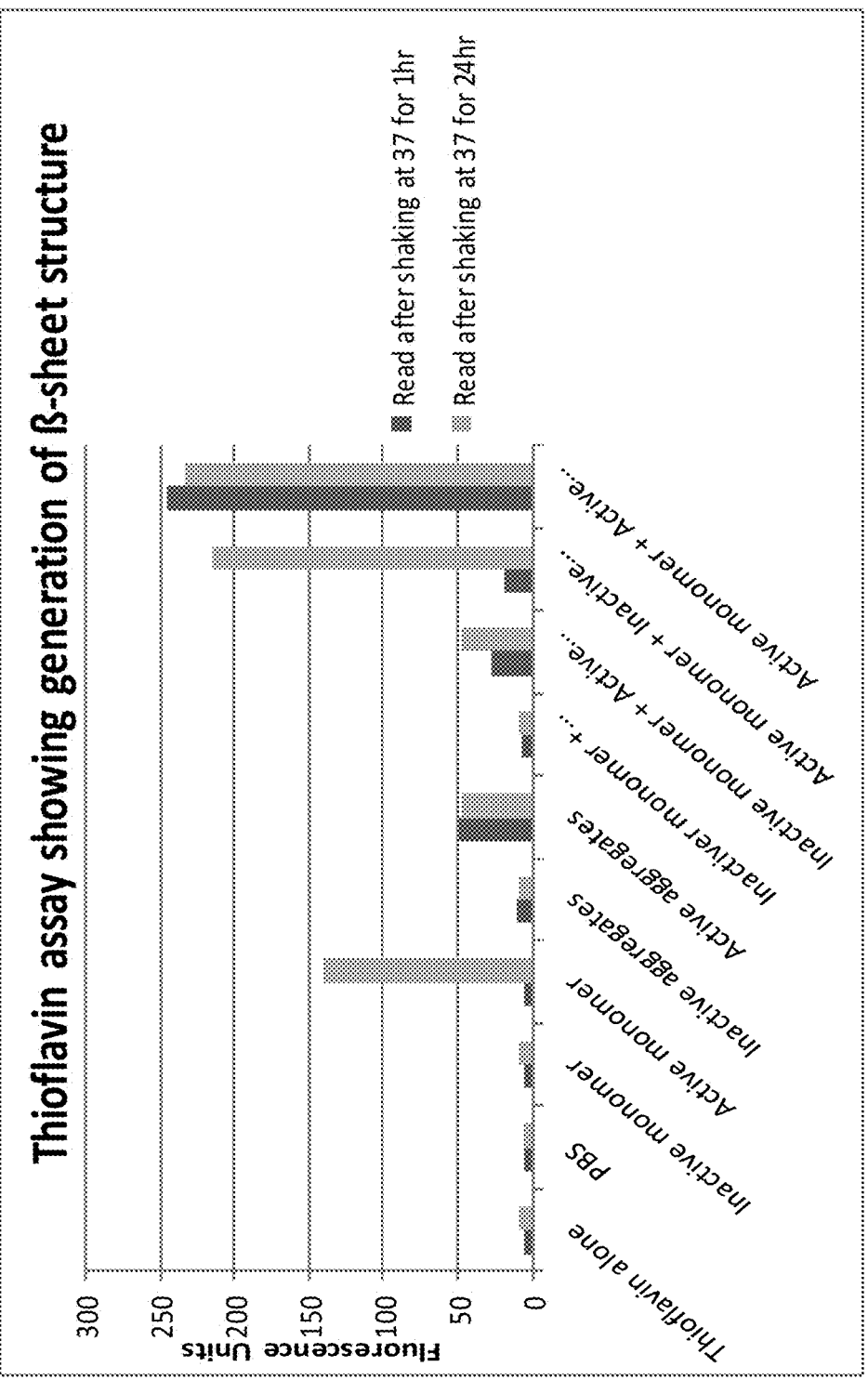
FIG. 2A shows Thioflavin assay results associated with α-synuclein beta-sheet structure formation following incubation of various inactive monomers, inactive aggregates, active monomers active aggregates, and combination thereof. Left hand bar: florescence determination after 1 hour incubation time (at 37° C.); Right hand bar: florescence determination after 24 hour incubation time (at 37° C.; see Examples for details).
Figure 9D:
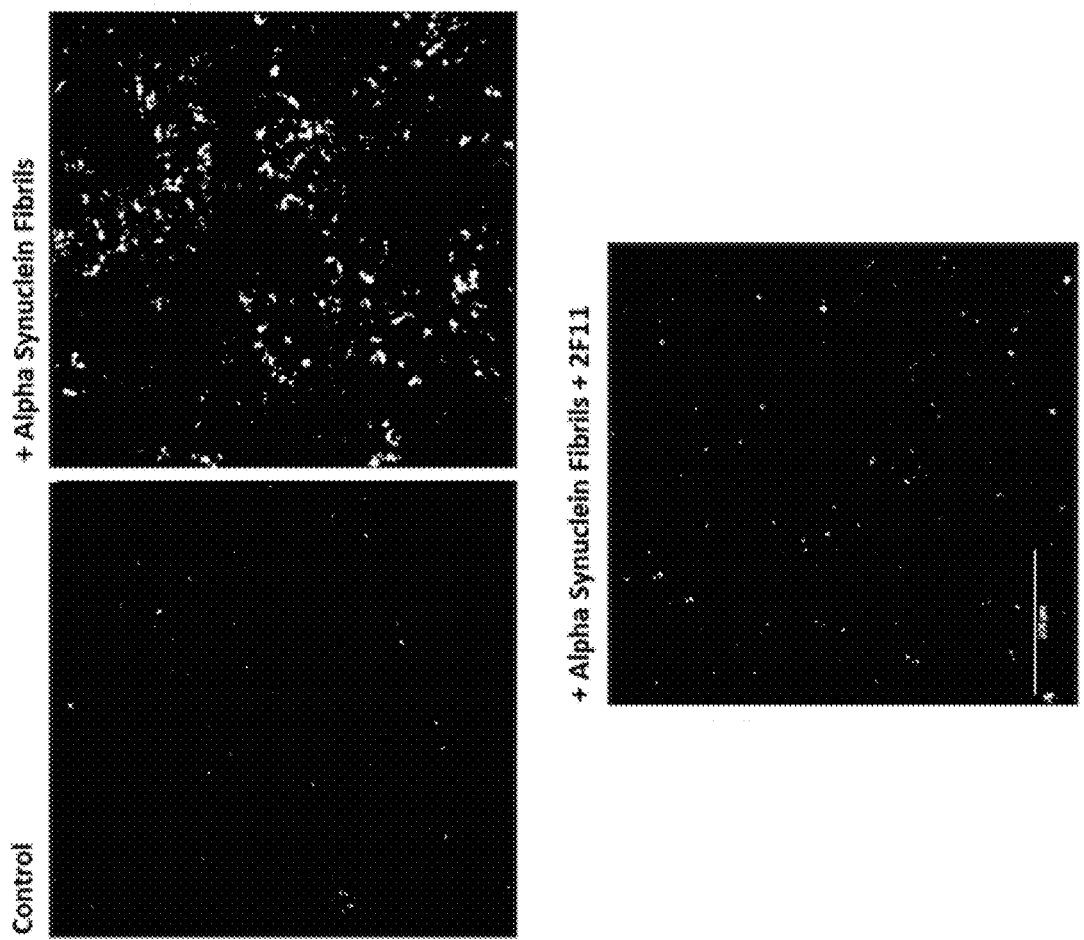
FIG. 9D shows confocal images of primary brain cells from Sprague-Dawley rats. Left upper panel: control, probed using DAPI and pSer129 alpha-synuclein antibody (only DAPI stained nuclei are identified); right upper panel: addition of active α-synuclein fibrils and probed with DAPI and pSer129 alpha-synuclein antibody (shows DAPI and pSer129 staining indicating binding to α-synuclein antibody, indicative of α-synuclein pathology); lower panel: addition of active α-synuclein fibrils+2F11 and probed with DAPI and pSer129 alpha-synuclein antibody (shows DAPI staining with background levels of pSer129 staining). 20× magnification; bar: 250 µm.

Primary Cell Experiments (FIGS. 2A and 9D)

Sprague-Dawley primary cortical cells were obtained by dissecting the brain of rat pups. After dissection, the brain was mechanically sectioned with surgical scissors and dissociated using a 0.25% Trypsin solution. The trypsinization was performed for 45 minutes and a cell suspension was obtained. Trypsin was washed out by 2 rounds of centrifugation (20 mins at 750 rpm), and the cell suspension plated in a 60 mm cell culture dish pre-incubated with laminin and filled with DMEM+10% FBS+Pen/Strep and was allowed to settle for 24 h. The next day, the supernatant of the 60 mm cell culture dish (containing neurons) was recovered, resuspended in the same growth medium (DMEM, 10% FBS, Pen/Strep) and washed 2 times by centrifugation (20 mins at 500 rpm). Suspended neurons were plated in 22×22 cm coverslips (pre-treated with in NaOH and 95% Ethanol) pre-incubated with laminin. Coverslips were placed in pairs in 60 mm cell culture dishes (2 coverslips per dish) or individually in 35 mm cell culture dishes and these were filled with DMEM+0.5% FBS+Pen/Strep. Neurons were allowed to settle and grow for 2 days and then their specific experimental conditioning was initiated. Once cells were ready, the cell culture media was replaced with the conditioning media. With reference to FIG. 9D the conditioning media was as follows:
 control experiments: DMEM+0.5% FBS+Pen/Strep+equivalent volume of sonicated DPBS+equivalent volume of DPBS;
 active α-synuclein only addition: DMEM+0.5% FBS+Pen/Strep+4 µg/ml of sonicated active α-Syn Fibrils+equivalent amount of BPBS;
 2F11-treated neurons: DMEM+0.5% FBS+Pen/Strep+4 µg/ml of sonicated active α-Syn Fibrils+10 µl of 2F11 antibody diluted 1:400 in DPBS (2F11 antibody amount equaled 10 µg).

Control groups were incubated with DPBS, active α-synuclein only addition groups were incubated with active α-Synuclein Fibrils, and 2F11 groups were co-incubated with active α-Synuclein Fibrils and the 2F11 antibody. 50% of the media was replaced by fresh media (DMEM+0.5% FBS+Pen/Strep) once a week.

After 14 days of incubation with conditioning media, cells were fixed in 2% PFA for 40 mins, permeabilized in 0.05% Triton-X for 10 mins and blocked with PBS-BSA 2% for 24 h. The cells were stained overnight with the primary rabbit polyclonal antibody from StressMarq against α-Syn-pSer129 (SPC-742) at a 1:100, and secondary antibody was Goat-Anti-Rabbit-Alexa-488 (green) for α-Syn-pSer129 Incubation was 2 h. All samples were counterstained with DAPI.

Peptide Synthesis for Epitope Mapping (FIG. 10)

The following peptides (Atlantic Peptides, USA) were generated on a Rainin Symphony synthesizer (residue numbers on the right), reflecting overlapping sequences of human α-Synuclein (Uni Prot P37840) using Fmoc chemistry and HCTU as the activator. The N-termini were conjugated to a C-6 spacer (Ahx), which in turn was conjugated to a cysteine residue at the N-terminus. Peptides were purified by reverse phase HPLC over a C-18 column. Analysis was performed using an Electro-spray for mass and an analytical LC for purity. The BSA used was Fishers Scientific product 77110 and the conjugation used followed the protocol provided with the product.

```
AA 1-30:
                                       (SEQ ID NO: 3)
MDVFMKGLSK AKEGVVAAAE KTKQGVAEAA;

AA 21-50:
                                       (SEQ ID NO: 4)
KTKQGVAEAA GKTKEGVLYV GSKTKEGVVH;

AA 41-70:
                                       (SEQ ID NO: 5)
GSKTKEGVVH GVATVAEKTK EQVTNVGGAV;

AA 61-90:
                                       (SEQ ID NO: 6)
EQVTNVGGAV VTGVTAVAQK TVEGAGSIAA;

AA 81-110:
                                       (SEQ ID NO: 7)
TVEGAGSIAA ATGFVKKDQL GKNEEGAPQE;

AA 101-130:
                                       (SEQ ID NO: 8)
GKNEEGAPQE GILEDMPVDP DNEAYEMPSE;

AA 121-140:
                                       (SEQ ID NO: 9)
DNEAYEMPSE EGYQDYEPEA.
```

ELISA conditions for epitope mapping: Nunc® MaxiSorp™ 98 well plates ELISA plates were coated with peptide conjugated to BSA at 0.1 μg/well in 100 μl/well CCB (pH 9.6) overnight at 4° C. The plates were then blocked with 3% skim milk powder in PBS for 3 hours at room temperature. 100 μL/well antibody (1 μg/mL) was added and incubated for 1 hour at 37° C. Secondary Antibody 1:10,000 Goat anti-mouse IgG/IgM (H+L)-HRP at 100 uL/well in PBS-Tween for 1 hour at room temperature. All washing steps performed for 30 mins with PBS-Tween. TMB Substrate was added at 100 μL/well and the reaction was stopped with equal volume 1M HCl. Development time: 15 minutes. Plates were read at 450 nm.

Immunoprecipitation, and Flow Though Analysis (FIGS. 5A and 5B)

1.2 mg of 2F11 was coupled to cyanogen bromide activated Sepharose (Sigma, #C9142-1G) using the manufacturer's protocol. 2 mg of mouse brain lysate was incubated with the resin at 4° C. for 48 hours with shaking. The column was washed with PBS and then eluted with 0.1 M glycine, pH 2.7.

Figure 2B:
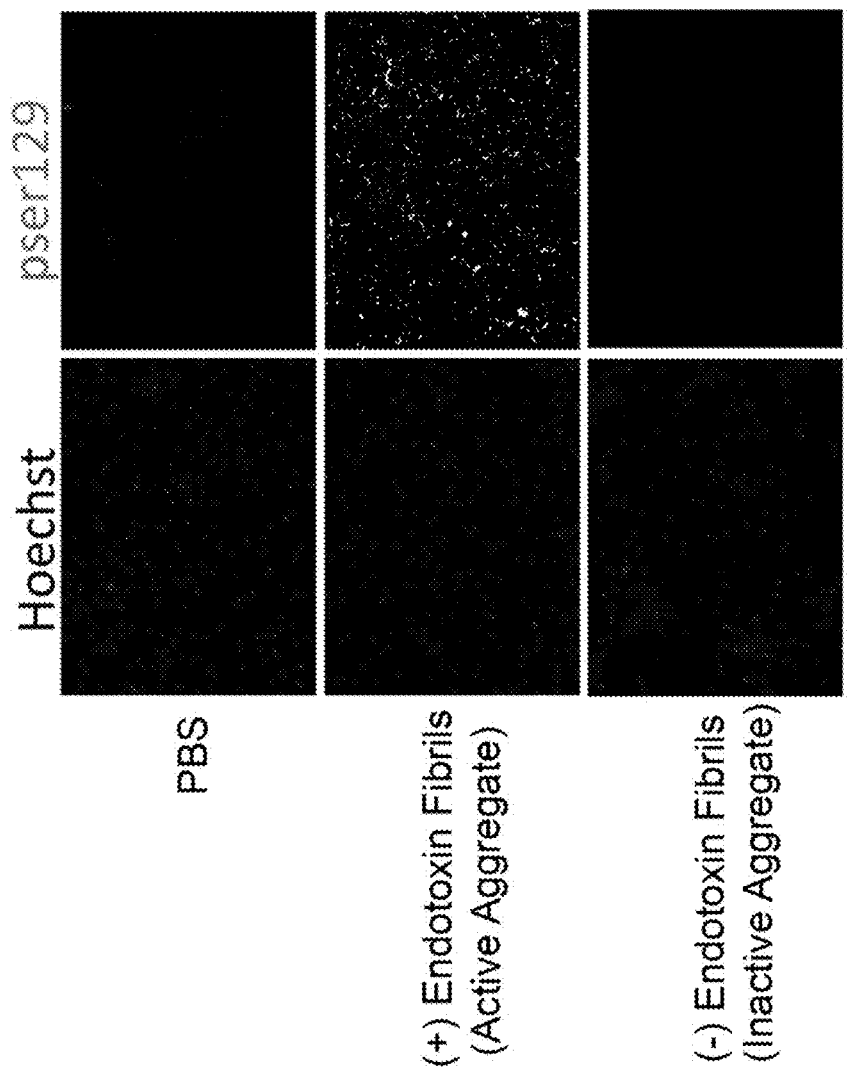
FIG. 2B shows confocal images of rat primary cortical cells incubated with inactive aggregates (made with α synuclein monomers in the absence of endotoxin), or active aggregates (made in the presence of endotoxin). Fluorescence measured using serine 129 phospho-specific antibody for the detection of Lewy Body pathology. Hoechst: DAPI staining; pser129: FITC-labelled serine 129 phospho-specific antibody.
Figure 2C:
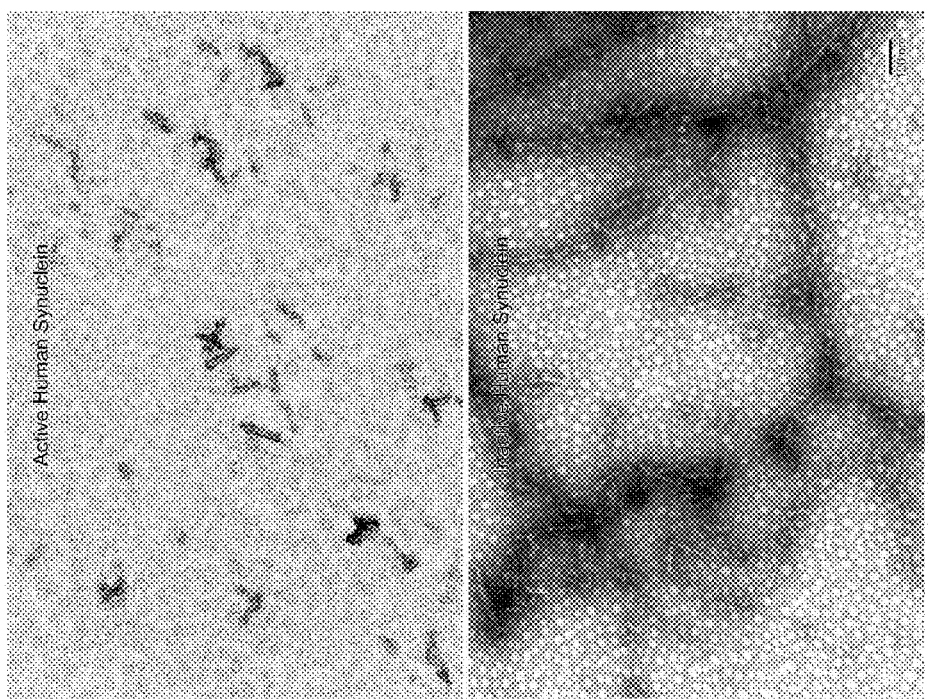
FIG. 2C shows electron microscopy images of active human α-synuclein fibrils (upper panel) and inactive human α-synuclein fibrils (lower panel). Bar: 100 nm.
Figure 8C:
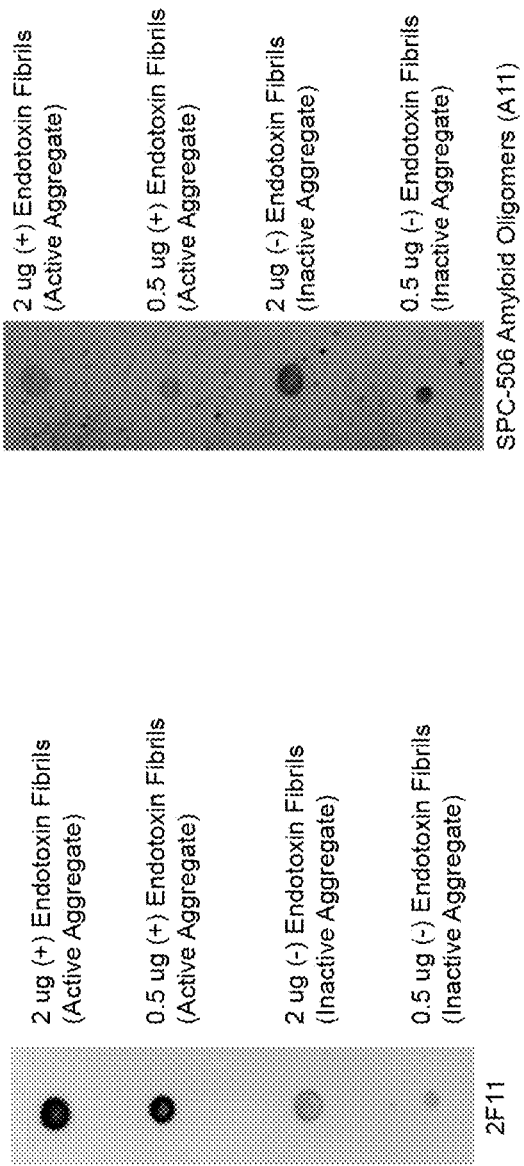
FIG. 8C shows dot blot analysis of active and inactive α-synuclein aggregates (fibril) binding to 2F11 (left hand panel) and SPC-506 (A11; right hand panel). Top blot: 2 µg active α-synuclein aggregate; upper middle blot: 0.5 µg active α-synuclein aggregate; lower middle blot: 2 µg inactive α-synuclein aggregate; bottom blot: 0.5 µg inactive α-synuclein aggregate.

Electron Microscopy (FIGS. 2C, 8C)

A sonicated 160 μl aliquot of α-Syn Fibrils was resuspended in DMEM+10% FBS to a final volume of 1 ml. The resuspension was then separated into 2 microcentrifuge tubes to a final volume of 0.5 ml of the original resuspension in each tube and centrifuged for 40 minutes at 17,000 rpm. 80% of the supernatant was discarded and the remaining volume resuspended in a final volume of 0.5 ml of either DMEM+10% FBS+2F11 at a 1:400 dilution (1.25 μg of antibody) or DMEM+10% FBS+equivalent volume of DPBS. The incubation with the primary antibody (or just DPBS for the negative control) was allowed for 24 h. The next day, both tubes were centrifuged for 40 minutes at 17,000 rpm, and 80% of the supernatant was kept aside and the rest of the volume was resuspended in 0.5 ml of DMEM+10% FBS and washed and centrifuged at 17,000 rpm for 40 mins. 80% of the supernatant was kept aside and the rest of the volume was resuspended in DMEM+10% FBS+Goat anti-mouse IgG conjugated with 18 nm gold particles in both tubes. The secondary antibody incubation was 2 h, then the tubes were centrifuged for 40 mins at 17,000 rpm. 80% of the supernatant was kept aside and the rest of the volume was resuspended in DMEM+10% FBS. The resuspension was washed by centrifugation for 40 mins at 17,000 rpm. Finally, 80% of the volume was kept aside and approximately 4 μl of the rest of the volume (approx. 100 μl) was placed on top of a transmission electron microscopy metallic grid and stained with uranyl acetate.

Example 2: Generation of Inactive and Active α-Synuclein Monomers and Aggregates Inactive and active α-synuclein monomers and aggregates were obtained as outlined in Example 1. To evaluate if the soluble monomers and insoluble aggregates were active (prion-like) and able to seed, or be seeded by, the α-synuclein aggregation process, both sets of monomers and aggregates were tested in combinations using the Thioflavin assay described in Example 1 and incubated for 1 hour or 24 hours at 37° C. Both active and inactive aggregates, as well as monomers were assayed. Controls included Thioflavin alone, PBS alone and inactive monomers. The results are provided in FIG. 2A. In this assay, increased α-synuclein aggregation results in a corresponding increase in β-sheet structure formation. Thioflavin binds the β-sheet structure, and in this configuration Thioflavin fluoresces (at 485 nm) when excited at 450 nm. The amount of fluorescence at 485 nm is dependent upon the amount of Thioflavin binding, and the amount of binding is correlated with the amount of β-sheet structure formation. As a result, an increase in Thioflavin fluorescence is indicative of an increase in of β-sheet structure formation.

After incubating for 1 or 37 hours, no increase in fluorescence, indicative of β-sheet structure formation, was observed with inactive monomers or inactive aggregates. However, active monomers were able to self-seed and generate β-sheet structures over the 24 h period. Active aggregates (PFFs), also resulted in an increase in fluorescence after 1 hour and 24 hours, but this increase plateaued in the absence of monomeric building blocks required to generate β-sheets.

The combination of inactive aggregates and inactive monomers resulted in no increase in fluorescence, suggesting that the inactive aggregates could not seed the inactive monomers, and also that self-seeding by the inactive monomers could not occur. The combination of inactive monomer and active aggregates (PFFs) produce a similar level of fluorescence as adding PFFs (active aggregates) alone since the inactive monomers could not function as building blocks to generate β-sheets structures. However, when active monomers were combined with inactive aggregates a large increase in fluorescence was observed over 24 hours. This is consistent with the result demonstrating that active monomers could self-seed. Finally, when both active monomers and aggregates were used together, a large increase in fluorescence reading was generated after both 1 hour and 24 hours, indicating aggregation by the seeding process by PFFs (active aggregates) on active monomers.

Circular Dichroism Analysis of α-Synuclein

Circular dichroism was carried by Alliance Protein Laboratories, San Diego, USA using a Jasco-J-1500 spectropolarimeter, 0.1 cm cell for far UV. Secondary structure was calculated according to: CDNN version 2.1, Guid223; Bohm, G., Muhr, G., and Jaenicke, R (1992) Quantitative analysis of protein far UV circular dichroism spectra by neural networks. Protein Eng. 5, 191-195).

Non-active or inactive monomers, made as described in Example 1, appear to have similar secondary structures to active monomers. Active α-synuclein aggregates on the other hand appear to have more β-sheet content and less α-helix than inactive aggregates as determined by measuring secondary structure using circular dichroism measurements (Table 1).

TABLE 1

Secondary structure content of active and inactive monomers, and active or inactive aggregates using circular dichroism measurements.

| | α-Helix, % | Anti-parallel β-sheet, % | Parallel sheet, % | Turn, % | Random, % |
|---|---|---|---|---|---|
| Active Monomer | 6 | 33 | 4 | 25 | 38 |
| Inactive Monomer | 6 | 29 | 4 | 30 | 40 |
| Inactive Aggregate | 13 | 29 | 6 | 17 | 34 |
| Active Aggregate | 7 | 36 | 5 | 21 | 36 |

Active Aggregates Seed α-Synuclein Aggregation In Vivo

As shown in FIG. 2B, using serine 129 phospho-specific antibody for the detection of the Lewy Body pathology (method described in Example 1), inactive aggregates that were made with α-synuclein monomers in the absence of endotoxin do not exhibit any pSer 129 staining (inactive aggregate—pSer129), indicating that inactive aggregates do not seed endogenous α-synuclein aggregation in rat primary cortical cells. However, active aggregates made in the presence of endotoxin do seed α-synuclein aggregation as evidenced by pSer129 staining of cells that have been pre-treated with active α-synuclein aggregates (see active aggregate—pSer129).

To further ascertain the differences between inactive and active aggregates, both were types were viewed under electron microscopy. The inactive α-synuclein fibrils formed thinner filaments than the active α-synuclein filaments and the inactive α-synuclein fibrils were less tightly packed. Furthermore, the inactive α-synuclein fibrils were considerably longer, reaching several micrometers in length. The active α-synuclein fibrils on the other hand were about 55-75 nm in length by about 6-8 nm in width (see FIG. 2C). These results demonstrate that there are two populations of α-synuclein monomers and aggregates: an active α-synuclein population and an inactive α-synuclein population.

Example 3: Generation of Monoclonal Antibodies Against Active α-Synuclein Populations Mouse monoclonal antibodies were prepared to the active α-synuclein aggregates and active α-synuclein monomers (Example 1) using the RapidPrime technology as described in Example 1. Initial screening experiments on the first round of clones were carried out on either active monomers or active aggregates (PFFs) using indirect ELISA (where the antigen is coated onto a plate, the antibody being screened allowed to bind it and then this binding detected by adding a secondary antibody with specificity to a mouse monoclonal but also linked to horseradish peroxidase to catalyze a detection color reaction with TMB; Example 1), to identify positive clones. Selected antibody-secreting hybridomas were identified by their antibody titres and then isotyped as described in Example 1. Hybridomas secreting antibodies to the active form of the α-synuclein monomer, but not the inactive version, were selected. Overall 20 monoclonal antibodies were identified that bound the active form of the α-synuclein monomer.

Further characterization of selected monoclonal antibodies was carried out by using Western blot analysis of denatured mouse brain samples and HeLA lysate. One antibody (2F11) was identified that resulted in a unique banding pattern when compared to the other anti-alpha synuclein antibody clones. The sequence of 2F11 is provided in SEQ ID NO's:10-13; FIGS. 11A and B)

Figure 3D:
FIG. 3D shows a Western blot analysis of HeLa lysate ((known to produce α-synuclein, see URL: proteinatlas.org/ENSG00000145335-SNCA/cell), probed with clone 2F11. Left lane: marker (kDa); right lane clone 2F11. A high molecular weight band in the mouse brain lysate was identified using clone 2F11.

As shown in FIG. 3A, 2F11 identified a high molecular weight band (>150 kDa) as opposed to a 15 kDa band normally associated with monomeric α-synuclein. Other α-synuclein monoclonal antibodies, including 4F1 (FIG. 3B) and 3F8 (FIG. 3C) were observed to identify the 15 kDa band. Clones 4F1 and 3F8 were randomly selected from a pool of approximately 20 monoclonal antibodies all showing the same specificity. Furthermore, 2F11 identified a high molecular weight band (>150 kDa) in HeLa lysate (FIG. 3D; known to produce α-synuclein, see URL: proteinatlas.org/ENSG00000145335-SNCA/cell), The strong positive signal identified by 2F11 on Western blot did not appear to be a result of high levels of protein, since the level of protein was below the level of detection using Ponceau staining, or Coomassie Blue staining. Without wishing to be bound by theory, this result suggests that the protein identified by 2F11 may be an oligomer, comprising many alpha synuclein molecules (the molecular weight suggesting at least ten), which could provide multiple binding sites for the monoclonal antibody and produce a high western blot response despite being low in concentration.

The nucleic acid and amino acid sequence of the heavy and light chains of 2F11 is provided in FIG. 11.

The pI of the 2F11 antibody was determined to have two IgG1 bands with apparent pIs of 7.23 and 7.27 (determined using Biorad Ready Strip system, analyzed at Focus Proteomics, USA).

Mass spectrometry of the 2F11 antibody showed that it had light chains with mass 24,139 and heavy chains with mass 50,155 (analysis carried out at University of Victoria Proteomics Centre, Victoria, Canada).

Immunoprecipitation Using 2F11

Given the fact the 2F11 showed little or no affinity for the monomeric alpha synuclein protein in Western blot, 2F11 was used to immunoprecipitate mouse brain lysate under native conditions as described in Example 1. The precipitate and the flow through fraction were obtained and re-examined using Western blot analysis (proteins were removed from the antibody prior to running western blot by eluting them from the resin while the antibody remained covalently linked to the resin). The results are shown in FIGS. 5A and 5B.

If the 2F11 antibody only bound α-synuclein oligomers in the native lysate, then it is anticipated that western analysis of the immune precipitate would reveal a stabilized oligomer and no monomer, and this is what was observed (FIG. 5A). As shown in FIG. 5A, 2F11 identified a 60-70 kDa oligomer of α-synuclein in immune precipitated mouse brain lysates.

Monomeric species of the protein would be expected to be present in the materials washed away from the immune-precipitated oligomers (flow-through fraction), and this was observed (FIG. 5B). With reference to FIG. 5B, 2F11 was observed to bind three fractions: an α-synuclein monomer (approx. 15 kDa), a putative α-synuclein trimer (approx. 40 kDa), and the α-synuclein oligomer (60-70 kDa).

2F11 does not Bind Active α-Synuclein Monomer

In order to evaluate the binding of the 2F11 in vivo, BV-2 microglial cells were treated with either active α-synuclein oligomers, or active α-synuclein monomers that had been pre-incubated with the 2F11 antibody.

Mouse microglial BV-2 cells were seeded at 100,000 cells/well for 24 h in 24-well dishes on glass coverslips coated with poly-L-lysine. Active 50 µg/ml α-synuclein oligomers were pre-incubated with 5 µg/ml monoclonal α-synuclein; antibody (2F11), or control IgG in serum-free DMEM for 1 h on a shaker at RT. Active 50 µg/ml α-synuclein monomers were pre-incubated with 5 µg/ml monoclonal α-synuclein antibody (2F11) in serum-free DMEM for 1 h on a shaker at RT. 250 µl of medium containing alpha-synuclein immune complexes was added to the indicated wells and incubated for 1 h at 37° C. Following treatments, cells were fixed with 10% neutral-buffered formalin and subjected to double immunocytochemistry (ICC). 2F11 antibody in the alpha-synuclein immune complex was detected using an anti-mouse IgG antibody conjugated to Alexa 488. The route of internalization was detected using rabbit polyclonal LAMP-1 (ab24170, 1:200); Detection of LAMP-1 was achieved using anti-rabbit IgG conjugated to Cy5. Nuclei were counterstained using Hoechst 33258.

The oligomer-bound 2F11 was readily detected and found to be localized mainly at the cell surface. However, 2F11 did not form an immune complex with alpha-synuclein monomers (data not shown).

These results indicate that 2F11 binds alpha synuclein oligomers but not monomers under native conditions from native samples, and that under denaturing conditions (used during Western blot analysis) both stabilized oligomers and monomeric α-synuclein is identified by 2F11.

Example 4: Mouse Monoclonal Antibody Binds Human α-Synuclein

The similarity between mouse and human α-synuclein is 95% (see FIG. 6). The α-synuclein that was used to immunize mice was mouse in origin. To determine if 2F11 identifies high molecular weight α-synuclein oligomers in human samples, lysates from human brain, lysates from human brain from a Parkinson's patient, and lysate from a mouse brain were compared using Western blot analysis under denaturing conditions (FIG. 7) and under native conditions (FIGS. 8A and 8B).

With reference to FIG. 7, the 2F11 antibody showed it had at least dual mouse and human specificity binding high and mid molecular weight oligomers. The 150 kD band was slightly more prevalent in the Parkinson's brain lysate than human brain lysate, but less than in the mouse brain lysate. The same antibody also identified the monomeric α-synuclein band under denaturing conditions in both human and mouse samples.

With reference to FIG. 8A, binding of the 2F11 antibody under native (non-reducing) conditions was examined. A native gel was blotted and probed with the 2F11 antibody, and the 4F1 antibody (FIG. 8B). The results showed that 2F11 bound high molecular weight oligomers across human brain lysates, including Parkinsons brain lysate, and mouse brain lysate, of approx. 60 kD to about 250 kD, depending on the sample. 2F11 was also observed to bind purified active pathogenic α-synuclein monomers or aggregates under native conditions. The 4F1 antibody was also observed to bind higher molecular weight oligomers under native conditions. However, 4F1 did not recognize purified active pathogenic α-synuclein monomers or aggregates.

The results show that in a native system 2F11 can bind both human and mouse samples. Furthermore, the 2F11 antibody (and the 4F1 antibody) did not bind active alpha synuclein monomer under native conditions. Without wishing to be bound by theory, 2F11 may have a unique binding pattern to active α-synuclein aggregates that allows it to bind the pathogenic species of active α-synuclein oligomers, or an active oligomer directly involved in the pathway to creating the Lewy Body pathology.

The results show that the Parkinson's brain lysate has oligomeric α-synuclein present. It also shows that the antibodies are not mouse-specific but extend their species reactivity to human.

2F11 Binding Active Human α-Synuclein Aggregates

The specificity of the 2F11 antibody binding to active human α-synuclein aggregates and inactive human α-synuclein aggregates was examined by dot blot. In this assay, active and inactive synuclein types were placed onto nitrocellulose and probed using the 2F11. We also tested the ability of antibody A11, which has a positive specificity for prefibrillar Aβ oligomers (Kayed. R, et. al. 2007. Molecular Neurodegeneration 2007, 2:18 doi:10.1186/1750-1326-2-18) on active and inactive α-synuclein oligomer/fibril species. The results are shown in FIG. 8C and indicate that the 2F11 antibody only binds active α-synuclein aggregates. The A11 antibody shown by Kayed et. al. (2007) to bind α-synuclein oligomers only binds the inactive oligomeric/fibril species.

Figure 8D:
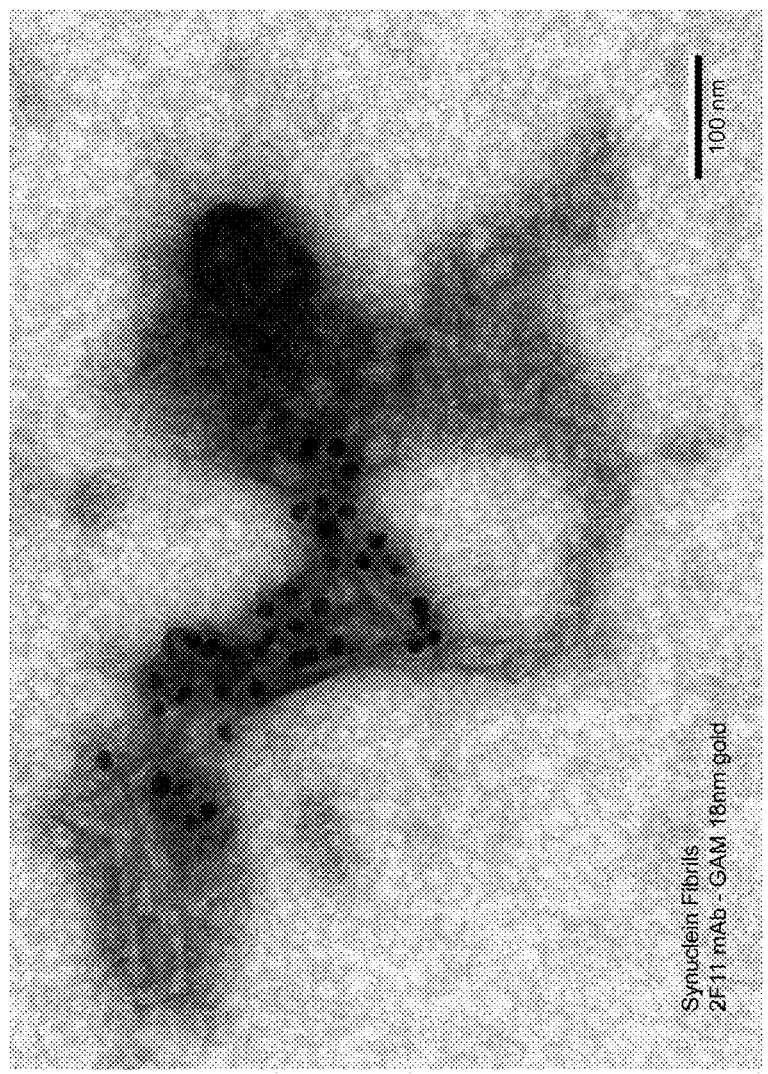
FIG. 8D shows electron microscopy analysis of 2F11 nano-gold conjugated (black dots) binding to human active α-synuclein aggregates. Bar: 100 nm.

In order to further demonstrate that the 2F11 antibody bound oligomeric α-synuclein fibrils, electron microscopy was used. The 2F11 antibody was conjugated to nano-gold particles and allowed bound to active α-synuclein aggregates. As shown in FIG. 8D, the 2F11 antibody bound active human α-synuclein aggregates.

Collectively, these results demonstrate that the 2F11 antibody is specific for active α-synuclein aggregates. and that the two species of aggregates (i.e. active and inactive α-synuclein aggregates) are dissimilar.

Example 5: 2F11 Blocks β-Sheet Structure Formation In Vitro

α-Synuclein/β-Sheet Structure Formation

The Thioflavin in vitro assay was used to measure progression of the α-synuclein reaction in the presence of various antibodies. The time kinetics of a typical α-synuclein reaction is shown in FIG. 9A. In the presence of an active α-synuclein aggregate and an active α-synuclein monomer (top line), the active α-synuclein monomer is "seeded" and changes from an alpha helical structure to beta sheet over time with a corresponding increase in Thioflavin fluorescence (similar to the result observed in FIG. 2A; Example 2).

Both active α-synuclein monomers and α-synuclein aggregates need to be present for β-sheet structure formation, and an increase Thioflavin fluorescence. Active α-synuclein aggregates resulted in a slight increase in Thioflavin fluorescence (second from top line) over time, but the amount of β-sheet structure formation is less than that of the mixture of an active α-synuclein aggregate+an active α-synuclein monomer (top line). Similar to the results shown in FIG. 2, active α-synuclein monomers can slowly self-seed over time (third line from top).

This assay was used to determine the effect of the antibodies 2F11, 4F1 and 3F8, all the same isotype antibodies (IgG1 kappa), and a random isotype control antibody: mouse monoclonal to hsp70, StressMarq, cat code #SMC- 104) on the reaction kinetics of Thioflavin fluorescence in the presence of active α-synuclein aggregate and an active α-synuclein monomer. The results are shown in FIG. 9B (antibodies added at start of reaction) and FIG. 9C (antibodies pre-incubated prior to start of reaction).

For the assay shown in FIG. 9B, 30 µg of antibody was added to 100 µM of active α-synuclein monomer along with 10 nM active α-synuclein aggregate. In the absence of added antibody, the time course kinetics of β-sheet structure formation in the presence of active α-synuclein aggregate and an active α-synuclein monomer (top line), active aggregate (third line from bottom) or active monomer (second line from bottom) is similar to that observed in FIG. 9A. When SMC-104 (second from top line) 4F1 (third from top line) or 3F8 (forth from top line) were added to the reaction mixture a decrease in total Thioflavin fluorescence was observed, however, a significant increase in β-sheet structure formation was still observed. Thioflavin fluorescence was greatly reduced in the presence of 2F11 (fourth line from bottom), showing reduced β-sheet structure formation in the presence of the 2F11 antibody.

The addition of the 2F11 antibody is highly disruptive and reduces the rate of β-sheet structure formation over the first 1000 minutes (16 hours). However, the reaction rate observed with active α-synuclein aggregate+an active α-synuclein monomer (top line), was similar to the reaction rate of the active substrates in the presence of 4F1 or 3F8, or the control antibody, SMC-104.

For the assay shown in FIG. 9C, 30 µg of antibody was added to 10 nM of active α-synuclein aggregate for 60 minutes, and the mixture washed to remove any unbound antibody prior to adding 100 µM active α-synuclein monomer to start the reaction. In the absence of added antibody, the time course kinetics of β-sheet structure formation in the presence of active α-synuclein aggregate and an active α-synuclein monomer (top line), active aggregate (fourth line from bottom) or active monomer (second line from bottom) is similar to that observed in FIG. 9A.

Pre-incubation of antibodies with the aggregates prior to starting the reaction resulted in the 2F11 antibody completely inhibiting the aggregation activity (third line from bottom) in a manner similar to either active α-synuclein monomer alone (second line from bottom), or α-synuclein aggregate alone (fourth line from bottom). The rate of increase in fluorescence over the first 1000 min in the presence of 2F11 reaction mixture was also greatly reduced compared with active α-synuclein aggregate and an active α-synuclein monomer (top line), and again approximated the kinetics observed with either active α-synuclein monomer, or α-synuclein aggregate.

Pre-incubation of the active α-synuclein aggregates prior to starting the reaction with 3F8 and 4F1 did not alter the rate of increase in florescence over the first 1000 min, and resulted in only slight difference of total florescence, when compared with the pre-incubation with the isotype control (SMC-104) antibody.

These results clearly show that the 2F11 antibody binds a component or structure that is required for the α-synuclein aggregation and fibrillation reaction to proceed to form the β-sheet structure. The 2F11 antibody therefore shows a neutralization effect on this reaction.

Tau β-Sheet Structure Formation

Due to the known interaction between tau and α-synuclein Li, X., et. al., 2016, J. Mol. Neurosci. 60:298-304), the effect of the monoclonal antibody 2F11 on tau induced β-sheet structure formation was examined using the Thioflavin assay. Tau fibrils were prepared using the method as described in Li W, Lee V M. (2006, Biochemistry. 45(51): 15692-15701. doi: 10.1021/bi061422+).

Antibody (60 ug of either 2F11 or SMC-104) was incubated with 10 nM Tau Fibril for 1 hour at 4° C. with shaking. The mixture was centrifuged at 10000 rpm for 5 minutes and rinsed with 1 mL PBS. This step was repeated 4 additional times. The supernatant was removed and Tau Fibril (with bound antibody) was resuspended in 10 µL PBS prior to adding 25 µM Tau monomer to start the reaction. Thioflavin T stock was added to a final concentration 25 µM. The Thioflavin T florescence was determined in each well (excitation 450 nm, emission 485 nm) after incubation at 37° C. from 1 hour up to 48 hours with shaking. The results are shown in FIG. 13.

A background florescence signal was observed when Tau fibril alone, or Tau monomer alone were assayed. However, a mixture of Tau monomer and Tau fibrils results in production of a strong fluorescence signal indicating β-sheet structure formation. The progression of the tau reaction was observed to be interrupted when monoclonal antibody 2F11 was pre-incubated with tau monomer and tau fibril prior to start of reaction. Monoclonal antibody SMC-104 (mouse monoclonal to hsp70) had little to no effect on the tau reaction.

Theses result show that the monoclonal antibody 2F11 blocks Tau fibril, β-sheet structure formation in vitro.

Example 6: 2F11 Inhibits Active α-Synuclein Fibril-Induced Lewy-Body Pathology In Vivo Given the fact, as shown in Example 5, that 2F11 showed the ability to inhibit the aggregation of α-synuclein in vitro, the ability of the 2F11 antibody to inhibit α-synuclein aggregation in primary cortical cells harvested from Sprague-Dawley rat embryo brains was examined.

As shown in FIG. 9D, the control sample, treated with DAPI and probed pSer129 alpha-synuclein antibody (upper left panel) only shows DAPI stained nuclei. The addition of active α-synuclein fibrils to primary brain cells followed by DAPI stating and probing with pSer129 alpha-synuclein antibody shows both DAPI stained nuclei and cells stained with the pSer129 antibody (upper right panel) and indicates binding of pSer129 to α-synuclein antibody, and α-synuclein induced pathology in the brain cells. When active α-synuclein fibrils and 2F11 were added to the primary brain cells and exposed to DAPI and probed with pSer129 alpha-synuclein antibody, DAPI stained nucleic with minor background levels of pSer129 staining was observed (lower panel). The addition of α-synuclein aggregates therefore induced Lewy-Body pathology in primary cortical cells (upper right panel), however, when the 2F11 antibody was added along with the α-synuclein aggregates, the Lewy-Body pathology was inhibited (lower panel).

These results demonstrate that 2F11 inhibits active α-synuclein fibril-induced Lewy-Body pathology in primary brain cells.

Intrastriatal Injection of 2F11 Antibody Reduces the Generation of Lewy-Body Pathology in Primary Rat Cortical Cells The ability of the 2F11 antibody to neutralize the generation of Lewy-Body pathology in rat cortical cells, in vivo was also examined. Rats were euthanized at 30 days post-injection (dpi). Four-month-old male Long Evans rats were randomized and divided into four groups. They received a 1-site intrastriatal injection of either sterile PBS (Control, 4 µl PBS), sonicated pre-formed α-syn fibrils (PFF; 4.2 ug total) or PFF plus antibody when applicable (2 µg). Two antibodies (2 µg antibody) were tested for their ability to neutralize Lewy-Body pathology formation: 2F11 known to neutralize the pathology in vitro, and 3D10, another α-synuclein antibody that is unable to neutralize the pathology generation in vitro.

Prior to the intrastriatal injection, PFF stored at −80° C. were thawed and sonicated at room temperature using a Sonic Dismembrator model 100 (Fisher Scientific) with 60 pulses at a 10% power (total of 30 second, 0.5 s on, 0.5 s off). Anesthetized rats (inhaled isoflurane) were placed into a stereotaxic device. The skull was exposed by doing a midline incision using a scalpel blade, and the surface of the skull dried to identify bregma. A 1 mm diameter hole is drilled until the dura. Either sterile PBS, PFF or PFF with antibody when appropriate was injected into the right dorsal striatum at one site to a total volume of 4 µl (AP +1.6 mm, ML +2.4 mm, DV −4.2 mm from skull) at a rate of 0.4 µl per minute using a 5 µl Hamilton syringe. After each injection, the syringe was left in place for 2 minutes and then slowly withdrawn. Animals were monitored weekly following surgery and sacrificed 30 days post-injection (dpi).

Animals were transcardially perfused with 200 mL of heparinized 0.1 M Phosphate Buffer Saline (PBS) followed by 200 mL of 4% Paraformaldehyde (PFA) diluted in 0.1 M PBS. Post perfusion, the brains were dissected and fixed by immersion in the same fixing solution (4% PFA in 0.1 M PBS) overnight at 4° C. Using a Vibratome (Leica VT1000S), brains were sliced in cold PBS into 50 micrometer sections. One every six slices were kept in the same well. One well per animal was used to perform the immunofluorescence staining. Sections were separated into wells of a 12-well plate and incubated for 1 hour at room temperature in 3 mL 2% Bovine Serum Albumin (BSA) and 0.2% Triton-100X in 0.1 M PBS. After samples were blocked and permeabilized, the slices were washed for 10 minutes in 2% BSA-PBS for a total of three washes. A 1:500 dilution of StressMarq SPC-742 (serine 129 phospho-specific α-synuclein antibody) was prepared in 2% BSA-PBS and added to each well. The slices were incubated with shaking overnight at 4° C. with a total volume of 3 mL per well. Samples were washed for 10 minutes in 2% BSA-PBS for a total of three washes. A 1:400 dilution of goat-anti-Rabbit secondary antibody conjugated with Alexa Fluor 488 in 2% BSA-PBS was prepared and added to each well. The slices were incubated with shaking for two hours at room temperature with a total volume of 3 mL per well. Samples were washed for 10 minutes in 2% BSA-PBS twice and then counterstained with DAPI for 10 minutes and washed in PBS for 10 minutes. Slices were mounted, allowed to dry for approximately 40 minutes and a coverslip was added with Fluoromont-G (ThermoFisher Scientific, Catalog #00-4958-02). Images were taken using an Olympus BX51 confocal microscope and Fluoview FV1000 software. DAPI was excited with a 405 nm laser and Alexa-488 was excited with a 461 nm laser. All acquisition parameters (e.g. laser power, HV, gain, z-step) were kept constant between samples.

Sections of cortical tissue obtained from rats treated with α-synuclein fibrils in PBS revealed localized fluorescence indicating binding of the α-synuclein antibody (pSer129) to α-synuclein fibrils and α-synuclein aggregate formation. However, in the PBS (control) treated rats, no fluorescence was observed, indicating no α-synuclein aggregate formation. Localized fluorescence was also observed in rat cortical cells that were treated with α-synuclein fibrils and the antibody 3D10, indicating binding of the antibody (pSer129) to α-synuclein fibrils and α-synuclein aggregate formation. The amount of localized binding in cortical cells receiving α-synuclein fibrils and the antibody 3D10, was similar to that observed in slices of cortical tissue obtained from rats administered α-synuclein fibril alone. While localized fluorescence was observed in cortical cells obtained from rat brain treated with α-synuclein fibrils and the antibody 2F11, both the number of localized binding sites, and the size of the localized binding sites, were reduced when compared to either the number and size of binding sites observed in cortical cells when treated with α-synuclein fibril alone, or α-synuclein fibrils and the antibody 3D10.

The above results demonstrate that treatment of brain tissue with the 2F11 antibody reduces the generation of Lewy-Body pathology in rat cortical cells, in vivo.

2F11 Reduces Cytotoxic Effect of α-Synuclein

α-synuclein is known to have cytotoxic effect, therefore the ability of the 2F11 antibody to reduce cytotoxicity in SHSY-5Y cells was examined.

Figure 9E:
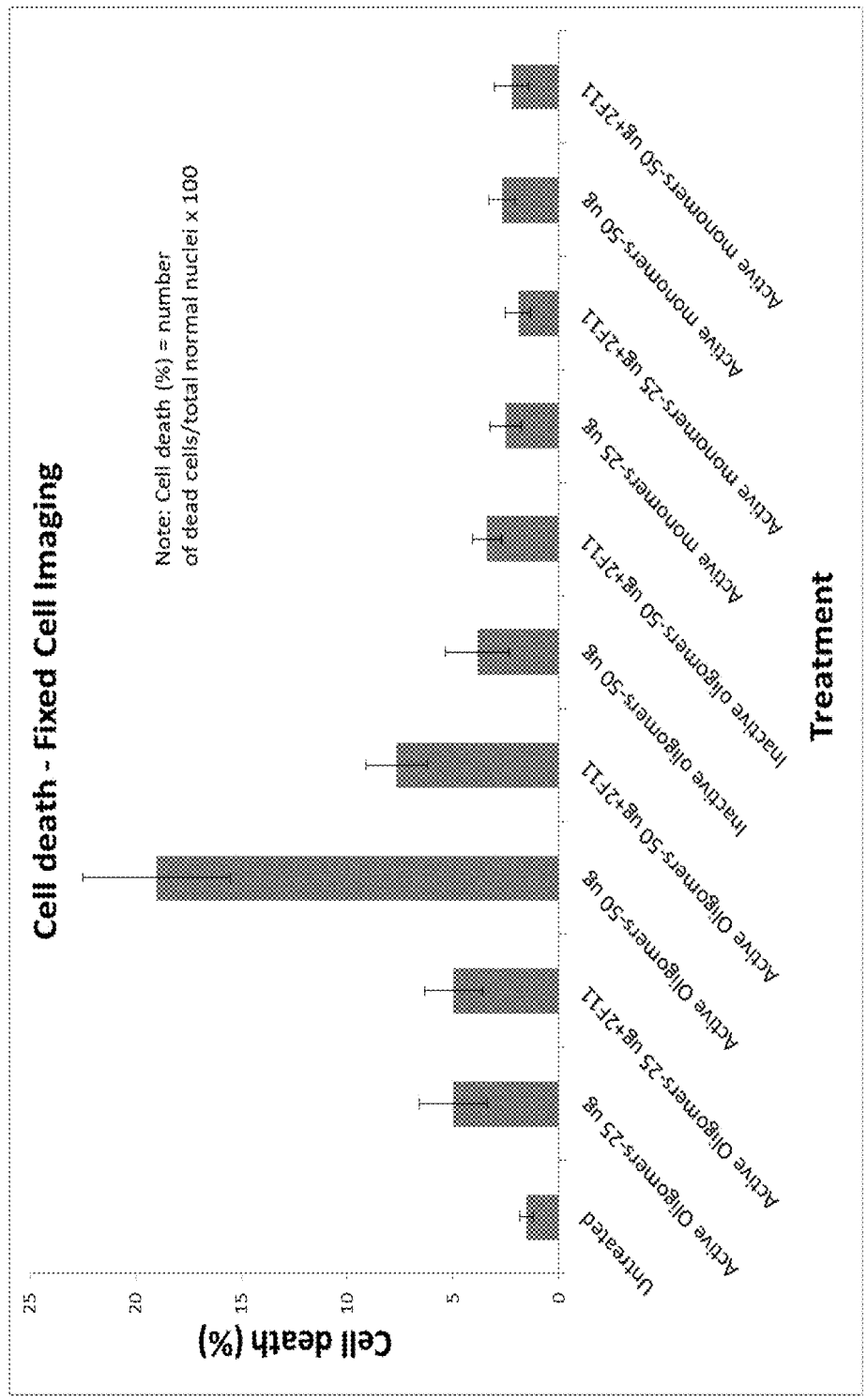
FIG. 9E shows cell death of human SHSY-5Y cells in the presence of active α-synuclein oligomers, inactive α-synuclein oligomers, active α-synuclein monomers in the presence and absence of the 2F11 antibody. Cell death (%): Number of dead cells/Total normal nuclei×100.

Human SHSY-5Y cells were seeded at 20,000 cells/well in a 96-well plate and differentiated in the presence of 10 µM RA for 5 days. Cells were washed with 1×PBS and the ability of the α-synuclein antibody (2F11) to neutralize the toxic effects of α-synuclein oligomers was tested. Active α-synuclein oligomers, inactive α-synuclein oligomers, and active α-synuclein monomers (at 25 µg/ml or 50 µg/ml) were pre-incubated with 5 µg/ml monoclonal 2F11 in serum-free DMEM for 2 h on a shaker at RT. Medium was removed and 100 µl of medium containing active α-synuclein aggregates+2F11 antibody was added to the relevant wells and incubated overnight at 37° C. After treatments, cells were immediately fixed with 10% neutral buffered formalin and immunostained using β-III tubulin antibody (β-III tubulin is used as a neuronal cell marker). Cell death was expressed as percent of total cells or percent of β-III positive neurons. The results are shown in FIG. 9E.

Adding active α-synuclein oligomers to human SHSY-5Y cells followed by the addition of active α-synuclein aggregates resulted in higher levels of cell death when compared to control (untreated) cells, cells exposed to inactive active α-synuclein oligomers, or cells exposed to active α-synuclein monomers. This result demonstrates that active α-synuclein oligomers may be recruited by active α-synuclein aggregates, and the reaction results in an increase in cell death compared to inactive α-synuclein oligomers.

Adding active α-synuclein oligomers to human SHSY-5Y cells followed by the addition of active α-synuclein aggregates+2F11 antibody reduced cell death (approx. 2.5 fold) to levels observed in cells exposed to inactive active α-synuclein oligomers, or active α-synuclein monomers. These results indicate that 2F11 blocks or neutralizes the toxic effects of α-synuclein oligomers in vivo.

Example 7: Epitope Mapping

Epitope binding of the 2F11, and several other antibodies including 4F1, 3F8 (and others that were prepared as described in Example 3) was assessed by binding to α-synuclein peptides of approx. 30 amino acids in length, each α-synuclein peptide overlapping with about 10 amino acid residues of the adjacent amino sequence (described above: "Peptide synthesis for epitope mapping").

The series of overlapping peptides were bound to BSA prior to analysis using ELISA, dot blots (DB) or western blots (WB).

As described in Example 3, approx. 20 antibodies were selected as binding active α-synuclein monomers, however, they exhibited differential binding under native or denatured conditions. Therefore, three methods were selected to include both denatured and native binding conditions for the mapping analysis. These methods involved: western blot (under denaturing conditions), dot blots (under non-denaturing conditions (using a similar output system to western blots but without denaturing the sample with ionic detergents such as sodium dodecyl sulfate, reducing agents and boiling temperatures), and ELISA (under non-denaturing conditions). The results of the binding analysis of 15 of the antibodies initially selected in Example 3 are shown in FIG. 10.

From the results shown in FIG. 10, the 2F11 clone exhibited a unique epitope map, being the only clone to specifically bind just amino acids 61-90 and amino acids 101-130 (as determined using ELISA). The remaining antibodies bound a different combination of regions. For example, clone 3F8 also exhibited strong binding to the C-terminal section (amino acids 101-130 and 121-140; using both denaturing and non-denaturing methods). Clone 3F8 also bound the amino acids 41-70.

These results further indicate the unique nature of the 2F11 antibody. The unique binding capacity of 2F11 allows it to bind and neutralize a core component of the alpha synuclein aggregation and fibrillization reaction.

Example 8: ELISA to Measure Virulent Oligomeric α-Synuclein

A sandwich-based ELISA test is prepared using 2F11. For control treatments, 4F1 and 3F8 antibodies may be used. Recombinant α-synuclein seeds, or an active α-synuclein aggregate may be used as a standard. The ELISA assay may be used to selectively measure virulent oligomeric α-synuclein. The assay does not identify inactive monomeric or inactive aggregated α-synuclein.

Example 9: Mouse Immunization

Alpha-syn transgenic (tg) mice (PD model; see URL: jax.org/strain/004479; Masliah et al., 2011) and non-tg mice are separately immunized using 2F11, 3F8, and 4F1 antibodies for 6 months of weekly intraperitoneal injections as defined in Masliah et al. 2011.
Behavioral Response The behavioral response of both the α-syn transgenic (tg) mice and non-tg mice is evaluated using Water maze, Pole test and Rotarod tests after 6 months of weekly intraperitoneal injections as described in Masliah et al. 2011). The results will determine if immunized tg mice have better memory recovery and were able to complete their tasks in similar fashion to non tg mice and determine if the antibody treatment reverses learning deficits.
Plasma Levels The titer of the 2F11, 3F8, 4F1 antibodies in mouse plasma and cerebrospinal fluid is determined over a 6 month period. Increasing titres in the brain, will show that the antibodies are able to cross the blood-brain barrier.
Immunohistochemistry After 6 months, the animals are sacrificed and samples of their hippocampus and neocortex are analyzed immunohistochemically (as described by Masliah et al. 2011). The results may show that immunized tg mice have altered levels of α-synuclein in their hippocampus and neocortex.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

Borghi R, Marchese R, Negro A, Marinelli L, Forloni G, Zaccheo D, et al. Full length alpha-synuclein is present in cerebrospinal fluid from Parkinson's disease and normal subjects. Neurosci Lett 2000; 287:65-7.

El-Agnaf O M, Salem S A, Paleologou K E, Curran M D, Gibson M J, Court J A, et al. Detection of oligomeric forms of alpha-synuclein protein in human plasma as a potential biomarker for Parkinson's disease. FASEB J 2006; 20:419-25.

Desplats, P.; Lee, H.; Bae, E.; Patrick, C.; Rockenstein, E.; Crews, L.; Spencer, B.; Masliah, E.; Lee, S. Inclusion formation and neuronal cell death through neuron-to-neuron transmission of -synuclein. PNAS 2009, 106, 13010-13015.

Kasuga K, Tokutake T, Ishikawa A, Uchiyama T, Tokuda T, Onodera O, et al. Differential levels of alpha-synuclein, beta-amyloid42 and tau in CSF between patients with dementia with Lewy bodies and Alzheimer's disease. J Neurol Neurosurg Psychiatry 2010; 81:608-10.

Bartels, T., Choi, J. G. and Selkoe, D. J. α-Synuclein occurs physiologically as a helically folded tetramer that resists aggregation. Nature (2011), 477, 107-110.

Wang. W., Petrovic, I., Chittuluru, J., Kaganovich, A, et al. A soluble α-synuclein construct forms a dynamic tetramer. Proc Natl Acad Sci USA 2011; 108:17797-17802.

Giasson, B. I., Murray, I. V. J., Trojanowski, J. Q., and Lee, V. M.-Y. (2001) A hydrophobic stretch of 12 amino acid residues in the middle of α-synuclein is essential for filament assembly. J. Biol. Chem. 276, 2380-2386.

Bedard, L., Lefevre, T., Morin-Michaud, E., and Auger, M. (2014) Besides Fibrillization: Putative Role of the Peptide Fragment 71-82 on the Structural and Assembly Behaviour of the α-synuclein. Biochemistry, 53, 6463-6472.

Volpicelli-Daley, L. A., Luk, K. C., and Lee, V. M-Y. (2014). Nature Protocols, 9(9), 2135-2145.

Jo, E., McLaurin, J., Yip, C. M., St George-Hyslop, P., and Fraser, P. E. (2000). Alpha-Synuclein membrane interactions and lipid specificity. J. Biol. Chem. 275, 34328-34334.

Lee, H. J., Choi, C., and Lee, S. J. (2002). Membrane-bound alpha-synuclein has a high aggregation propensity and the ability to seed the aggregation of the cytosolic form. J. Biol. Chem. 277, 671-678

Perrin, R. J., Woods, W. S., Clayton, D. F., and George, J. M. (2001). Exposure to long chain polyunsaturated fatty acids triggers rapid multimerization of synucleins. J. Biol. Chem. 276, 41958-41962.

Comellas, G., Lemkau, L. R., Zhou, D. H., George, J. M., and Rienstra, C. M. (2012). Structural intermediates during α-synuclein fibrillogenesis on phospholipid vesicles. J. Am. Chem. Soc. 134, 5090-5099.

Murray, I. V. J., Giasson, B. I., Quinn, S. M., Koppaka, V., Axelsen, P. H., Ischiropoulos, H., Trojanowski, J. Q. and Lee, V. M-y. (2003). Role of α-synuclein carboxy-terminus on fibril formation in vitro. Biochemistry, 42, 8530-8540.

Cremades, N.; Cohen, S. I. A.; Deas, E.; Abramov, A. Y.; Chen, A. Y.; Orte, A.; Sandal, M.; Clarke, R. W.;

Dunne, P.; Aprile, F. A.; et al. Direct observation of the interconversion of normal and toxic forms of α-synuclein. Cell 2012, 149, 1048-1059.

Hansen, C.; Angot, E.; Bergström, A.; Steiner, J. A.; Pieri, L.; Paul, G.; Outeiro, T. F.; Melki, R.; Kallunki, P.; Fog, K. α-Synuclein propagates from mouse brain to grafted dopaminergic neurons and seeds aggregation in cultured human cells. J. Clin. Investig. 2011, 121, 715-725.

Shvadchak, V., Claessens, M. M. A. E., and Subramaniam, V. (2015). Fibril breaking accelerates α-synuclein fibrillization. J. Phys. Chem. B., 119, 1912-1918.

Horvath, I., Sellstedt, M., Weise, C., Nordvall, L-M., Prasad, G. K., Olofsson, A., Larsson, G., Almqvist, F., and Willung-Stafshede, P. (2013). Modulation of α-synuclein fibrillization by ring-fused 2-pyridones: templation and inhibition involve oligomers with different structures.

Lashuel, H. A.; Petre, B. M.; Wall, J.; Simon, M.; Nowak, R. J.; Walz, T.; Lansbury, P. T. α-Synuclein, especially the Parkinson's disease-associated mutants, forms pore-like annular and tubular protofibrils. J. Mol. Biol. 2002, 322, 1089-1102.

Kostka, M.; Hogen, T.; Danzer, K. M.; Levin, J.; Habeck, M.; Wirth, A.; Wagner, R.; Glabe, C. G.; Finger, S.; Heinzelmann, U.; et al. Single particle characterization of iron-induced pore-forming alpha-synuclein oligomers. J. Biol. Chem. 2008, 283, 10992-11003.

Zhang, H.; Griggs, A.; Rochet, J.-C.; Stanciu, L. A. In vitro study of -synuclein protofibrils by cryo-EM suggests a Cu2+-dependent aggregation pathway. Biophys. J. 2013, 104, 2706-2713.

Lorenzen, N.; Nielsen, S. B.; Buell, A. K.; Kaspersen, J. D.; Arosio, P.; Vad, B. S.; Paslawski, W.; Christiansen, G.; Valnickova-Hansen, Z.; Andreasen, M.; et al. The role of stable-synuclein oligomers in the molecular events underlying amyloid formation. J. Am. Chem. Soc. 2014, 136, 3859-3868.

Cappai, R, Leck, S.-L., Tew, D J., Williamson, N. A., Smith, D. P., Galatis, D., Sharpies, R A, Curtain, C. C., Ali, F. E., Cherny, R A, Culvenor, J. G., Bottomley, S. P., Masters, C. L., Barnham, K. J. and Hill, A F. (2005), Dopamine promotes α-synuclein aggregation into SDS-resistant soluble oligomers via a distinct folding pathway. The FASEB J. 2005, 19, 1377-1379.

Giasson, B. I., Jakes, R., Goedert, M., Duda, J. E., Leight, S., Trojanowski, J. Q., and Lee, V. M.-Y. (2000). A panel of Epitope-specific antibodies detects protein domains distributed throughout human α-synuclein in Lewy bodies in Parkinson's disease. J. Neurosci. Res. 59, 528-533.

Luk, K. C., Song, C., O'Brien, P., Stieber, A., Branch, J. R., Brunden, K. R., Trojanowski, J. Q., and Lee, V. M.-Y. (2009). Exogenous α-synuclein fibrils seed the formation of Lewy body-like intracellualar inclusions in cultured cells. PNAS, 106(47), 20051-20056.

Masliah E, Rockenstein E, Adame A, Alford M, Crews L, Hashimoto M, Seubert P, Lee M, Goldstein J, Chilcote T, Games D, Schenk D (2005) Effects of alpha-synuclein immunization in a mouse model of Parkinson's disease. Neuron 46:857-868.

Masliah E, Rockenstein E, Mante M, Crews L, Spencer B, Adame A, Patrick C, Trejo M, Ubhi K, Rohn T T, Mueller-Steiner S, Seubert P, Barbour R, McConlogue L, Buttini M, Games D, Schenk D (2011) Passive immunization reduces behavioral and neuropathological deficits in an alpha synuclein transgenic model of Lewy body disease. PLoS One 6:e19338.

Bae, E-J., Lee, H-J., Rockenstein, E., Ho, D-H., Park E-B., Yang, N-Y., Desplats, P., Masliah E., and Lee, S-J. (2012). Antibody-Aided Clearance of Extracellular α-Synuclein Prevents Cell-to-Cell Aggregate Transmission. Journal of Neuroscience, Sep. 26, 2012, 32(39):13454-13469.

Lee, H-J., Bae, E-J., Jang, A., Ho, D-H, Cho, E-D., Suk, J-E., Yun, Y-M, Lee, S-J. (2011). Enzyme-linked immunosorbent assays for alpha-synuclein with species and multimeric state specificities. Journal of Neuroscience Methods 199; 249-257.

Lannfelt, L., Bergström, J., Ingelsson, M., Gellerfors, P. Antibodies and vaccines for use in therapeutic and diagnostic methods for α-synuclein-related disorders U.S. Pat. No. 8,809,506B2.

Weihofen, A., Grimm, J., Nitsch, R., Hock, C. Human anti-alpha-synuclein antibodies. U.S. Pat. No. 8,940, 276B2.

Nordstrom, E., Kasrayan, A., Ekberg, M., Screpanti Sundquist, V., Lannfelt, L., Holmquist, M. Protofibril-binding antibodies and their use in therapeutic and diagnostic methods for Parkinson's disease, dementia with Lewy bodies and other α-synucleinopathies. U.S. Pat. No. 9,084,832B2

Ariesandi, W., Chang, C-F., Chen, T-E., and Chen, Y-R. (2013). Temperature-Dependent Structural Changes of Parkinson's Alpha-Synuclein Reveal the Role of Pre-Existing Oligomers in Alpha-Synuclein Fibrillization. PLOS ONE, 8 (1); e53487

---

What is claimed is:

1. An antibody which specifically binds toxic α-synuclein, which comprises heavy chain complementarity determining region (CDR) sequences as set out in SEQ ID NOs: 14, 15, and 16, and comprises light chain CDR sequences as found in the antibody produced by the hybridoma deposited under ATCC PTA-124174, with the priviso that the antibody excludes the antibody produced by the hybridoma deposited under ATCC PTA-124174.

2. The antibody of claim 1, comprising an antigen binding domain as found in the antibody produced by the hybridoma deposited under ATCC PTA-124174.

3. A composition comprising the antibody of claim 1, in a pharmaceutically acceptable carrier, adjuvant, vehicle or excipient.

4. A vaccine comprising the antibody of claim 1, in a pharmaceutically acceptable carrier, adjuvant, vehicle or excipient.

5. A method of reducing toxic α-synuclein, or tau fibrillar formation, in a subject in need thereof comprising administering the antibody of claim 1, or a pharmaceutical composition comprising the antibody of claim 1, to the subject.

6. The method of claim 5, wherein the composition is administered to the subject orally, intranasally, intramuscularly, intraperitoneally, intravenously, or subcutaneously.

7. The method of claim 5, wherein prior to the step of administering, a level of toxic α-synuclein, or tau fibrils, in the subject is determined, and after a period of time following the step of administering, a second level of toxic α-synuclein, or tau fibrils, is determined.

8. A method of determining the presence of toxic oligomeric α-synuclein, or tau fibrils, in a sample comprising, exposing the sample to the antibody of claim 1, and determining if the antibody binds to protein in the sample, wherein binding is indicative of the presence of the toxic oligomeric α-synuclein, or tau fibrils.

9. The method of claim 8, wherein:
the sample is separated using non-denaturing electrophoresis prior to the step of exposing, and the separated protein is probed using the antibody via western analysis, wherein binding of one or more high molecular weight protein is indicative of the presence of the toxic oligomeric α-synuclein, or tau fibrils, in the sample; or
a dot blot of the sample is probed using the antibody, and binding of the antibody to the sample is indicative of the presence of the toxic oligomeric α-synuclein, or the tau fibrils.

10. A method of treating a synucleinopathy, a pathological condition characterized by Lewy bodies, Parkinson's disease, dementia with Lewy bodies, multiple system atrophy, sporadic Alzheimer's disease, or familial Alzheimer's disease, comprising administering the antibody of claim 1, or a pharmaceutical composition comprising the antibody of claim 1, to a subject.

11. A method for determining the presence, concentration, or both the presence and concentration, of a toxic oligomeric α-synuclein, or a tau fibril, in a sample comprising, applying a sample to a surface that has been prepared using the antibody of claim 1 and determining an occurrence, an amount, or an occurrence and an amount, of toxic α-synuclein aggregate, or tau aggregate, that is bound to the antibody, thereby determining the presence, concentration, or both the presence and concentration, of toxic α-synuclein aggregate, or tau aggregate, in the sample.

12. A bispecific antibody for transmigrating the blood brain barrier, the bispecific antibody comprising one or more carrier molecules attached to the antibody of claim 1, wherein the one or more carrier molecules is derived from a transferin receptor (TfR)-binding antibody, or from an insulin-like growth factor 1 receptor (IGF1R)-binding antibody.

13. The bispecific antibody of claim 12, wherein the bispecific antibody is a monovalent-bispecific antibody or a bivalent-bispecific antibody.

14. A method of treating a taupathy, a pathological condition characterized by Neurofibrillary tangles, Alzheimer's disease, Pick's disease, progressive supranuclear palsy, corticobasal degeneration, frontotemporal dementia, argyrophilic grain disease, primary age-related tauopathy, neurofibrillary tangle-only dementia, or a globular glial tauopathy, the method comprising administering the antibody of claim 1, or pharmaceutical composition comprising the antibody of claim 1, to a subject.

15. The method of claim 5, wherein the antibody comprises an antigen binding domain as found in the antibody produced by the hybridoma deposited under ATCC PTA-124174.

16. The method of claim 8, wherein the antibody that is exposed to the sample comprises an antigen binding domain as found in the antibody produced by the hybridoma deposited under ATCC PTA-124174.

17. The method of claim 10, wherein the antibody comprises an antigen binding domain as found in the antibody produced by the hybridoma deposited under ATCC PTA-124174.

18. The method of claim 12, wherein antibody comprises an antigen binding domain as found in the antibody produced by the hybridoma deposited under ATCC PTA-124174.

19. The method of claim 14, wherein the antibody comprises an antigen binding domain as found in the antibody produced by the hybridoma deposited under ATCC PTA-124174.

* * * * *

SEQUENCE LISTING

<160> NUMBER OF SEQ ID NOS: 25

<210> SEQ ID NO 1
<211> LENGTH: 140
<212> TYPE: PRT
<213> ORGANISM: Mus musculus

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val

```
                35                  40                  45
Val His Gly Val Thr Thr Val Ala Glu Lys Thr Lys Glu Gln Val Thr
 50                  55                  60
Asn Val Gly Gly Ala Val Val Thr Gly Val Thr Ala Val Ala Gln Lys
 65                  70                  75                  80
Thr Val Glu Gly Ala Gly Asn Ile Ala Ala Thr Gly Phe Val Lys
                 85                  90                  95
Lys Asp Gln Met Gly Lys Gly Glu Glu Gly Tyr Pro Gln Glu Gly Ile
                100                 105                 110
Leu Glu Asp Met Pro Val Asp Pro Gly Ser Glu Ala Tyr Glu Met Pro
                115                 120                 125
Ser Glu Glu Gly Tyr Gln Asp Tyr Glu Pro Glu Ala
                130                 135                 140

<210> SEQ ID NO 2
<211> LENGTH: 140
<212> TYPE: PRT
<213> ORGANISM: Homo sapiens

<400> SEQUENCE: 2

Met Asp Val Phe Met Lys Gly Leu Ser Lys Ala Lys Glu Gly Val Val
  1               5                  10                  15
Ala Ala Ala Glu Lys Thr Lys Gln Gly Val Ala Glu Ala Ala Gly Lys
                 20                  25                  30
Thr Lys Glu Gly Val Leu Tyr Val Gly Ser Lys Thr Lys Glu Gly Val
                 35                  40                  45
Val His Gly Val Ala Thr Val Ala Glu Lys Thr Lys Glu Gln Val Thr
 50                  55                  60
Asn Val Gly Gly Ala Val Val Thr Gly Val Thr Ala Val Ala Gln Lys
 65                  70                  75                  80
Thr Val Glu Gly Ala Gly Ser Ile Ala Ala Ala Thr Gly Phe Val Lys
                 85                  90                  95
Lys Asp Gln Leu Gly Lys Asn Glu Glu Gly Ala Pro Gln Glu Gly Ile
                100                 105                 110
Leu Glu Asp Met Pro Val Asp Pro Asp Asn Glu Ala Tyr Glu Met Pro
                115                 120                 125
Ser Glu Glu Gly Tyr Gln Asp Tyr Glu Pro Glu Ala
                130                 135                 140

<210> SEQ ID NO 3
<211> LENGTH: 30
<212> TYPE: PRT
<213> ORGANISM: artificial
<220> FEATURE:
<223> OTHER INFORMATION: AA 1-30 peptide

<400> SEQUENCE: 3

Met Asp Val Phe Met Lys Gly Leu Ser Lys Ala Lys Glu Gly Val Val
  1               5                  10                  15
Ala Ala Ala Glu Lys Thr Lys Gln Gly Val Ala Glu Ala Ala
                 20                  25                  30

<210> SEQ ID NO 4
<211> LENGTH: 30
<212> TYPE: PRT
<213> ORGANISM: artificial
<220> FEATURE:
<223> OTHER INFORMATION: AA 21-50 peptide
```

-continued

```
<400> SEQUENCE: 4

Lys Thr Lys Gln Gly Val Ala Glu Ala Gly Lys Thr Lys Glu Gly
1               5                   10                  15
Val Leu Tyr Val Gly Ser Lys Thr Lys Glu Gly Val Val His
            20                  25                  30

<210> SEQ ID NO 5
<211> LENGTH: 30
<212> TYPE: PRT
<213> ORGANISM: artificial
<220> FEATURE:
<223> OTHER INFORMATION: AA 41-70 PEPTIDE

<400> SEQUENCE: 5

Gly Ser Lys Thr Lys Glu Gly Val Val His Gly Val Ala Thr Val Ala
1               5                   10                  15
Glu Lys Thr Lys Glu Gln Val Thr Asn Val Gly Gly Ala Val
            20                  25                  30

<210> SEQ ID NO 6
<211> LENGTH: 30
<212> TYPE: PRT
<213> ORGANISM: artificial
<220> FEATURE:
<223> OTHER INFORMATION: AA 61-90 PEPTIDE

<400> SEQUENCE: 6

Glu Gln Val Thr Asn Val Gly Gly Ala Val Val Thr Gly Val Thr Ala
1               5                   10                  15
Val Ala Gln Lys Thr Val Glu Gly Ala Gly Ser Ile Ala Ala
            20                  25                  30

<210> SEQ ID NO 7
<211> LENGTH: 30
<212> TYPE: PRT
<213> ORGANISM: artificial
<220> FEATURE:
<223> OTHER INFORMATION: AA 81-110 PEPTIDE

<400> SEQUENCE: 7

Thr Val Glu Gly Ala Gly Ser Ile Ala Ala Ala Thr Gly Phe Val Lys
1               5                   10                  15
Lys Asp Gln Leu Gly Lys Asn Glu Glu Gly Ala Pro Gln Glu
            20                  25                  30

<210> SEQ ID NO 8
<211> LENGTH: 30
<212> TYPE: PRT
<213> ORGANISM: artificial
<220> FEATURE:
<223> OTHER INFORMATION: AA 101-130 PEPTIDE

<400> SEQUENCE: 8

Gly Lys Asn Glu Glu Gly Ala Pro Gln Glu Gly Ile Leu Glu Asp Met
1               5                   10                  15
Pro Val Asp Pro Asp Asn Glu Ala Tyr Glu Met Pro Ser Glu
            20                  25                  30

<210> SEQ ID NO 9
<211> LENGTH: 20
<212> TYPE: PRT
<213> ORGANISM: artificial
<220> FEATURE:
<223> OTHER INFORMATION: AA 121-140 PEPTIDE
```

<400> SEQUENCE: 9

Asp Asn Glu Ala Tyr Glu Met Pro Ser Glu Glu Gly Tyr Gln Asp Tyr
1               5                   10                  15

Glu Pro Glu Ala
            20

<210> SEQ ID NO 10
<211> LENGTH: 411
<212> TYPE: DNA
<213> ORGANISM: artificial
<220> FEATURE:
<223> OTHER INFORMATION: variable region (heavy chain - IgG1 isotype) of
      for 2F11

<400> SEQUENCE: 10
atgaaatgca gctgggtcat cttcttcctg atggcagtgg ttataggaat caattcagag    60
gttcagctgc agcagtctgg ggcagagctt gtgaggtcag gggcctcagt caagttgtcc   120
tgcacagctt ctggcttcaa cattaaagac tactatatgt tttgggtgaa gcagaggcct   180
gaacagggcc tggagtggat tggatggaat gatcctgaga atggtgatac tgaatatgcc   240
ccgaagttcc agggcaaggc cactatgact gcagacacat cctccaacac agcctaccta   300
cagctcagca gcctgacatc tgaggacact gccgtctatt actgtaatgc atgggatggt   360
aactatgtta tggactactg gggtcaagga acctcagtca ccgtctcctc a            411

<210> SEQ ID NO 11
<211> LENGTH: 137
<212> TYPE: PRT
<213> ORGANISM: artificial
<220> FEATURE:
<223> OTHER INFORMATION: variable region (heavy chain - IgG1 isotype) of
      for 2F11

<400> SEQUENCE: 11

Met Lys Cys Ser Trp Val Ile Phe Phe Leu Met Ala Val Val Ile Gly
1               5                   10                  15

Ile Asn Ser Glu Val Gln Leu Gln Gln Ser Gly Ala Glu Leu Val Arg
            20                  25                  30

Ser Gly Ala Ser Val Lys Leu Ser Cys Thr Ala Ser Gly Phe Asn Ile
        35                  40                  45

Lys Asp Tyr Tyr Met Phe Trp Val Lys Gln Arg Pro Glu Gln Gly Leu
    50                  55                  60

Glu Trp Ile Gly Trp Asn Asp Pro Glu Asn Gly Asp Thr Glu Tyr Ala
65                  70                  75                  80

Pro Lys Phe Gln Gly Lys Ala Thr Met Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Asn Ala Trp Asp Gly Asn Tyr Val Met Asp Tyr Trp Gly
        115                 120                 125

Gln Gly Thr Ser Val Thr Val Ser Ser
    130                 135

<210> SEQ ID NO 12
<211> LENGTH: 396
<212> TYPE: DNA
<213> ORGANISM: artificial
<220> FEATURE:
<223> OTHER INFORMATION: light chain variable region (Kappa) of for 2F11

-continued

<400> SEQUENCE: 12

```
atggattttc aggtgcagat tttcagcttc ctgctaatca gtgcctcagt cataatgtcc      60
agaggacaaa ttgttctcac ccagtctcca gcaatcatgt ctgcatctct aggggaacgg     120
gtcaccatga cctgcactgc cagctcaagt gtaagttcca gttacttgca ctggtaccag     180
cagaagccag atcctcccc caaactctgg atttatagca catccaacct ggcttctgga     240
gtcccacctc gcttcagtgg cagtgggtct gggacctctt actctctcac aatcagcagc     300
atggaggctg aagatgctgc cacttattac tgccaccagt atcatcgttc cccacccatg     360
tacacgttcg agggggggac caagctggaa ataaaa                               396
```

<210> SEQ ID NO 13
<211> LENGTH: 130
<212> TYPE: PRT
<213> ORGANISM: artificial
<220> FEATURE:
<223> OTHER INFORMATION: light chain variable region (Kappa) of for 2F11

<400> SEQUENCE: 13

```
Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Ser Ser Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Pro Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Pro Met Tyr Thr Phe Gly Gly Gly Thr Lys
        115                 120                 125

Leu Glu
    130
```

<210> SEQ ID NO 14
<211> LENGTH: 5
<212> TYPE: PRT
<213> ORGANISM: artificial
<220> FEATURE:
<223> OTHER INFORMATION: monoclonal antibody 2F11 (heavy chain)

<400> SEQUENCE: 14

```
Asp Tyr Tyr Met Phe
1               5
```

<210> SEQ ID NO 15
<211> LENGTH: 17
<212> TYPE: PRT
<213> ORGANISM: artificial
<220> FEATURE:
<223> OTHER INFORMATION: monoclonal antibody 2F11 (heavy chain)

<400> SEQUENCE: 15

```
Trp Asn Asp Pro Glu Asn Gly Asp Thr Glu Tyr Ala Pro Lys Phe Gln
1               5                   10                  15
```

Gly

<210> SEQ ID NO 16
<211> LENGTH: 8
<212> TYPE: PRT
<213> ORGANISM: artificial
<220> FEATURE:
<223> OTHER INFORMATION: monoclonal antibody 2F11 (heavy chain)

<400> SEQUENCE: 16

Asn Ala Trp Asp Gly Asn Tyr Val
1               5

<210> SEQ ID NO 17
<211> LENGTH: 12
<212> TYPE: PRT
<213> ORGANISM: artificial
<220> FEATURE:
<223> OTHER INFORMATION: monoclonal antibody 2F11 (light chain)

<400> SEQUENCE: 17

Thr Ala Ser Ser Ser Val Ser Ser Ser Tyr Leu His
1               5                   10

<210> SEQ ID NO 18
<211> LENGTH: 7
<212> TYPE: PRT
<213> ORGANISM: artificial
<220> FEATURE:
<223> OTHER INFORMATION: monoclonal antibody 2F11 (light chain)

<400> SEQUENCE: 18

Ser Thr Ser Asn Leu Ala Ser
1               5

<210> SEQ ID NO 19
<211> LENGTH: 11
<212> TYPE: PRT
<213> ORGANISM: artificial
<220> FEATURE:
<223> OTHER INFORMATION: monoclonal antibody 2F11 (light chain)

<400> SEQUENCE: 19

His Gln Tyr His Arg Ser Pro Pro Met Tyr Thr
1               5                   10

<210> SEQ ID NO 20
<211> LENGTH: 15
<212> TYPE: DNA
<213> ORGANISM: artificial
<220> FEATURE:
<223> OTHER INFORMATION: monoclonal antibody 2F11 (heavy chain)

<400> SEQUENCE: 20
gactactata tgttt                                                    15

<210> SEQ ID NO 21
<211> LENGTH: 51
<212> TYPE: DNA
<213> ORGANISM: artificial
<220> FEATURE:
<223> OTHER INFORMATION: monoclonal antibody 2F11 (heavy chain)

<400> SEQUENCE: 21
tggaatgatc ctgagaatgg tgatactgaa tatgccccga agttccaggg c            51

```
<210> SEQ ID NO 22
<211> LENGTH: 24
<212> TYPE: DNA
<213> ORGANISM: artificial
<220> FEATURE:
<223> OTHER INFORMATION: monoclonal antibody 2F11 (heavy chain)

<400> SEQUENCE: 22
aatgcatggg atggtaacta tgtt                                          24

<210> SEQ ID NO 23
<211> LENGTH: 36
<212> TYPE: DNA
<213> ORGANISM: artificial
<220> FEATURE:
<223> OTHER INFORMATION: monoclonal antibody 2F11 (light chain)

<400> SEQUENCE: 23
actgccagct caagtgtaag ttccagttac ttgcac                             36

<210> SEQ ID NO 24
<211> LENGTH: 21
<212> TYPE: DNA
<213> ORGANISM: artificial
<220> FEATURE:
<223> OTHER INFORMATION: monoclonal antibody 2F11 (light chain)

<400> SEQUENCE: 24
agcacatcca acctggcttc t                                             21

<210> SEQ ID NO 25
<211> LENGTH: 33
<212> TYPE: DNA
<213> ORGANISM: artificial
<220> FEATURE:
<223> OTHER INFORMATION: monoclonal antibody 2F11 (light chain)

<400> SEQUENCE: 25
caccagtatc atcgttcccc acccatgtac acg                                33
```